US012753234B2

(12) United States Patent
Knapp et al.

(10) Patent No.: US 12,753,234 B2
(45) Date of Patent: *Oct. 6, 2026

(54) CANINE PD-L1 ANTIBODY, ANTIGEN BINDING FRAGMENTS THEREOF, AND METHODS OF USE THEREOF

(71) Applicant: PURDUE RESEARCH FOUNDATION, West Lafayette, IN (US)

(72) Inventors: Deborah Knapp, West Lafayette, IN (US); Deepika Dhawan, West Lafayette, IN (US); Seung-Oe Lim, West Lafayette, IN (US); Perry Kirkham, Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/207,035

(22) Filed: May 13, 2025

(65) Prior Publication Data

US 2025/0277039 A1 Sep. 4, 2025

Related U.S. Application Data

(63) Continuation-in-part of application No. PCT/US2023/079712, filed on Nov. 14, 2023.

(60) Provisional application No. 63/383,909, filed on Nov. 15, 2022.

(51) Int. Cl.

| | |
|---|---|
| ***A61P 35/00*** | (2006.01) |
| ***C07K 16/28*** | (2006.01) |
| *A61K 39/00* | (2006.01) |

(52) U.S. Cl.

CPC .......... *C07K 16/2827* (2013.01); *A61P 35/00* (2018.01); *C07K 16/2818* (2013.01); *A61K 2039/505* (2013.01); *A61K 2039/545* (2013.01); *C07K 2317/24* (2013.01); *C07K 2317/31* (2013.01); *C07K 2317/33* (2013.01); *C07K 2317/565* (2013.01); *C07K 2317/92* (2013.01)

(58) Field of Classification Search

CPC ............ C07K 16/2827; C07K 16/2818; C07K 2317/24; C07K 2317/31; C07K 2317/33; C07K 2317/565; C07K 2317/92; A61P 35/00; A61K 2039/505; A61K 2039/545

See application file for complete search history.

(56) References Cited

U.S. PATENT DOCUMENTS

| | | | |
|---|---|---|---|
| 2010/0125127 | A1 | 5/2010 | Mikesell et al. |
| 2016/0311902 | A1 | 10/2016 | Morsey et al. |
| 2016/0324932 | A1 | 11/2016 | Baldwin et al. |
| 2016/0333096 | A1 | 11/2016 | Morsey et al. |
| 2018/0237535 | A1 | 8/2018 | Morsey et al. |
| 2020/0023076 | A1 | 1/2020 | Fotin-Mleczek et al. |
| 2020/0109212 | A1 | 4/2020 | Morsey et al. |
| 2020/0407414 | A1 | 12/2020 | Lancaster et al. |
| 2022/0088182 | A1 | 3/2022 | Zion et al. |

FOREIGN PATENT DOCUMENTS

| | | | |
|---|---|---|---|
| WO | WO-2013054127 A1 * | 4/2013 | ................ A61P 9/14 |
| WO | 2022033435 | 2/2022 | |
| WO | WO-2022109403 A1 * | 5/2022 | .............. A61P 17/04 |
| WO | 2022192898 | 9/2022 | |

OTHER PUBLICATIONS

International Search Report and Written Opinion for PCT/US2023/079712, dated Apr. 24, 2024.
Wright, et al., "Chain C, Monoclonal antibody 9AD4 light chain", Genbank, National Center for Biotechnology Information, 2014, retrieved from: https://www.ncbi.nlm.nih.gov/protein/672886773.
Haji-Ghassemi, et al., "Chain B, S25-26 Fab (IgG1k) heavy chain", Genbank, National Center for Biotechnology Information, 2014, retrieved from: https://www.ncbi.nlm.nih.gov/protein/609412395.
Xue, et al., "Canis lupus familiaris immunoglobulin heavy chain IGH-17 mRNA, complete", Genbank, National Center for Biotechnology Information, 2018, retrieved from: https://www.ncbi.nlm.nih.gov/nuccore/1494245240.
Takahashi, et al., "Immunoglobulin heavy chain, partial [Mus musculus]", Genbank, National Center for Biotechnology Information, 2012, retrieved from: https://www.ncbi.nlm.nih.gov/protein/475393858.
International Search Report and Written Opinion for PCT/US2025/018549, dated May 8, 2025.
Barroso-Gomila, et al. "Identification of proximal SUMO-dependent interactors using SUMO-ID", 2021, Nature Communications vol. 12, Article No. 6671.
Office Action from U.S. Appl. No. 19/071,424, dated Apr. 24, 2025.

* cited by examiner

*Primary Examiner* — Misook Yu
*Assistant Examiner* — Dennis George
(74) *Attorney, Agent, or Firm* — Hovey Williams LLP; Crissa A. Cook

(57) ABSTRACT

Caninized antibodies and antigen binding fragments thereof are provided that bind programmed death ligand 1 in a canine subject. Methods of treating cancer in a canine subject using the caninized antibodies and/or antigen binding fragments are also provided, as are methods for predicting and modeling anti-cancer activity of a test compound in a subject.

12 Claims, 29 Drawing Sheets
(7 of 29 Drawing Sheet(s) Filed in Color)
Specification includes a Sequence Listing.

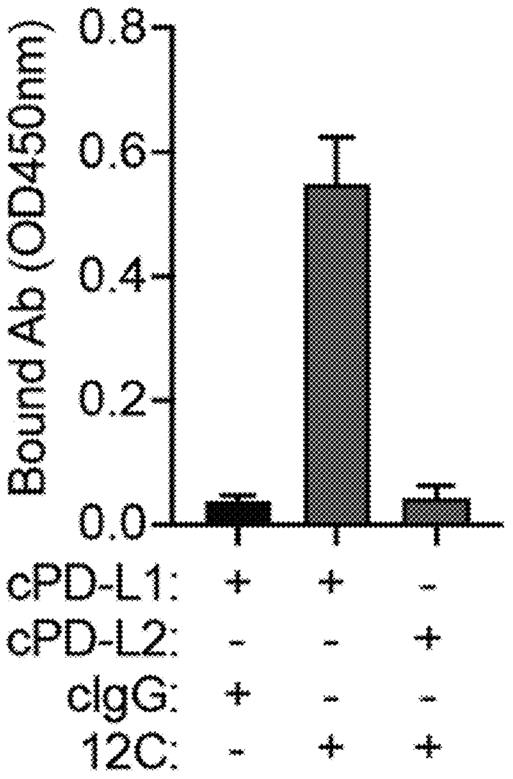
*Fig. 5C*
*Fig. 5D*
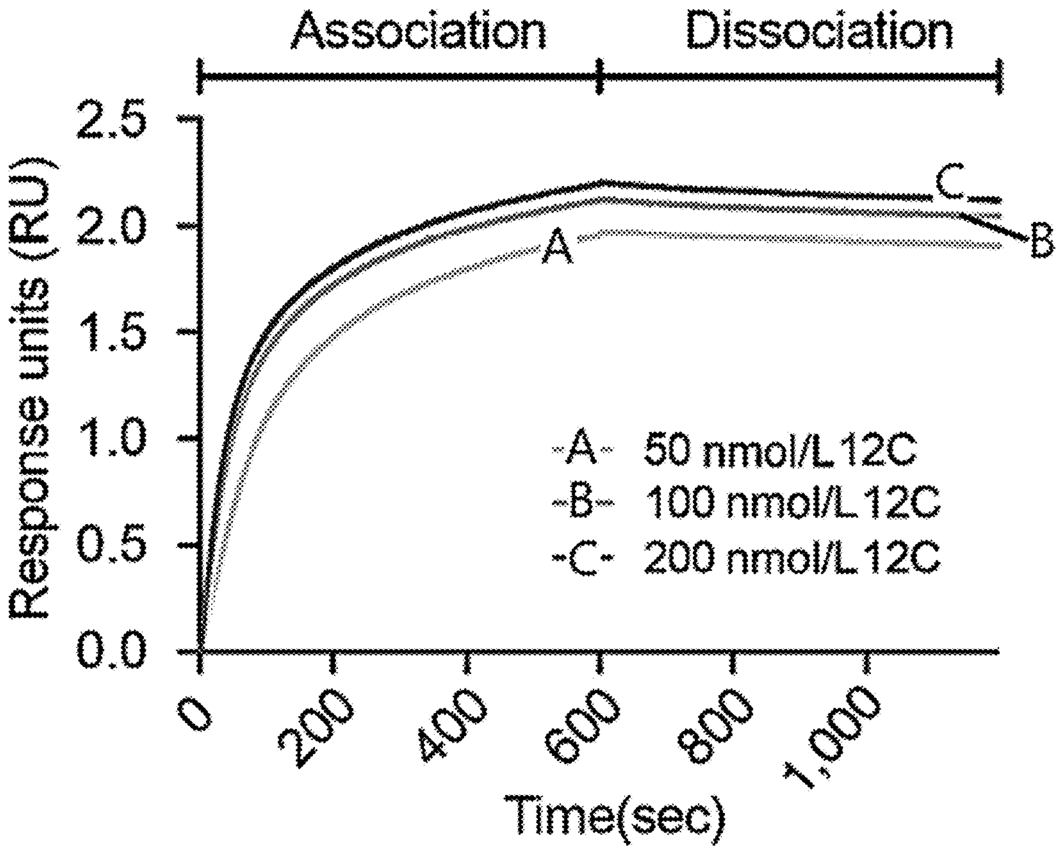

SEQUENCE LISTING

```
Sequence total quantity: 29
SEQ ID NO: 1            moltype = AA  length = 247
FEATURE                 Location/Qualifiers
source                  1..247
                        mol_type = protein
                        note = cPD-L1_12C10E4_dK light chain of the cPD-L1 12C10E4
                         antibody
                        organism = synthetic construct
SEQUENCE: 1
MESDTLLLWV LLLWVPGSAG DIVLTQSPAS LAVSLGQRAT ISCRASESVE YYGTSLMQWY  60
QQKPGQPPKL LIFAASNVKS GVPARFSGSG SGTDFSLNIH PVEEDDIAMY FCQQSGKVPH  120
TFGGGTKLEI KRSMEIKRTD AQPAVYLFQP SPDQLHTGSA SVVCLLNSFY PKDINVKWKV  180
DGVIQDTGIQ ESVTEQDKDS TYSLSSTLTM SSTEYLSHEL YSCEITHKSL PSTLIKSFQR  240
SECQRVD                                                            247

SEQ ID NO: 2            moltype = DNA  length = 744
FEATURE                 Location/Qualifiers
source                  1..744
                        mol_type = other DNA
                        note = cPD-L1_12C10E4_dK light chain of the cPD-L1 12C10E4
                         antibody
                        organism = synthetic construct
SEQUENCE: 2
atggagagcg acaccctcct gctgtgggtg ctgctactgt gggttcctgg gagcgcggga  60
gacatcgtgc tgacacagag ccctgcaagc ctggccgtga gcctgggaca gagagccacc  120
atcagctgca gagcaagcga gagcgtggag tactacggca caagcctgat gcagtggtat  180
cagcagaagc ctggacagcc tcctaagctg ctgatcttcg ccgcaagcaa cgtgaagagc  240
ggcgtgcctg ctagattcag cggcagcggc agcggcaccg acttcagcct gaacatccac  300
cctgtggagg aggacgacat cgccatgtac ttctgtcagc agagcggcaa ggtgcctcac  360
accttcggcg gcggcaccaa gctggagatc aagagatcca tggaaatcaa acgtacggat  420
gcccagccag ccgtctattt gttccaacca tctccagacc agttacacac aggaagtgcc  480
tctgttgtgt gtttgctgaa tagcttctac cccaaagaca tcaatgtcaa gtggaaagtg  540
gatggtgtca tccaagacac aggcatccag gaaagtgtca cagagcagga caaggacagt  600
acctacagcc tcagcagcac cctgacgatg tccagtactg agtacctaag tcatgagttg  660
tactcctgtg agatcactca caagagcctg ccctccaccc tcatcaagag cttccaaagg  720
```

```
agcgagtgtc agagagtgga ctaa                                          744

SEQ ID NO: 3            moltype = AA  length = 472
FEATURE                 Location/Qualifiers
source                  1..472
                        mol_type = protein
                        note = cPD-L1_12C10E4_dIgG2_heavy chain of the cPD-L1
                         12C10E4 antibody
                        organism = synthetic construct
SEQUENCE: 3
MAVLGLLFCL VTLPSCVLSQ VQLKQSGPGL VQPSQSLSIT CTISGFSLTS FGVHWVRQSP  60
GKGLEWLGVI WSGGSTDYNA AFTSRLSINK DNSKSQVFFK MNSLQADDTA IYYCARGGGP  120
DWYFDVWGTG TTVTVSSAST TAPSVFPLAP SCGSTSGSTV ALACLVSGYF PEPVTVSWNS  180
GSLTSGVHTF PSVLQSSGLY SLSSMVTVPS SRWPSETFTC NVAHPASKTK VDKPVPKREN  240
GRVPRPPDCP KCPAPEMLGG PSVFIFPPKP KDTLLIARTP EVTCVVVDLD PEDPEVQISW  300
FVDGKQMQTA KTQPREEQFN GTYRVVSVLP IGHQDWLKGK QFTCKVNNKA LPSPIERTIS  360
KARGQAHQPS VYVLPPSREE LSKNTVSLTC LIKDFFPPDI DVEWQSNGQQ EPESKYRTTP  420
PQLDEDGSYF LYSKLSVDKS RWQRGDTFIC AVMHEALHNH YTQKSLSHSP GK          472

SEQ ID NO: 4            moltype = DNA  length = 1419
FEATURE                 Location/Qualifiers
source                  1..1419
                        mol_type = other DNA
                        note = cPD-L1_12C10E4_dIgG2_heavy chain of the cPD-L1
                         12C10E4 antibody
                        organism = synthetic construct
SEQUENCE: 4
atggccgtgc tgggcctgct gttctgcctg gtgaccctgc ctagctgcgt gctgagccaa  60
gtgcagctga agcagagcgg ccctggcctg gtgcagcctt ctcagagcct gagcatcacc  120
tgcaccatca gcggcttcag cctgacaagc ttcggcgtgc actgggtgag acagagccct  180
ggcaagggcc tggagtggct gggcgtgatc tggagcggcg gcagcaccga ctacaacgcc  240
gccttcacaa gcagactgag catcaacaag gacaacagca agagccaagt gttcttcaag  300
atgaacagcc tgcaagccga cgacaccgcc atctactact gcgctagagg cggcggccct  360
gactggtact tcgacgtgtg gggcaccggc accaccgtga ccgtgagcag cgctagcacc  420
acggcccccct cggttttccc actggccccc agctgcgggt ccacttccgg ctccacggtg  480
gccctggcct gcctggtgtc aggctacttc cccgagcctg taactgtgtc ctggaattcc  540
ggctccttga ccagcggtgt gcacaccttc ccgtccgtcc tgcagtcctc agggctctac  600
tccctcagca gcatggtgac agtgccctcc agcaggtggc ccagcgagac cttcacctgc  660
aacgtggccc acccggccag caaaactaaa gtagacaagc cagtgcccaa aagagaaaat  720
ggaagagttc ctcgcccacc tgattgtccc aaatgcccag cccctgaaat gctgggaggg  780
ccttcggtct tcatctttcc cccgaaaccc aaggacaccc tcttgattgc ccgaacacct  840
gaggtcacat gtgtggtggt ggatctggac ccagaagacc ctgaggtgca gatcagctgg  900
ttcgtggacg gtaagcagat gcaaacagcc aagactcagc ctcgtgagga gcagttcaat  960
ggcacctacc gtgtggtcag tgtcctcccc attgggcacc aggactggct caaggggaag  1020
cagttcacgt gcaaagtcaa caacaaagcc ctcccatccc cgatcgagag gaccatctcc  1080
aaggccagag ggcaggccca tcaacccagt gtgtatgtcc tgccgccatc ccgggaggag  1140
ttgagcaaga acacagtcag cttgacatgc ctgatcaaag acttcttccc acctgacatt  1200
gatgtggagt ggcagagcaa tggacagcag gagcctgaga gcaagtaccg cacgaccccg  1260
ccccagctgg acgaggacgg gtcctacttc ctgtacagca agctctctgt ggacaagagc  1320
cgctggcagc ggggagacac cttcatatgt gcggtgatgc atgaagctct acacaaccac  1380
tacacacaga aatccctctc ccattctccg ggtaaatga                          1419

SEQ ID NO: 5            moltype = AA  length = 243
FEATURE                 Location/Qualifiers
source                  1..243
                        mol_type = protein
                        note = cPD-L1_3C8D3_dK_light chain of the cPD-L1 3C
                         chimeric antibody clone
                        organism = synthetic construct
SEQUENCE: 5
METHSQVFVY MLLWLSGVEG DIVMTQSHKF MSTSVGDRVS ITCKVSQDVG TAVAWYQQKP  60
GQCPKRLIYW TSTRHTGVPD RFTGSGSGTD FTLTISNVQS EDLVDYFCQQ YSSYPLTFGG  120
GTKLELKRSM EIKRTDAQPA VYLFQPSPDQ LHTGSASVVC LLNSFYPKDI NVKWKVDGVI  180
QDTGIQESVT EQDKDSTYSL SSTLTMSSTE YLSHELYSCE ITHKSLPSTL IKSFQRSECQ  240
RVD                                                                 243

SEQ ID NO: 6            moltype = DNA  length = 732
FEATURE                 Location/Qualifiers
source                  1..732
                        mol_type = other DNA
                        note = cPD-L1_3C8D3_dK_light chain of the cPD-L1 3C
                         chimeric antibody clone
                        organism = synthetic construct
SEQUENCE: 6
atggagacac attctcaggt ctttgtatac atgttgctgt ggttgtctgg tgttgaagga  60
gacattgtga tgacccagtc tcacaaattc atgtccacat cagtaggaga cagggtcagc  120
atcacctgca aggttagtca ggatgtgggt accgctgtag cctggtatca acagaaacca  180
gggcaatgtc ccaaaagact gatttactgg acatccaccc ggcacactgg agtccctgat  240
cgcttcacag gcagtggatc tgggacagat ttcactctca ccattagcaa tgtgcagtct  300
```

```
gaagacttgg tagattattt ctgtcagcaa tatagcagtt atcctctcac gttcggtggt  360
gggaccaagc tggagctgaa acggtccatg gaaatcaaac gtacggatgc ccagccagcc  420
gtctatttgt tccaaccatc tccagaccag ttacacacag gaagtgcctc tgttgtgtgt  480
ttgctgaata gcttctaccc caaagacatc aatgtcaagt ggaaagtgga tggtgtcatc  540
caagacacag gcatccagga aagtgtcaca gagcaggaca aggacagtac ctacagcctc  600
agcagcaccc tgacgatgtc cagtactgag tacctaagtc atgagttgta ctcctgtgag  660
atcactcaca agagcctgcc ctccaccctc atcaagagct tccaaaggag cgagtgtcag  720
agagtggact aa                                                       732

SEQ ID NO: 7           moltype = AA  length = 474
FEATURE                Location/Qualifiers
source                 1..474
                       mol_type = protein
                       note = cPD-L1_3C8D3_dIgG2_heavy chain of the cPD-L1 3C
                        chimeric antibody clone
                       organism = synthetic construct
SEQUENCE: 7
MGWSWIFLFL LSGTAGVLSE VQLQQSGPEL VKPGASVKMS CKASGYTFTD YVLHWVRQTN  60
GKSLEWIGEI NPSNGDTYYN QKFKGKATLT VDTSSSTAYM QLTTLTSEDS AVYYCARSDY  120
SNYVGFAYWG QGTLVTVSAA STTAPSVFPL APSCGSTSGS TVALACLVSG YFPEPVTVSW  180
NSGSLTSGVH TFPSVLQSSG LYSLSSMVTV PSSRWPSETF TCNVAHPASK TKVDKPVPKR  240
ENGRVPRPPD CPKCPAPEML GGPSVFIFPP KPKDTLLIAR TPEVTCVVVD LDPEDPEVQI  300
SWFVDGKQMQ TAKTQPREEQ FNGTYRVVSV LPIGHQDWLK GKQFTCKVNN KALPSPIERT  360
ISKARGQAHQ PSVYVLPPSR EELSKNTVSL TCLIKDFFPP DIDVEWQSNG QQEPESKYRT  420
TPPQLDEDGS YFLYSKLSVD KSRWQRGDTF ICAVMHEALH NHYTQKSLSH SPGK        474

SEQ ID NO: 8           moltype = DNA  length = 1425
FEATURE                Location/Qualifiers
source                 1..1425
                       mol_type = other DNA
                       note = cPD-L1_3C8D3_dIgG2_heavy chain of the cPD-L1 3C
                        chimeric antibody clone
                       organism = synthetic construct
SEQUENCE: 8
atgggatgga gctggatctt tctctttctc ttgtcaggaa ctgcaggtgt cctctctgaa  60
gtccagctgc aacagtctgg acctgagctg gtgaagcctg gggcttcagt gaagatgtcc  120
tgcaaggctt ctggatacac attcactgac tatgttttgc actgggtgag gcagaccaat  180
ggaaagagcc ttgagtggat tggagaaatt aatcctagca atggtgatac ttactacaac  240
cagaagttca agggcaaggc cacattgact gtagacacat cctccagcac agcctacatg  300
cagctcacca ccctgacatc tgaggactct gcagtctatt actgtgcacg atcggattat  360
agtaactacg taggatttgc ttactggggc caagggactc tggtcactgt ctctgcagct  420
agcaccacgg ccccctcggt tttcccactg gcccccagct gcgggtccac ttccggctcc  480
acggtggccc tggcctgcct ggtgtcaggc tacttccccg agcctgtaac tgtgtcctgg  540
aattccggct ccttgaccag cggtgtgcac accttcccgt ccgtcctgca gtcctcaggg  600
ctctactccc tcagcagcat ggtgacagtg ccctccagca ggtggcccag cgagaccttc  660
acctgcaacg tggcccaccc ggccagcaaa actaaagtag acaagccagt gcccaaaaga  720
gaaaatggaa gagttcctcg cccacctgat tgtcccaaat gcccagcccc tgaaatgctg  780
ggagggcctt cggtcttcat ctttcccccg aaacccaagg acaccctctt gattgcccga  840
acacctgagg tcacatgtgt ggtggtggat ctggacccag aagaccctga ggtgcagatc  900
agctggttcg tggacggtaa gcagatgcaa acagccaaga ctcagcctcg tgaggagcag  960
ttcaatggca cctaccgtgt ggtcagtgtc ctccccattg ggcaccagga ctggctcaag  1020
gggaagcagt tcacgtgcaa agtcaacaac aaagccctcc catccccgat cgagaggacc  1080
atctccaagg ccagagggca ggcccatcaa cccagtgtgt atgtcctgcc gccatcccgg  1140
gaggagttga gcaagaacac agtcagcttg acatgcctga tcaaagactt cttcccacct  1200
gacattgatg tggagtggca gagcaatgga cagcaggagc ctgagagcaa gtaccgcacg  1260
accccgcccc agctggacga ggacgggtcc tacttcctgt acagcaagct ctctgtggac  1320
aagagccgct ggcagcgggg agacaccttc atatgtgcgg tgatgcatga agctctacac  1380
aaccactaca cacagaaatc cctctcccat tctccgggta aatga                  1425

SEQ ID NO: 9           moltype = AA  length = 10
FEATURE                Location/Qualifiers
source                 1..10
                       mol_type = protein
                       note = a CDR1
                       organism = synthetic construct
SEQUENCE: 9
ESVEYYGTSL                                                          10

SEQ ID NO: 10          moltype = AA  length = 11
FEATURE                Location/Qualifiers
source                 1..11
                       mol_type = protein
                       note = a CDR3
                       organism = synthetic construct
SEQUENCE: 10
CQQSGKVPHT F                                                        11

SEQ ID NO: 11          moltype = AA  length = 12
FEATURE                Location/Qualifiers
```

-continued

```
source                  1..12
                        mol_type = protein
                        note = a CDR3
                        organism = synthetic construct
SEQUENCE: 11
ARGGGPDWYF DV                                                       12

SEQ ID NO: 12           moltype = AA  length = 11
FEATURE                 Location/Qualifiers
source                  1..11
                        mol_type = protein
                        note = a CDR3
                        organism = synthetic construct
SEQUENCE: 12
CQQYSSYPLT F                                                        11

SEQ ID NO: 13           moltype = AA  length = 15
FEATURE                 Location/Qualifiers
source                  1..15
                        mol_type = protein
                        note = a CDR3
                        organism = synthetic construct
SEQUENCE: 13
CARSDYSNYV GFAYW                                                    15

SEQ ID NO: 14           moltype = AA  length = 20
FEATURE                 Location/Qualifiers
source                  1..20
                        mol_type = protein
                        note = a portion of the sequence for a cPD-L1 12C chi
                         antibody clone
                        organism = synthetic construct
SEQUENCE: 14
GDTFICAVMH EALHNHYTQK                                               20

SEQ ID NO: 15           moltype = AA  length = 8
FEATURE                 Location/Qualifiers
source                  1..8
                        mol_type = protein
                        note = a CDR1
                        organism = synthetic construct
SEQUENCE: 15
GFSLTSFG                                                            8

SEQ ID NO: 16           moltype = AA  length = 7
FEATURE                 Location/Qualifiers
source                  1..7
                        mol_type = protein
                        note = a CDR2
                        organism = synthetic construct
SEQUENCE: 16
IWSGGST                                                             7

SEQ ID NO: 17           moltype = AA  length = 6
FEATURE                 Location/Qualifiers
source                  1..6
                        mol_type = protein
                        note = a CDR1
                        organism = synthetic construct
SEQUENCE: 17
QDVGTA                                                              6

SEQ ID NO: 18           moltype = AA  length = 8
FEATURE                 Location/Qualifiers
source                  1..8
                        mol_type = protein
                        note = a CDR1
                        organism = synthetic construct
SEQUENCE: 18
GYTFTDYV                                                            8

SEQ ID NO: 19           moltype = AA  length = 8
FEATURE                 Location/Qualifiers
source                  1..8
                        mol_type = protein
                        note = a CDR2
                        organism = synthetic construct
SEQUENCE: 19
INPSNGDT                                                            8
```

```
SEQ ID NO: 20          moltype = RNA  length = 23
FEATURE                Location/Qualifiers
source                 1..23
                       mol_type = other RNA
                       note = pre-assembled guide RNA related to full length of
                        canine CD274 cDNA (NM_001291972)
                       organism = synthetic construct
SEQUENCE: 20
cagcaaatat cctcatgttt tgg                                          23

SEQ ID NO: 21          moltype = RNA  length = 20
FEATURE                Location/Qualifiers
source                 1..20
                       mol_type = other RNA
                       note = forward primer of primer set 1
                       organism = synthetic construct
SEQUENCE: 21
ccacttggtt ctacatggct                                              20

SEQ ID NO: 22          moltype = RNA  length = 21
FEATURE                Location/Qualifiers
source                 1..21
                       mol_type = other RNA
                       note = reverse primer of primer set 1
                       organism = synthetic construct
SEQUENCE: 22
cctcagcctg acacattagt t                                            21

SEQ ID NO: 23          moltype = RNA  length = 21
FEATURE                Location/Qualifiers
source                 1..21
                       mol_type = other RNA
                       note = forward primer of primer set 2
                       organism = synthetic construct
SEQUENCE: 23
cctgtcacct ctgaacatga a                                            21

SEQ ID NO: 24          moltype = RNA  length = 21
FEATURE                Location/Qualifiers
source                 1..21
                       mol_type = other RNA
                       note = reverse primer of primer set 2
                       organism = synthetic construct
SEQUENCE: 24
ggactaagct ctaggttgtc c                                            21

SEQ ID NO: 25          moltype = RNA  length = 22
FEATURE                Location/Qualifiers
source                 1..22
                       mol_type = other RNA
                       note = forward primer of primer set 3
                       organism = synthetic construct
SEQUENCE: 25
gactggcttt tagggcttat gt                                           22

SEQ ID NO: 26          moltype = RNA  length = 23
FEATURE                Location/Qualifiers
source                 1..23
                       mol_type = other RNA
                       note = reverse primer of primer set 3
                       organism = synthetic construct
SEQUENCE: 26
acaccccaca aattacttcc att                                          23

SEQ ID NO: 27          moltype = AA  length = 243
FEATURE                Location/Qualifiers
source                 1..243
                       mol_type = protein
                       organism = synthetic construct
SEQUENCE: 27
MESDTLLLWV LLLWVPGSAG DIVLTQSPAS LAVSLGQRAT ISCRASESVE YYGTSLMQWY  60
QQKPGQPPKL LIFAASNVKS GVPARFSGSG SGTDFSLNIH PVEEDDIAMY FCQQSGKVPH  120
TFGGGTKLEI KRSMADAQPA VYLFQPSPDQ LHTGSASVVC LLNSFYPKDI NVKWKVDGVI  180
QDTGIQESVT EQDKDSTYSL SSTLTMSSTE YLSHELYSCE ITHKSLPSTL IKSFQRSECQ  240
RVD                                                                243

SEQ ID NO: 28          moltype = DNA  length = 729
FEATURE                Location/Qualifiers
```

-continued

```
source               1..729
                     mol_type = other DNA
                     organism = synthetic construct
SEQUENCE: 28
atggaaagtg atactctact actatgggtg ctcctgctgt gggtccctgg ctctgctggc  60
gatatcgtgc tgacccagtc ccccgcctct ctggccgtgt ccttgggcca gcgcgctaca  120
atttcctgca gagcctccga gagcgtggaa tactacggca cctctctgat gcagtggtac  180
cagcagaagc ctggacaacc tcctaagctg ctgatcttcg ccgcttctaa tgtcaaatct  240
ggcgtgccag ccagattctc cggcagcgga tccggcaccg actttagcct gaacatccac  300
cctgtggaag aggacgacat cgccatgtac ttctgccagc agtctggcaa agtgcctcat  360
accttcggcg gcggaaccaa gctggaaatc aagcggtcca tggccgatgc tcagcctgct  420
gtgtacctgt tccagccctc ccctgaccag ctgcacaccg gctctgcctc tgtggtgtgc  480
ctgctgaact ccttctaccc caaggacatc aacgtgaagt ggaaggtgga cggcgtgatc  540
caggacaccg gcatccaaga gtccgtgacc gagcaggaca aggactccac ctactccctg  600
tcctctaccc tgaccatgtc ctccacagaa tatctgtctc acgagctgta cagctgcgag  660
atcacccaca agagcctgcc ttctacactg atcaagtcct ttcagcggtc tgagtgtcag  720
agagtggat                                                          729

SEQ ID NO: 29        moltype = DNA  length = 1416
FEATURE              Location/Qualifiers
source               1..1416
                     mol_type = other DNA
                     organism = synthetic construct
SEQUENCE: 29
atggcagtgc taggtctact atttgcccta gtcactctgc cctcctgcgt gctgtcccag  60
gtacagctca agcagtctgg acctggcctg gtgcagccca gccagtctct gtccatcacc  120
tgtacaattt ccggcttctc gctgacatcc ttcggcgtgc actgggtgcg gcagtctccc  180
ggcaagggct tggagtggct gggcgtgatc tggtccggcg gctccaccga ctacaacgcc  240
gctttcacat ctcgcctgtc tatcaacaag gataactcta agtcccaagt gttcttcaag  300
atgaactccc tgcaggctga cgacaccgcc atctactact gcgctcgggg aggcggccct  360
gattggtact tcgacgtgtg gggcaccgga acaaccgtta ctgtgtcctc tgcctccacc  420
accgctcctt ccgtgttccc tctggcccct tcttgcggct ctacctccgg gtctacagtg  480
gctctggcct gcctggtgtc cggctacttt cctgaacccg tgaccgtgtc ctggaactcc  540
ggctctctga cctctggcgt gcacaccttc ccctccgtgc tgcagtccag cggcctgtat  600
tccctctcca gcatggtcac cgtgcccagc tccagatggc ctagcgaaac ctttacctgc  660
aacgtggccc atcctgcctc taaaaccaag gtggataagc ctgtgccaaa gagagagaat  720
ggcagagtgc ctaggcctcc tgactgcccc aagtgtcctg ctcctgagat gctgggcgga  780
ccctccgtgt ttatcttccc tcctaaacct aaggataccc tgctgatcgc cagaacccca  840
gaagtcacct gtgtggtggt ggacctggat cctgaggacc ctgaggtgca gatctcttgg  900
ttcgtggacg gcaagcagat gcagaccgcc aagacccagc ctcgggaaga gcagttcaac  960
ggcacctaca gagtggtctc tgtgctgcct atcggccacc aggactggct gaaaggcaaa  1020
cagttcacct gcaaggtgaa caacaaggcc ctgccttctc ccatcgagag aaccatctct  1080
aaggctagag gccaggctca tcaacctagt gtgtacgtgc tgccaccttc cagagaggaa  1140
ctgagcaaga acaccgtgtc gctcacctgt ctgatcaagg acttctttcc acctgacatc  1200
gacgtggaat ggcagtccaa tggccagcaa gagcctgagt ccaagtaccg gaccacccct  1260
cctcagctgg acgaggatgg ctcctacttc ctgtactcca agctgagcgt ggacaagtcc  1320
cggtggcagc ggggcgacac attcatctgc gccgtgatgc acgaggccct gcacaaccac  1380
tacacccaga agtctctgag tcactctcca ggaaaa                            1416
```

CANINE PD-L1 ANTIBODY, ANTIGEN BINDING FRAGMENTS THEREOF, AND METHODS OF USE THEREOF

PRIORITY

This patent application is a continuation-in-part of International Application Serial No. PCT/US2023/079712, filed Nov. 14, 2023, which claims the priority benefit of U.S. Provisional Patent Application No. 63/383,909 filed Nov. 15, 2022. The content of each of the foregoing applications is hereby incorporated by reference in its entirety into this disclosure.

SEQUENCE LISTING

The following application contains a sequence listing filed electronically as a Standard ST.26 compliant XML file entitled "ABC-081USCIP.xml," created on Apr. 30, 2025, as 39,555 bytes in size, the entire contents of which are incorporated by reference herein.

TECHNICAL FIELD

This disclosure relates to anti-canine programmed death-ligand 1 (PD-L1) antibodies, antigen binding fragments thereof, complementarity determining regions (CDRs) thereof, and caninized antibodies against canine PD-L1. Methods of predicting and modeling anti-cancer activity of a test compound in a subject using the antibodies, CDRs, and/or antigen binding fragments thereof are also provided.

BACKGROUND

In a normal healthy system, immune checkpoints are surface proteins that are present to check and thwart any overstimulation of immune response. In other words, their role is to prevent an immune response from being so strong that it destroys healthy cells in the body. In the case of cancer, when a T cell checkpoint protein (e.g., programmed cell death protein 1 (PD-1)) engages with its binding protein on a tumor cell (programmed death-ligand 1 (PD-L1)), it sends an "off" signal to the T cells and suppresses the anti-tumor immune response. In this manner, tumor killer cells within the immune system cannot kill the tumor because their method of attack is blocked by those checkpoints on the tumor itself.

Immune checkpoint blockade therapy employs immune checkpoint inhibitors and functions by inhibiting the checkpoint proteins from binding with their ligands on tumor cells. PD-1, cytotoxic T-lymphocyte-associated protein 4 (CTLA-4), lymphocyte activating 3 (LAG3), T cell immunoglobulin and mucin domain-containing protein 3 (TIM3), T cell immunoreceptor with Ig and ITIM domains (TIGIT) and V-domain Ig suppressor of T cell activation (VISTA) are some of the examples of checkpoint proteins. Immune checkpoint blockade therapy is one of the most promising forms of cancer immunotherapy and has been successful in multiple cancer types, including invasive urinary bladder cancer. In particular, the PD-1/PD-L1 pathway blockade using anti-PD-1 or anti-PD-L1 antibodies has elicited durable clinical responses in cancer patients, for example, by normalizing the imbalanced anti-tumor immunity.

Given the promising and durable clinical responses, the U.S. Food and Drug Administration (FDA) has approved three PD-1 antibodies (Pembrolizumab (Keytruda®) and Nivolumab (Opdivo®), and cemiplimab) and three PD-L1 antibodies (atezolizumab, avelumab, and durvalumab) for multiple types of cancer in humans. While this milestone suggests the promise of cancer immunotherapy treatment, PD-1/PD-L1 blockade therapy in cancer is not satisfactory at present due to the limited response rates (10-40%). Therefore, new immunotherapeutic strategies to improve the therapeutic efficacy of the current PD-1/PD-L1 blockade are urgently needed.

Strategies to improve PD-1/PD-L1 blockade therapies in bladder and other cancers can include 1) identifying host factors including genetics, immune state, and molecular subtype that drive response, 2) assessing biomarkers and combinations of biomarkers to predict response and personalize therapy, 3) developing better tools to monitor immune effects, and 4) selecting combination drug approaches/regimens to address multiple "defects" in the immune response in addition to PD-1/PD-L1 blockade. Relevant pre-clinical animal models are typically used to develop these strategies and test combination approaches. Factors that are likely to affect the PD-1/PD-L1 axis and, thus, factors that can be represented in animal models, include aggressive and metastatic cancer behavior, tumor heterogeneity, mutational landscape, genetic and epigenetic crosstalk, cancer molecular subtypes, immune cell responsiveness, and innate and acquired mechanisms of drug resistance. While rodent models, including carcinogen-induced, engraftment, and genetically engineered models, are instrumental in cancer research, rodent models do not possess the collective features that are critical to studying emerging therapies within and across molecular subtypes in bladder cancer, and predicting therapeutic success or failure in humans. What is needed is an animal model that can be used to optimize checkpoint inhibitor treatment in humans.

In addition, many rodent data are not predictive for canines, especially with respect to immune checkpoint blockade therapy. Many cancers remain untreatable in canines, and therapeutic approaches effective for one cancer often fail in another. Thus, there is also a need to treat certain forms of cancer in canines.

SUMMARY

A caninized antibody or antigen binding fragment thereof that binds canine programmed death ligand 1 (PD-L1) in a canine subject is provided. The antibody or antigen binding fragment binds canine programmed death ligand 1 (PD-L1) in a canine subject with specificity. The antibody or antigen binding fragment comprises a light chain and a heavy chain, wherein the light chain comprises the following amino acid sequence:

(SEQ ID NO: 27)

```
MESDTLLLWVLLLWVPGSAGDIVLTQSPASLAVSLGQRATISCRA
SESVEYYGTSLMQWYQQKPGQPPKLLIFAASNVKSGVPARFSGSG
SGTDFSLNIHPVEEDDIAMYFCQQSGKVPHTFGGGTKLEIKRSMA
DAQPAVYLFQPSPDQLHTGSASVVCLLNSFYPKDINVKWKVDGVI
QDTGIQESVTEQDKDSTYSLSSTLTMSSTEYLSHELYSCEITHKS
LPSTLIKSFQRSECQRVD
```

The antibody or antigen binding fragment comprises a light chain and a heavy chain, wherein the heavy chain comprises the following amino acid sequence:

(SEQ ID NO: 3)

MAVLGLLFCLVTLPSCVLSQVQLKQSGPGLVQPSQSLSITCTISG

FSLTSFGVHWVRQSPGKGLEWLGVIWSGGSTDYNAAFTSRLSINK

DNSKSQVFFKMNSLQADDTAIYYCARGGGPDWYFDVWGTGTTVTV

SSASTTAPSVFPLAPSCGSTSGSTVALACLVSGYFPEPVTVSWNS

GSLTSGVHTFPSVLQSSGLYSLSSMVTVPSSRWPSETFTCNVAHP

ASKTKVDKPVPKRENGRVPRPPDCPKCPAPEMLGGPSVFIFPPKP

KDTLLIARTPEVTCVVVDLDPEDPEVQISWFVDGKQMQTAKTQPR

EEQFNGTYRVVSVLPIGHQDWLKGKQFTCKVNNKALPSPIERTIS

KARGQAHQPSVYVLPPSREELSKNTVSLTCLIKDFFPPDIDVEWQ

SNGQQEPESKYRTTPPQLDEDGSYFLYSKLSVDKSRWQRGDTFIC

AVMHEALHNHYTQKSLSHSPGK

In certain embodiments, the antibody or antigen binding fragment is encoded by the amino acid sequence comprising at least 90% sequence identity to SEQ ID NO: 27 and/or SEQ ID NO: 3. In still further embodiments, the antibody or antigen binding fragment is encoded by the amino acid sequence comprising at least 95% sequence identity to SEQ ID NO: 27 and/or SEQ ID NO: 3, or at least 97% or more sequence identity to SEQ ID NO: 27 and/or SEQ ID NO: 3.

A caninized antibody or antigen binding fragment thereof that binds canine programmed death ligand 1 (PD-L1) in a canine subject is provided. The antibody or antigen binding fragment binds canine programmed death ligand 1 (PD-L1) in a canine subject with specificity. The antibody or antigen binding fragment comprises a light chain and a heavy chain, wherein the light chain is encoded by the nucleotide sequence comprising:

(SEQ ID NO: 28)

ATGGAAAGTGATACTCTACTACTATGGGTGCTCCTGCTGTGGGTC

CCTGGCTCTGCTGGCGATATCGTGCTGACCCAGTCCCCCGCCTCT

CTGGCCGTGTCCTTGGGCCAGCGCGCTACAATTTCCTGCAGAGCC

TCCGAGAGCGTGGAATACTACGGCACCTCTCTGATGCAGTGGTAC

CAGCAGAAGCCTGGACAACCTCCTAAGCTGCTGATCTTCGCCGCT

TCTAATGTCAAATCTGGCGTGCCAGCCAGATTCTCCGGCAGCGGA

TCCGGCACCGACTTTAGCCTGAACATCCACCCTGTGGAAGAGGAC

GACATCGCCATGTACTTCTGCCAGCAGTCTGGCAAAGTGCCTCAT

ACCTTCGGCGGCGGAACCAAGCTGGAAATCAAGCGGTCCATGGCC

GATGCTCAGCCTGCTGTGTACCTGTTCCAGCCCTCCCCTGACCAG

CTGCACACCGGCTCTGCCTCTGTGGTGTGCCTGCTGAACTCCTTC

TACCCCAAGGACATCAACGTGAAGTGGAAGGTGGACGGCGTGATC

CAGGACACCGGCATCCAAGAGTCCGTGACCGAGCAGGACAAGGAC

TCCACCTACTCCCTGTCCTCTACCCTGACCATGTCCTCCACAGAA

TATCTGTCTCACGAGCTGTACAGCTGCGAGATCACCCACAAGAGC

CTGCCTTCTACACTGATCAAGTCCTTTCAGCGGTCTGAGTGTCAG

AGAGTGGAT

The antibody or antigen binding fragment comprises a light chain and a heavy chain, wherein the heavy chain is encoded by the nucleotide sequence comprising:

(SEQ ID NO: 29)

ATGGCAGTGCTAGGTCTACTATTTTGCCTAGTCACTCTGCCCTCC

TGCGTGCTGTCCCAGGTACAGCTCAAGCAGTCTGGACCTGGCCTG

GTGCAGCCCAGCCAGTCTCTGTCCATCACCTGTACAATTTCCGGC

TTCTCGCTGACATCCTTCGGCGTGCACTGGGTGCGGCAGTCTCCC

GGCAAGGGCTTGGAGTGGCTGGGCGTGATCTGGTCCGGCGGCTCC

ACCGACTACAACGCCGCTTTCACATCTCGCCTGTCTATCAACAAG

GATAACTCTAAGTCCCAAGTGTTCTTCAAGATGAACTCCCTGCAG

GCTGACGACACCGCCATCTACTACTGCGCTCGGGGAGGCGGCCCT

GATTGGTACTTCGACGTGTGGGGCACCGGAACAACCGTTACTGTG

TCCTCTGCCTCCACCACCGCTCCTTCCGTGTTCCCTCTGGCCCCT

TCTTGCGGCTCTACCTCCGGGTCTACAGTGGCTCTGGCCTGCCTG

GTGTCCGGCTACTTTCCTGAACCCGTGACCGTGTCCTGGAACTCC

GGCTCTCTGACCTCTGGCGTGCACACCTTCCCCTCCGTGCTGCAG

TCCAGCGGCCTGTATTCCCTCTCCAGCATGGTCACCGTGCCCAGC

TCCAGATGGCCTAGCGAAACCTTTACCTGCAACGTGGCCCATCCT

GCCTCTAAAACCAAGGTGGATAAGCCTGTGCCAAAGAGAGAGAAT

GGCAGAGTGCCTAGGCCTCCTGACTGCCCCAAGTGTCCTGCTCCT

GAGATGCTGGGCGGACCCTCCGTGTTTATCTTCCCTCCTAAACCT

AAGGATACCCTGCTGATCGCCAGAACCCCAGAAGTCACCTGTGTG

GTGGTGGACCTGGATCCTGAGGACCCTGAGGTGCAGATCTCTTGG

TTCGTGGACGGCAAGCAGATGCAGACCGCCAAGACCCAGCCTCGG

GAAGAGCAGTTCAACGGCACCTACAGAGTGGTCTCTGTGCTGCCT

ATCGGCCACCAGGACTGGCTGAAAGGCAAACAGTTCACCTGCAAG

GTGAACAACAAGGCCCTGCCTTCTCCCATCGAGAGAACCATCTCT

AAGGCTAGAGGCCAGGCTCATCAACCTAGTGTGTACGTGCTGCCA

CCTTCCAGAGAGGAACTGAGCAAGAACACCGTGTCGCTCACCTGT

CTGATCAAGGACTTCTTTCCACCTGACATCGACGTGGAATGGCAG

TCCAATGGCCAGCAAGAGCCTGAGTCCAAGTACCGGACCACCCCT

CCTCAGCTGGACGAGGATGGCTCCTACTTCCTGTACTCCAAGCTG

AGCGTGGACAAGTCCCGGTGGCAGCGGGGCGACACATTCATCTGC

GCCGTGATGCACGAGGCCCTGCACAACCACTACACCCAGAAGTCT

CTGAGTCACTCTCCAGGAAAA

In certain embodiments, the antibody or antigen binding fragment is encoded by the nucleotide sequence comprising at least 80% sequence identity to SEQ ID NO: 28 and/or SEQ ID NO: 29.

The antibody or antigen binding fragment can comprise one or more complementarity determining regions (CDRs) comprising AAS, SEQ ID NO: 9, and/or SEQ ID NO: 10. The antibody or antigen binding fragment can comprise CDRs independently comprising at least 90% sequence identity to AAS, SEQ ID NO: 9, and/or SEQ ID NO: 10. The antibody or antigen binding fragment can comprise CDRs independently comprising at least 95% sequence identity to AAS, SEQ ID NO: 9, and/or SEQ ID NO: 10, or at least 97% or more sequence identity to AAS, SEQ ID NO: 9, and/or SEQ ID NO: 10. The antibody or antigen binding fragment can comprise one or more complementarity determining regions (CDRs) comprising SEQ ID NO: 15, SEQ ID NO: 16, and/or SEQ ID NO: 11. The antibody or antigen binding fragment can comprise CDRs independently comprising at least 90% sequence identity to SEQ ID NO: 15, SEQ ID NO: 16, and/or SEQ ID NO: 11 (e.g., comprising SEQ ID NO: 15, SEQ ID NO: 16, and/or SEQ ID NO: 11). The antibody or antigen binding fragment can comprise CDRs independently comprising at least 95% sequence identity to SEQ ID NO: 15, SEQ ID NO: 16, and/or SEQ ID NO: 11, or at least 97% or more sequence identity to SEQ ID NO: 15, SEQ ID NO: 16, and/or SEQ ID NO: 11.

In certain embodiments, the antibody or antigen binding fragment is completely or incompletely caninized.

The antibody or antigen binding fragment can be a chimeric form of a caninized antibody or antigen binding fragment. The antibody or antigen binding fragment thereof can, in certain embodiments, bind canine PD-L1 with specificity. In certain embodiments, the antibody or antigen binding fragment comprises a caninized murine PD-1 antibody or antigen binding fragment thereof.

Methods for treating cancer in a canine subject are also provided. Such a method can comprise administering to a canine subject a therapeutically effective amount of a caninized antibody or antigen binding fragment thereof that binds canine PD-L1 and inhibits a PD-L1/PD-1 interaction in the subject.

The caninized antibody or antigen binding fragment thereof of the method can comprise any of the caninized antibodies or antigen binding fragments thereof described herein. In certain embodiments, for example, the caninized antibody or antigen binding fragment thereof comprises an amino acid sequence comprising at least 90% sequence identity to SEQ ID NO: 27 and/or SEQ ID NO: 3. In embodiments, the antibody or antigen binding fragment is encoded by the amino acid sequence comprising at least 95% sequence identity to SEQ ID NO: 27 and/or SEQ ID NO: 3, or at least 97% or more sequence identity to SEQ ID NO: 27 and/or SEQ ID NO: 3. The caninized antibody or antigen binding fragment can comprise one or more CDRs independently comprising at least 90% sequence identity to AAS, SEQ ID NO: 9, and/or SEQ ID NO: 10. In embodiments, the antibody or antigen binding fragment can comprise one or more CDRs independently comprising at least 95% sequence identity to AAS, SEQ ID NO: 9, and/or SEQ ID NO: 10, or at least 97% or more sequence identity to AAS, SEQ ID NO: 9, and/or SEQ ID NO: 10. The caninized antibody or antigen binding fragment can comprise one or more CDRs independently comprising at least 90% sequence identity to SEQ ID NO: 15, SEQ ID NO: 16 and/or SEQ ID NO: 11. In embodiments, the antibody or antigen binding fragment can comprise one or more CDRs independently comprising at least 95% sequence identity to SEQ ID NO: 15, SEQ ID NO: 16 and/or SEQ ID NO: 11, or at least 97% or more sequence identity to SEQ ID NO: 15, SEQ ID NO: 16 and/or SEQ ID NO: 11.

In certain embodiments of the method, the caninized antibody or antigen binding fragment thereof comprises the amino acid sequence comprising SEQ ID NO: 27 and/or SEQ ID NO: 3.

In certain embodiments, the therapeutically effective amount is from about 2 mg/kg of subject body weight (such as, for example, 2 mg/kg of subject body weight) to about 5 mg/kg of subject body weight (such as, for example, 5 mg/kg of subject body weight). The therapeutically effective amount can be 2 mg/kg of subject body weight. The therapeutically effective amount can be 5 mg/kg of subject body weight. The therapeutically effective amount can be from about 2.5 mg/kg of subject body weight (such as, for example, 2.5 mg/kg of subject body weight) to about 4.5 mg/kg of subject body weight (such as, for example, 4.5 mg/kg of subject body weight). The therapeutically effective amount can be from about 3.0 mg/kg of subject body weight (such as, for example, 3.0 mg/kg of subject body weight) to about 4.0 mg/kg of subject body weight (such as, for example, 4.0 mg/kg of subject body weight). The therapeutically effective amount can be from about 2.5 mg/kg of subject body weight (such as, for example, 3.0 mg/kg of subject body weight) to about 3.5 mg/kg of subject body weight (such as, for example, 3.5 mg/kg of subject body weight). The therapeutically effective amount can be 2 mg/kg of subject body weight. The therapeutically effective amount can be 5 mg/kg of subject body weight. The therapeutically effective amount can be from about 5.0 mg/kg of subject body weight (such as, for example, 5.0 mg/kg of subject body weight) to about 10.0 mg/kg of subject body weight (such as, for example, 10.0 mg/kg of subject body weight). The therapeutically effective amount can be from about 5.5 mg/kg of subject body weight (such as, for example, 5.5 mg/kg of subject body weight) to about 9.5 mg/kg of subject body weight (such as, for example, 9.5 mg/kg of subject body weight). The therapeutically effective amount can be from about 6.0 mg/kg of subject body weight (such as, for example, 6.0 mg/kg of subject body weight) to about 9.0 mg/kg of subject body weight (such as, for example, 9.0 mg/kg of subject body weight). The therapeutically effective amount can be from about 6.5 mg/kg of subject body weight (such as, for example, 6.5 mg/kg of subject body weight) to about 8.5 mg/kg of subject body weight (such as, for example, 8.5 mg/kg of subject body weight). The therapeutically effective amount can be from about 7.0 mg/kg of subject body weight (such as, for example, 7.0 mg/kg of subject body weight) to about 8.0 mg/kg of subject body weight (such as, for example, 8.0 mg/kg of subject body weight). The therapeutically effective amount can be from about 7.5 mg/kg of subject body weight (such as, for example, 7.5 mg/kg of subject body weight) to about 7.8 mg/kg of subject body weight (such as, for example, 7.8 mg/kg of subject body weight). The ranges specified in this paragraph are inclusive of the end points stated and all 0.1 mg/kg increments contained within the specified ranges.

The cancer can be invasive urothelial carcinoma.

In certain embodiments of the method, the antibody or antigen binding fragment thereof is formulated into a pharmaceutical composition.

Pharmaceutical compositions are also provided. In certain embodiments, the pharmaceutical composition comprises any of the caninized antibodies or antigen binding fragments thereof described herein and a pharmaceutically acceptable excipient.

In certain embodiments, the set of test compounds comprises at least a compound that inhibits PD-L1/PD-1 interaction in the subject.

In certain embodiments, a use of a caninized antibody or antigen binding fragment of the present disclosure, a pharmaceutical composition described herein, or one or more of the CDRs described herein is provided, such use in the preparation of a medicament for treating cancer in a canine subject.

The disclosed embodiments and other features, advantages, and aspects contained herein, and the matter of attaining them, will become apparent in light of the following detailed description of various exemplary embodiments of the present disclosure.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 4B showing a sodium dodecyl sulfate-polyacrylamide gel electrophoresis (SDS-PAGE) analysis of 12C chimeric antibody purity under nonreducing and reducing (2-mercaptoethanol) conditions (HC, heavy chain; LC, light chain; SM, protein size marker); FIG. 4C showing an isoelectric focusing (IEF) analysis of 12C chimeric antibody (standard, pI standard); FIG. 4D showing peptide mapping analysis of the cPD-L1 12C chimeric antibody (SEQ ID NO: 14); the 12C chimeric antibody was enzymatically digested with trypsin on S-trap micro columns from Protifi after reduction and alkylation. Peptides were then separated and analyzed by reversed-phase liquid chromatography tandem mass spectrometry (RP-LC/MS-MS). The resultant mass spectrometric data were analyzed using the PEAK PTM workflow int eh PEAKS X PRO Studio 10.6 software package from Bioinformatics Solutions Inc. to map the detected MS1 and MS2 ions to the amino acid sequence of the antibody. The sequence coverage of heavy and light chains was 100% (453 of 453 amino acids) and 98.2% (223 of 227 amino acids), respectively); FIG. 4E showing size exclusion chromatography (SEC) analysis of 12C chimeric antibody (standard, SEC standard); and FIG. 4F showing a matrix-assisted laser desorption/ionization (MALDI)-mass spectrometry (MS) profile of permethylated N-glycans released from PNGase F-treated 12C chimeric antibody, with the masses of indicated glycan species representing the [M+Na+] values.

FIG. 5C shows 12C chimeric antibody binding to cPD-L1 and cPD-L2.

FIG. 5D shows a binding affinity ($K_D$) analysis of 12C chimeric antibody by Octet.

Figure 1:
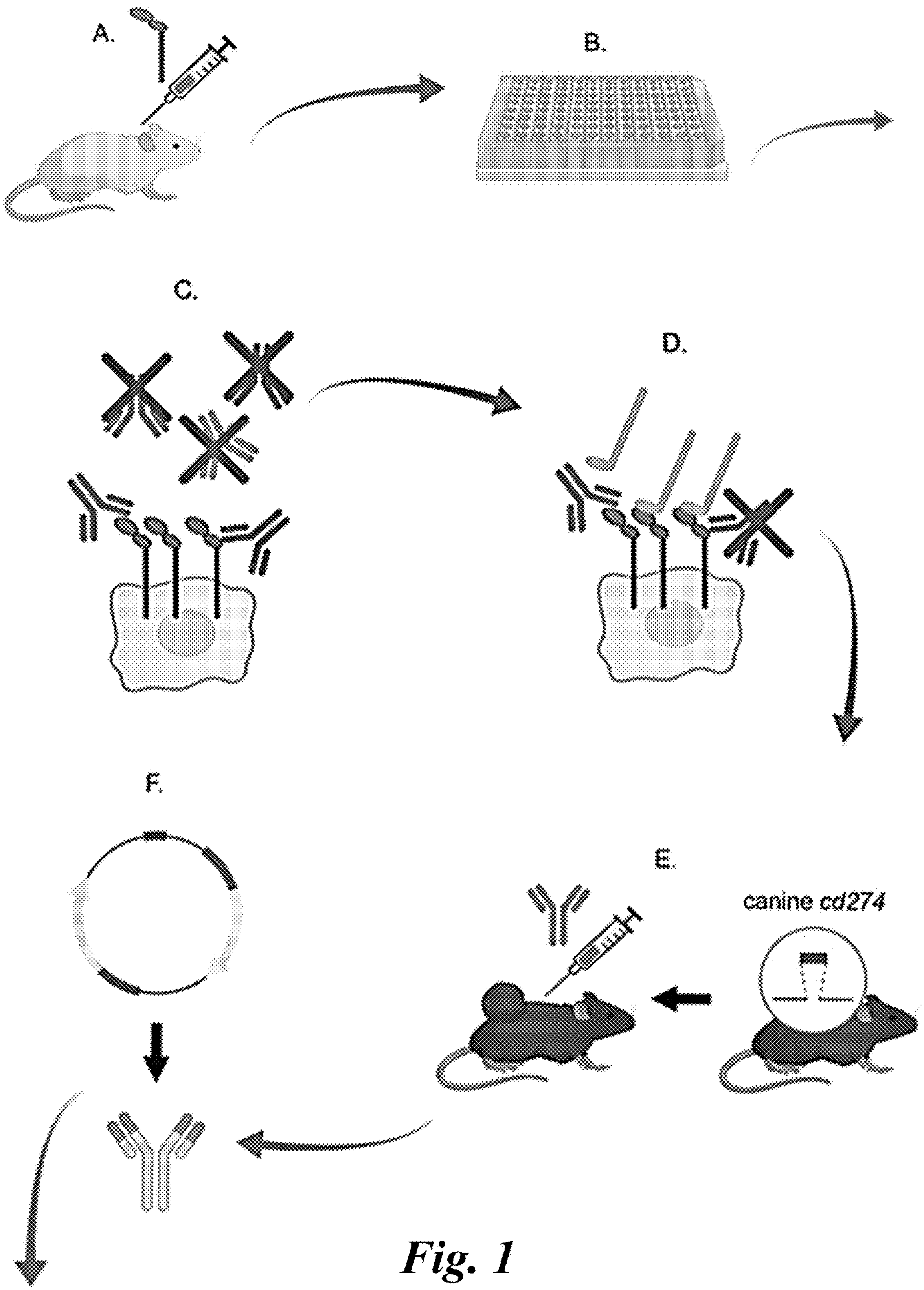
FIG. 1 shows a schematic flow chart representing the production and validation of canine PD-L1 antibody used herein, with (A) Immunization of antigen, canine PD-L1 protein (cPD-L1) injection. (B) Establishment of hybridomas (over 2.000 clones). (C) cPD-L1 specific antibody (Ab) selection by the live cell-based Ab binding assay. (D) Therapeutic Ab selection by cPD-1/PD-L1 blockade assay. (E) In vivo validation of therapeutic efficacy of cPD-L1 antibodies in the mice that have only canine PD-L1 (i.e. caninized PD-L1 mice) and PD-1. (F) Production of the cPD-L1 chimeric Ab (mouse/canine). (G) Validation of the cPD-L1 chimeric Ab, and (H) Initial safety profile and a PK assay in dog.
Figure 1:
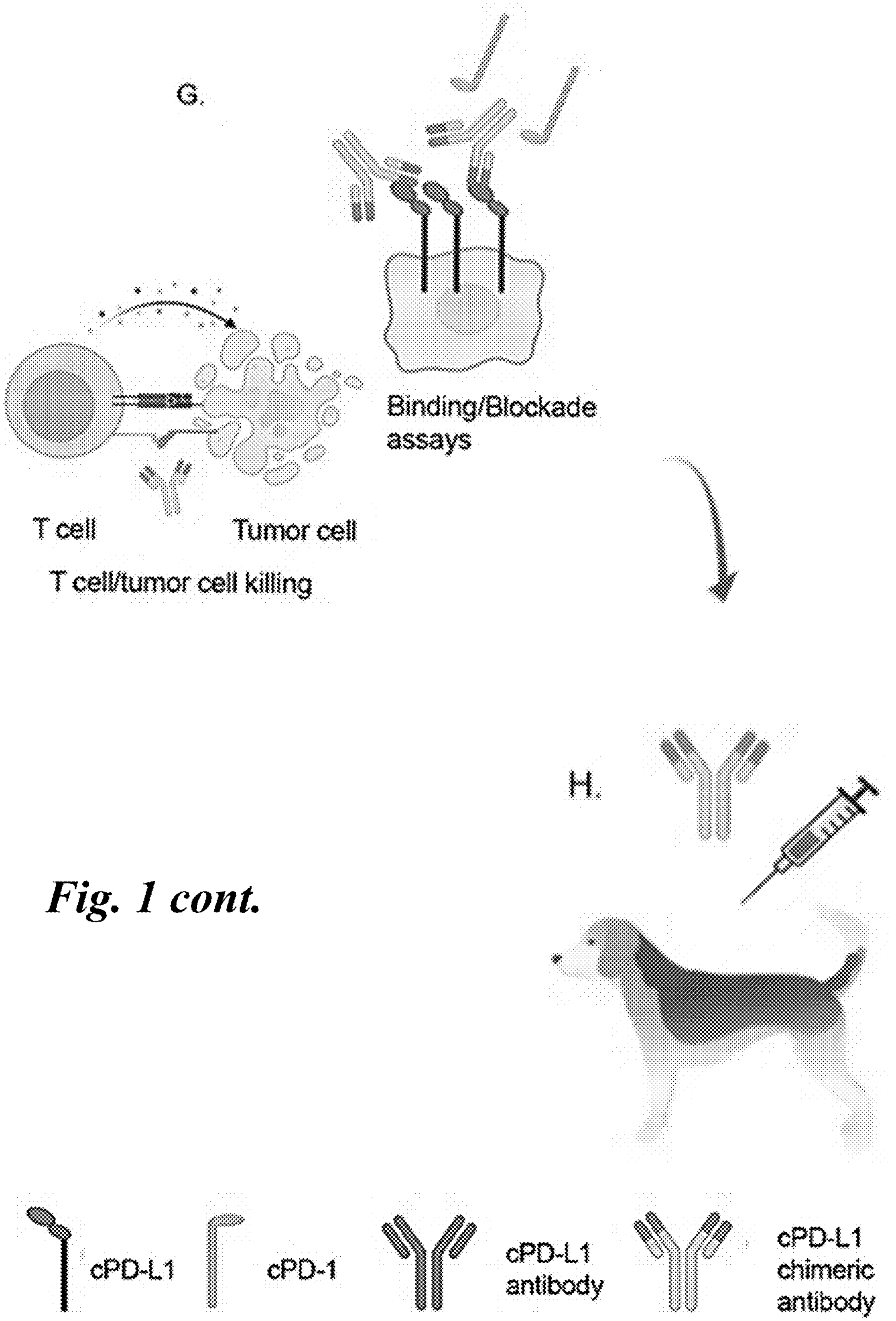

While the present disclosure is susceptible to various modifications and alternative forms, exemplary embodiments thereof are shown by way of example in the drawings and are herein described in detail.

SEQUENCES

The sequences herein (SEQ ID NOS: 1-29) are also provided in computer readable form encoded in a file filed herewith and incorporated herein by reference. The information recorded in computer readable form is identical to the written sequence listings provided herein, pursuant to 37 C.F.R. § 1.821 (f).

SEQ ID NO: 1 is the amino acid sequence for the cPD-L1 12C10E4 kappa light chain of the cPD-L1 12C10E4 antibody (deduced from the DNA sequence):

MESDTLLLWVLLLWVPGSAG*DIVLTQSPASLAVSLGQRATISCRA*

*S*ESVEYYGTSL*MQWYQQKPGQPPKLLIF*AAS*NVKSGVPARFSGSG*

*SGTDFSLNIHPVEEDDIAMYF*CQQSGKVPHTF*GGGTKLEIKR*SME

IKRTDAQPAVYLFQPSPDQLHTGSASVVCLLNSFYPKDINVKWKV

DGVIQDTGIQESVTEQDKDSTYSLSSTLTMSSTEYLSHELYSCEI

THKSLPSTLIKSFQRSECQRVD*, wherein, Underline, signal sequence; Italic, FR; Bold, CDR; Bold and Underlined, CL; *, Stop; CDR1: ESVEYYGTSL (SEQ ID NO: 9); CDR2: AAS; and CDR3: CQQSGKVPHTF (SEQ ID NO: 10).

SEQ ID NO: 2 is the nucleotide sequence for the cPD-L1 12C10E4 kappa light chain of the cPD-L1 12C10E4 antibody (and encodes SEQ ID NO: 1) (codon optimized for CHO cell):

ATGGAGAGCGACACCCTCCTGCTGTGGGTGCTGCTACTGTGGGTT

CCTGGGAGCGCGGGAGACATCGTGCTGACACAGAGCCCTGCAAGC

CTGGCCGTGAGCCTGGGACAGAGAGCCACCATCAGCTGCAGAGCA

AGCGAGAGCGTGGAGTACTACGGCACAAGCCTGATGCAGTGGTAT

CAGCAGAAGCCTGGACAGCCTCCTAAGCTGCTGATCTTCGCCGCA

AGCAACGTGAAGAGCGGCGTGCCTGCTAGATTCAGCGGCAGCGGC

AGCGGCACCGACTTCAGCCTGAACATCCACCCTGTGGAGGAGGAC

GACATCGCCATGTACTTCTGTCAGCAGAGCGGCAAGGTGCCTCAC

ACCTTCGGCGGCGGCACCAAGCTGGAGATCAAGAGAtCCATGGAA

ATCAAACGTACGGATGCCCAGCCAGCCGTCTATTTGTTCCAACCA

TCTCCAGACCAGTTACACACAGGAAGTGCCTCTGTTGTGTGTTTG

CTGAATAGCTTCTACCCCAAAGACATCAATGTCAAGTGGAAAGTG

GATGGTGTCATCCAAGACACAGGCATCCAGGAAAGTGTCACAGAG

CAGGACAAGGACAGTACCTACAGCCTCAGCAGCACCCTGACGATG

TCCAGTACTGAGTACCTAAGTCATGAGTTGTACTCCTGTGAGATC

-continued

ACTCACAAGAGCCTGCCCTCCACCCTCATCAAGAGCTTCCAAAGG

AGCGAGTGTCAGAGAGTGGACTAA.

SEQ ID NO: 3 is the amino acid sequence for the cPD-L1 12C10E4 heavy chain of the cPD-L1 12C10E4 antibody (deduced from the DNA sequence). Additionally, SEQ ID NO: 3 is the amino acid sequence for the cPD-L1 A12C10E4 heavy chain of the cPD-L1 A12C10E4 antibody.

MAVLGLLFCLVTLPSCVLS*QVQLKQSGPGLVQPSQSLSITCTIS*G

FSLTSFGVHWVRQSPGKGLEWLGVIWSGGST*DYNAAFTSRLSINK*

*DNSKSQVFFKMNSLQADDTAIYYC*ARGGGPDWYFDV*WGTGTTVTV*

*SS*ASTTAPSVFPLAPSCGSTSGSTVALACLVSGYFPEPVTVSWNS

GSLTSGVHTFPSVLQSSGLYSLSSMVTVPSSRWPSETFTCNVAHP

ASKTKVDKPVPKRENGRVPRPPDCPKCPAPEMLGGPSVFIFPPKP

KDTLLIARTPEVTCVVVDLDPEDPEVQISWFVDGKQMQTAKTQPR

EEQFNGTYRVVSVLPIGHQDWLKGKQFTCKVNNKALPSPIERTIS

KARGQAHQPSVYVLPPSREELSKNTVSLTCLIKDFFPPDIDVEWQ

SNGQQEPESKYRTTPPQLDEDGSYFLYSKLSVDKSRWQRGDTFIC

AVMHEALHNHYTQKSLSHSPGK*, wherein Underline, signal sequence; Italic, FR; Bold, CDR; Bold and Underlined, CH; *, Stop; CDR1: GFSLTSFG (SEQ ID NO: 15); CDR2: IWSGGST (SEQ ID NO: 16); and CDR3; ARGGGPDWYFDV (SEQ ID NO: 11).

SEQ ID NO: 4 is the nucleotide sequence for the cPD-L1 12C10E4 heavy chain of the cPD-L1 12C10E4 antibody (and encodes SEQ ID NO: 3):

ATGGCCGTGCTGGGCCTGCTGTTCTGCCTGGTGACCCTGCCTAGC

TGCGTGCTGAGCCAAGTGCAGCTGAAGCAGAGCGGCCCTGGCCTG

GTGCAGCCTTCTCAGAGCCTGAGCATCACCTGCACCATCAGCGGC

TTCAGCCTGACAAGCTTCGGCGTGCACTGGGTGAGACAGAGCCCT

GGCAAGGGCCTGGAGTGGCTGGGCGTGATCTGGAGCGGCGGCAGC

ACCGACTACAACGCCGCCTTCACAAGCAGACTGAGCATCAACAAG

GACAACAGCAAGAGCCAAGTGTTCTTCAAGATGAACAGCCTGCAA

GCCGACGACACCGCCATCTACTACTGCGCTAGAGGCGGCGGCCCT

GACTGGTACTTCGACGTGTGGGGCACCGGCACCACCGTGACCGTG

AGCAGCGCTAGCACCACGGCCCCCTCGGTTTTCCCACTGGCCCCC

AGCTGCGGGTCCACTTCCGGCTCCACGGTGGCCCTGGCCTGCCTG

GTGTCAGGCTACTTCCCCGAGCCTGTAACTGTGTCCTGGAATTCC

GGCTCCTTGACCAGCGGTGTGCACACCTTCCCGTCCGTCCTGCAG

TCCTCAGGGCTCTACTCCCTCAGCAGCATGGTGACAGTGCCCTCC

AGCAGGTGGCCCAGCGAGACCTTCACCTGCAACGTGGCCCACCCG

GCCAGCAAAACTAAAGTAGACAAGCCAGTGCCCAAAAGAGAAAAT

GGAAGAGTTCCTCGCCCACCTGATTGTCCCAAATGCCCAGCCCCT

-continued

GAAATGCTGGGAGGGCCTTCGGTCTTCATCTTTCCCCCGAAACCC

AAGGACACCCTCTTGATTGCCCGAACACCTGAGGTCACATGTGTG

GTGGTGGATCTGGACCCAGAAGACCCTGAGGTGCAGATCAGCTGG

TTCGTGGACGGTAAGCAGATGCAAACAGCCAAGACTCAGCCTCGT

GAGGAGCAGTTCAATGGCACCTACCGTGTGGTCAGTGTCCTCCCC

ATTGGGCACCAGGACTGGCTCAAGGGGAAGCAGTTCACGTGCAAA

GTCAACAACAAAGCCCTCCCATCCCCGATCGAGAGGACCATCTCC

AAGGCCAGAGGGCAGGCCCATCAACCCAGTGTGTATGTCCTGCCG

CCATCCCGGGAGGAGTTGAGCAAGAACACAGTCAGCTTGACATGC

CTGATCAAAGACTTCTTCCCACCTGACATTGATGTGGAGTGGCAG

AGCAATGGACAGCAGGAGCCTGAGAGCAAGTACCGCACGACCCCG

CCCCAGCTGGACGAGGACGGGTCCTACTTCCTGTACAGCAAGCTC

TCTGTGGACAAGAGCCGCTGGCAGCGGGGAGACACCTTCATATGT

GCGGTGATGCATGAAGCTCTACACAACCACTACACACAGAAATCC

CTCTCCCATTCTCCGGGTAAATGA.

SEQ ID NO: 5 is the amino acid sequence for the cPD-L1 3C8D3 kappa light chain of the cPD-L1 3C chimeric antibody clone:

METHSQVFVYMLLWLSGVEG*DIVMTQSHKFMSTSVGDRVSITCKVS*QDVG

TA*VAWYQQKPGQCPKRLIY*WTS*TRHTGVPDRFTGSGSGTDFTLTISNVQS*

*EDLVDYF*CQQYSSYPLTF*GGGTKLELKRS*MEIKRTDAQPAVYLFQPSPDQ

LHTGSASVVCLLNSFYPKDINVKWKVDGVIQDTGIQESVTEQDKDSTYSL

SSTLTMSSTEYLSHELYSCEITHKSLPSTLIKSFQRSECQRVD*, wherein Underline, signal sequence; Italic, FR; Bold, CDR; Bold and Underlined, CL; *, Stop; CDR1: QDVGTA (SEQ ID NO: 17); CDR2: WTS; and CDR3: CQQYSSYPLTF (SEQ ID NO: 12).

SEQ ID NO: 6 is the nucleotide sequence for the cPD-L1 3C8D3 kappa light chain of the cPD-L1 3C chimeric antibody clone (and encodes SEQ ID NO: 5):

ATGGAGACACATTCTCAGGTCTTTGTATACATGTTGCTGTGGTTGTCTGG

TGTTGAAGGAGACATTGTGATGACCCAGTCTCACAAATTCATGTCCACAT

CAGTAGGAGACAGGGTCAGCATCACCTGCAAGGTTAGTCAGGATGTGGGT

ACCGCTGTAGCCTGGTATCAACAGAAACCAGGGCAATGTCCCAAAAGACT

GATTTACTGGACATCCACCCGGCACACTGGAGTCCCTGATCGCTTCACAG

GCAGTGGATCTGGGACAGATTTCACTCTCACCATTAGCAATGTGCAGTCT

GAAGACTTGGTAGATTATTTCTGTCAGCAATATAGCAGTTATCCTCTCAC

GTTCGGTGGTGGGACCAAGCTGGAGCTGAAACGGTCCATGGAAATCAAAC

GTACGGATGCCCAGCCAGCCGTCTATTTGTTCCAACCATCTCCAGACCAG

TTACACACAGGAAGTGCCTCTGTTGTGTGTTTGCTGAATAGCTTCTACCC

CAAAGACATCAATGTCAAGTGGAAAGTGGATGGTGTCATCCAAGACACAG

GCATCCAGGAAAGTGTCACAGAGCAGGACAAGGACAGTACCTACAGCCTC

-continued

AGCAGCACCCTGACGATGTCCAGTACTGAGTACCTAAGTCATGAGTTGTA

CTCCTGTGAGATCACTCACAAGAGCCTGCCCTCCACCCTCATCAAGAGCT

TCCAAAGGAGCGAGTGTCAGAGAGTGGACTAA.

SEQ ID NO: 7 is the amino acid sequence for the cPD-L1 3C8D3 heavy chain of the cPD-L1 3C chimeric antibody clone:

MGWSWIFLFLLSGTAGVLS*EVQLQQSGPELVKPGASVKMSCKAS*GYTFTD

YV*LHWVRQTNGKSLEWIGE*INPSNGDT*YYNQKFKGKATLTVDTSSSTAYM*

*QLTTLTSEDSAVYY*CARSDYSNYVGFAYW*GQGTLVTVSA*ASTTAPSVFPL

APSCGSTSGSTVALACLVSGYFPEPVTVSWNSGSLTSGVHTFPSVLQSSG

LYSLSSMVTVPSSRWPSETFTCNVAHPASKTKVDKPVPKRENGRVPRPPD

CPKCPAPEMLGGPSVFIFPPKPKDTLLIARTPEVTCVVVDLDPEDPEVQI

SWFVDGKQMQTAKTQPREEQFNGTYRVVSVLPIGHQDWLKGKQFTCKVNN

KALPSPIERTISKARGQAHQPSVYVLPPSREELSKNTVSLTCLIKDFFPP

DIDVEWQSNGQQEPESKYRTTPPQLDEDGSYFLYSKLSVDKSRWQRGDTF

ICAVMHEALHNHYTQKSLSHSPGK*, wherein, Underline, signal sequence; Italic, FR; Bold, CDR; Bold and Underlined, CL; *, Stop; CDR1: GYTFTDYV (SEQ ID NO: 18); CDR2: INPSNGDT (SEQ ID NO: 19); and CDR3: CARSDYSNYVGFAYW (SEQ ID NO: 13).

SEQ ID NO: 8 is the nucleotide sequence for the cPD-L1 3C8D3 heavy chain of the cPD-L1 3C chimeric antibody clone (and encodes SEQ ID NO: 7):

ATGGGATGGAGCTGGATCTTTCTCTTTCTCTTGTCAGGAACTGCAGGTGT

CCTCTCTGAAGTCCAGCTGCAACAGTCTGGACCTGAGCTGGTGAAGCCTG

GGGCTTCAGTGAAGATGTCCTGCAAGGCTTCTGGATACACATTCACTGAC

TATGTTTTGCACTGGGTGAGGCAGACCAATGGAAAGAGCCTTGAGTGGAT

TGGAGAAATTAATCCTAGCAATGGTGATACTTACTACAACCAGAAGTTCA

AGGGCAAGGCCACATTGACTGTAGACACATCCTCCAGCACAGCCTACATG

CAGCTCACCACCCTGACATCTGAGGACTCTGCAGTCTATTACTGTGCACG

ATCGGATTATAGTAACTACGTAGGATTTGCTTACTGGGGCCAAGGGACTC

TGGTCACTGTCTCTGCAGCTAGCACCACGGCCCCCTCGGTTTTCCCACTG

GCCCCCAGCTGCGGGTCCACTTCCGGCTCCACGGTGGCCCTGGCCTGCCT

GGTGTCAGGCTACTTCCCCGAGCCTGTAACTGTGTCCTGGAATTCCGGCT

CCTTGACCAGCGGTGTGCACACCTTCCCGTCCGTCCTGCAGTCCTCAGGG

CTCTACTCCCTCAGCAGCATGGTGACAGTGCCCTCCAGCAGGTGGCCCAG

CGAGACCTTCACCTGCAACGTGGCCCACCCGGCCAGCAAAACTAAAGTAG

ACAAGCCAGTGCCCAAAAGAGAAAATGGAAGAGTTCCTCGCCCACCTGAT

TGTCCCAAATGCCCAGCCCCTGAAATGCTGGGAGGGCCTTCGGTCTTCAT

CTTTCCCCCGAAACCCAAGGACACCCTCTTGATTGCCCGAACACCTGAGG

TCACATGTGTGGTGGTGGATCTGGACCCAGAAGACCCTGAGGTGCAGATC

AGCTGGTTCGTGGACGGTAAGCAGATGCAAACAGCCAAGACTCAGCCTCG

-continued

TGAGGAGCAGTTCAATGGCACCTACCGTGTGGTCAGTGTCCTCCCCATTG

GGCACCAGGACTGGCTCAAGGGGAAGCAGTTCACGTGCAAAGTCAACAAC

AAAGCCCTCCCATCCCCGATCGAGAGGACCATCTCCAAGGCCAGAGGGCA

GGCCCATCAACCCAGTGTGTATGTCCTGCCGCCATCCCGGGAGGAGTTGA

GCAAGAACACAGTCAGCTTGACATGCCTGATCAAAGACTTCTTCCCACCT

GACATTGATGTGGAGTGGCAGAGCAATGGACAGCAGGAGCCTGAGAGCAA

GTACCGCACGACCCCGCCCCAGCTGGACGAGGACGGGTCCTACTTCCTGT

ACAGCAAGCTCTCTGTGGACAAGAGCCGCTGGCAGCGGGGAGACACCTTC

ATATGTGCGGTGATGCATGAAGCTCTACACAACCACTACACACAGAAATC

CCTCTCCCATTCTCCGGGTAAATGA.

SEQ ID NO: 9 is the amino acid sequence for a CDR1: ESVEYYGTSL.

SEQ ID NO: 10 is the amino acid sequence for a CDR3: CQQSGKVPHTF.

SEQ ID NO: 11 is the amino acid sequence for a CDR3: ARGGGPDWYFDV.

SEQ ID NO: 12 is the amino acid sequence for a CDR3: CQQYSSYPLTF.

SEQ ID NO: 13 is the amino acid sequence for a CDR3: CARSDYSNYVGFAYW.

SEQ ID NO: 14 is a portion of the amino acid sequence for the cPD-L1 12C chimeric antibody clone and the cPD-L1 A12C10E4 chimeric antibody clone: GDTFICAVMHEALHNHYTQK. This is located in the heavy chain of SEQ ID NO: 3.

SEQ ID NO: 15 is the amino acid sequence for a CDR1: GFSLTSFG.

SEQ ID NO: 16 is the amino acid sequence for a CDR2: IWSGGST.

SEQ ID NO: 17 is the amino acid sequence for a CDR1: QDVGTA.

SEQ ID NO: 18 is the amino acid sequence for a CDR1: GYTFTDYV.

SEQ ID NO: 19 is the amino acid sequence for a CDR2: INPSNGDT.

SEQ ID NO: 20 is the nucleotide sequence for a pre-assembled guide RNA related to full length of canine CD274 cDNA (NM_001291972): CAGCAAATATCCTCATGTTTTGG.

SEQ ID NO: 21 is the nucleotide sequence of a forward primer of primer set 1 described herein: CCACTTGGTTCTACATGGCT.

SEQ ID NO: 22 is the nucleotide sequence of a reverse primer of primer set 1 described herein: CCTCAGCCTGACACATTAGTT.

SEQ ID NO: 23 is the nucleotide sequence of a forward primer of primer set 2 described herein: CCTGTCACCTCTGAACATGAA.

SEQ ID NO: 24 is the nucleotide sequence of a reverse primer of primer set 2 described herein: GGACTAAGCTCTAGGTTGTCC.

SEQ ID NO: 25 is the nucleotide sequence of a forward primer of primer set 3 described herein: GACTGGCTTTTAGGGCTTATGT.

SEQ ID NO: 26 is the nucleotide sequence of a reverse primer of primer set 3 described herein: ACACCCCACAAATTACTTCCATT.

SEQ ID NO: 27 is the amino acid sequence for the cPD-L1 A12C10E4 kappa light chain of the cPD-L1 A12C10E4 antibody:

MESDTLLLWVLLLWVPGSAG*DIVLTQSPASLAVSLGQRATISCRAS*ESVE

YYGTSL*MQWYQQKPGQPPKLLIF*AAS*NVKSGVPARFSGSGSGTDFSLNIH*

*PVEEDDIAMYF*CQQSGKVPHTF*GGGTKLEIKR*SMADAQPAVYLFQPSPDQ

LHTGSASVVCLLNSFYPKDINVKWKVDGVIQDTGIQESVTEQDKDSTYSL

SSTLTMSSTEYLSHELYSCEITHKSLPSTLIKSFQRSECQRVD*, wherein, Underline, signal sequence; Italic, FR; Bold, CDR; Bold and Underlined, CL; *, Stop; CDR1: ESVEYYGTSL (SEQ ID NO: 9); CDR2: AAS; and CDR3: CQQSGKVPHTF (SEQ ID NO: 10).

SEQ ID NO: 28 is the nucleotide sequence for the cPD-L1 A12C10E4 kappa light chain of the cPD-L1 12C10E4 antibody (and encodes SEQ ID NO: 27) (codon optimized for CHO cell):

ATGGAAAGTGATACTCTACTACTATGGGTGCTCCTGCTGTGGGTCCCTGG

CTCTGCTGGCGATATCGTGCTGACCCAGTCCCCCGCCTCTCTGGCCGTGT

CCTTGGGCCAGCGCGCTACAATTTCCTGCAGAGCCTCCGAGAGCGTGGAA

TACTACGGCACCTCTCTGATGCAGTGGTACCAGCAGAAGCCTGGACAACC

TCCTAAGCTGCTGATCTTCGCCGCTTCTAATGTCAAATCTGGCGTGCCAG

CCAGATTCTCCGGCAGCGGATCCGGCACCGACTTTAGCCTGAACATCCAC

CCTGTGGAAGAGGACGACATCGCCATGTACTTCTGCCAGCAGTCTGGCAA

AGTGCCTCATACCTTCGGCGGCGGAACCAAGCTGGAAATCAAGCGGTCCA

TGGCCGATGCTCAGCCTGCTGTGTACCTGTTCCAGCCCTCCCCTGACCAG

CTGCACACCGGCTCTGCCTCTGTGGTGTGCCTGCTGAACTCCTTCTACCC

CAAGGACATCAACGTGAAGTGGAAGGTGGACGGCGTGATCCAGGACACCG

GCATCCAAGAGTCCGTGACCGAGCAGGACAAGGACTCCACCTACTCCCTG

TCCTCTACCCTGACCATGTCCTCCACAGAATATCTGTCTCACGAGCTGTA

CAGCTGCGAGATCACCCACAAGAGCCTGCCTTCTACACTGATCAAGTCCT

TTCAGCGGTCTGAGTGTCAGAGAGTGGAT.

SEQ ID NO: 29 is the nucleotide sequence for the cPD-L1 A12C10E4 heavy chain of the cPD-L1 A12C10E4 antibody (and encodes SEQ ID NO: 3):

ATGGCAGTGCTAGGTCTACTATTTTGCCTAGTCACTCTGCCCTCCTGCGT

GCTGTCCCAGGTACAGCTCAAGCAGTCTGGACCTGGCCTGGTGCAGCCCA

GCCAGTCTCTGTCCATCACCTGTACAATTTCCGGCTTCTCGCTGACATCC

TTCGGCGTGCACTGGGTGCGGCAGTCTCCCGGCAAGGGCTTGGAGTGGCT

GGGCGTGATCTGGTCCGGCGGCTCCACCGACTACAACGCCGCTTTCACAT

CTCGCCTGTCTATCAACAAGGATAACTCTAAGTCCCAAGTGTTCTTCAAG

ATGAACTCCCTGCAGGCTGACGACACCGCCATCTACTACTGCGCTCGGGG

AGGCGGCCCTGATTGGTACTTCGACGTGTGGGGCACCGGAACAACCGTTA

CTGTGTCCTCTGCCTCCACCACCGCTCCTTCCGTGTTCCCTCTGGCCCCT

TCTTGCGGCTCTACCTCCGGGTCTACAGTGGCTCTGGCCTGCCTGGTGTC

CGGCTACTTTCCTGAACCCGTGACCGTGTCCTGGAACTCCGGCTCTCTGA

CCTCTGGCGTGCACACCTTCCCCTCCGTGCTGCAGTCCAGCGGCCTGTAT

-continued

TCCCTCTCCAGCATGGTCACCGTGCCCAGCTCCAGATGGCCTAGCGAAAC

CTTTACCTGCAACGTGGCCCATCCTGCCTCTAAAACCAAGGTGGATAAGC

CTGTGCCAAAGAGAGAGAATGGCAGAGTGCCTAGGCCTCCTGACTGCCCC

AAGTGTCCTGCTCCTGAGATGCTGGGCGGACCCTCCGTGTTTATCTTCCC

TCCTAAACCTAAGGATACCCTGCTGATCGCCAGAACCCCAGAAGTCACCT

GTGTGGTGGTGGACCTGGATCCTGAGGACCCTGAGGTGCAGATCTCTTGG

TTCGTGGACGGCAAGCAGATGCAGACCGCCAAGACCCAGCCTCGGGAAGA

GCAGTTCAACGGCACCTACAGAGTGGTCTCTGTGCTGCCTATCGGCCACC

AGGACTGGCTGAAAGGCAAACAGTTCACCTGCAAGGTGAACAACAAGGCC

CTGCCTTCTCCCATCGAGAGAACCATCTCTAAGGCTAGAGGCCAGGCTCA

TCAACCTAGTGTGTACGTGCTGCCACCTTCCAGAGAGGAACTGAGCAAGA

ACACCGTGTCGCTCACCTGTCTGATCAAGGACTTCTTTCCACCTGACATC

GACGTGGAATGGCAGTCCAATGGCCAGCAAGAGCCTGAGTCCAAGTACCG

GACCACCCCTCCTCAGCTGGACGAGGATGGCTCCTACTTCCTGTACTCCA

AGCTGAGCGTGGACAAGTCCCGGTGGCAGCGGGGCGACACATTCATCTGC

GCCGTGATGCACGAGGCCCTGCACAACCACTACACCCAGAAGTCTCTGAG

TCACTCTCCAGGAAAA.

DETAILED DESCRIPTION

For the purposes of promoting an understanding of the principles of the present disclosure, reference will now be made to the embodiments illustrated in the drawings and specific language will be used to describe the same. It will nevertheless be understood that no limitation of scope is intended by the description of these embodiments. On the contrary, this disclosure is intended to cover alternatives, modifications, and equivalents as may be included within the spirit and scope of this application as defined by the appended claims. As previously noted, while this technology may be illustrated and described in one or more preferred embodiments, the compositions, compounds and methods hereof may comprise many different configurations, forms, materials, and accessories.

Novel canine programmed death-ligand 1 (cPD-L1) antibodies and cPD-L1 antigen binding fragments are provided. The term "canine" includes all domestic dogs, *Canis lupus familiaris* or *Canis familiaris*, unless otherwise indicated. These antibodies and antigen binding fragments can be used as an immuno-oncology drug, for example. When administered, these antibodies and antigen binding fragments can increase tumor cell killing activity in a subject. In certain embodiments, the antibodies and antigen binding fragments hereof can inhibit the immunosuppressive function of cPD-L1 in the presence of cancer cells. Given that the expression of PD-L1 on T cells and natural killer (NK) cells has been reported, together with the blockade of PD-L1 on cancer cells by the antibodies and/or antigen binding fragments hereof, a direct effect of PD-L1 on T cells or other immune cells can also enhance the efficacy of the antibodies and antigen binding fragments hereof when administered to a subject, in addition to targeting the PD-L1 on cancer cells.

Antibodies and Complementarity Determining Regions (CDRs)

Canine programmed cell death protein 1 (PD-1)/PD-L1 blockade antibodies are not widely available for dogs with invasive urothelial carcinoma (InvUC). Tumor regression in dogs with oral melanoma and soft tissue sarcomas has been reported in response to a canine chimeric monoclonal antibody targeting PD-L1. The antitumor effects of the antibody, however, were indeterminate as the role of concurrent medications in tumor regression was not known (Maekawa et al., A canine chimeric monoclonal antibody targeting PD-L1 and its clinical efficacy in canine oral malignant melanoma or undifferentiated sarcoma. Sci Rep 7:8951 (2017); Knapp et al., Phase I trial of piroxicam in 62 dogs bearing naturally occurring tumors, *Cancer Chemother Pharmacol* 29, 214-218 (1992); and Nemoto et al., Development and characterization of monoclonal antibodies against canine PD-1 and PD-L1. *Vet Immunol Immunopathol* 198:19-25 (2018)). In other work, anti-canine PD-1 and PD-L1 antibodies have been developed for diagnostic applications, but have not been tested therapeutically (Choi et al., Development of canine PD-1/PD-L1 specific monoclonal antibodies and amplification of canine T cell function, *PLOS One* 15: e0235518 (2020)). Accordingly, a canine immune checkpoint blockade antibody or anti-canine PD-L1 antibody is not conventionally available for translational research or treatment in dogs.

An immunotherapeutic PD-L1 antibody (or an antigen binding fragment thereof) is provided. As used herein, the term "antibody" refers to any form of immunoglobulin that exhibits the desired biological activity. Thus, it is used in the broadest sense and specifically covers, but is not limited to, monoclonal antibodies (including full length monoclonal antibodies), polyclonal antibodies, multi-specific antibodies (e.g., bispecific antibodies), caninized antibodies, fully canine antibodies, chimeric antibodies, and single domain antibodies. "Parental antibodies" are antibodies obtained by exposure of an immune system to an antigen prior to modification of the antibodies for an intended sue, such as caninization of an antibody for use as a canine therapeutic antibody.

The variable regions of each light/heavy chain pair form the antibody binding site. Thus, in general, an intact antibody has two binding sites. Except in bifunctional or bispecific antibodies, the two binding sites are, in general, identical. Typically, the variable domains of both the heavy and light chains comprise three hypervariable regions, also called CDRs, located between relatively conserved variable framework regions (FRs). The CDRs are usually flanked by the FRs, enabling binding to a specific epitope. In general, from N-terminal to C-terminal, both light and heavy chains variable domains comprise FR1, CDR1, FR2, CDR2, FR3, CDR3 and FR4.

As used herein, unless otherwise indicated. "antibody fragment" or "antibody binding fragment" refers to antigen binding fragments of antibodies, i.e. antibody fragments that retain the ability to bind specifically to the antigen bound by the full-length antibody. Examples of antigen binding fragments include, without limitation, Fab, Fab', F(ab')$_2$, and Fv fragments; diabodies; linear antibodies; single-chain antibody molecules (e.g., sc-Fv); nanobodies and multi-specific antibodies formed from antibody fragments. A "Fab fragment" is comprised of one light chain constant, one light chain variable, one CHI and one variable region-domains of one heavy chain. A "Fab fragment" can be the product of papain cleavage of an antibody. A "fragment crystallizable" (Fc) region is a tail region of an antibody that interacts with cell surface receptors and allows antibodies to activate the immune system. The Fc region contains at least two heavy chain fragments (i.e. two identical polypeptides) comprising the $CH_2$ and $CH_3$ domains of an antibody. The two heavy chain fragments can be held together by two or more disulfide bonds and by hydrophobic interactions of the $CH_3$ domains.

A "Fab' fragment" contains one light chain and a portion or fragment of one heavy chain that contains the heavy chain variable domain (VH) domain and the CHI domain and also the region between the $CH_1$ and $CH_2$ domains, such that an interchain disulfide bond can be formed between the two heavy chains and two Fab' fragments to form a F(ab')$_2$ molecule.

In certain embodiments, the PD-L1 antibody (or an antigen binding fragment thereof) is a chimeric form of a caninized antibody (e.g., monoclonal) or an antigen binding fragment thereof that binds canine PD-L1 in a canine subject with specificity (e.g., has high binding affinity for PD-L1 in a canine subject). As used herein, a "chimeric antibody" is an antibody having the variable domain from a first antibody and the constant domain from a second antibody, where the first and second antibodies are from different species. For example, the variable segments of the genes (e.g., the framework and CDR portions) from, for example, a mouse antibody (e.g., a monoclonal or polyclonal antibody) can be used in conjunction with canine or human constant segments to produce the chimeric antibody. A typical therapeutic chimeric antibody is thus a hybrid protein composed of the variable or antigen-binding domain from a mouse antibody (e.g., one or more of the CDRs of a mouse antibody) and the constant or effector domain from a human or canine antibody, although other mammalian species can be used. A chimeric antibody can also include amino acid sequences obtained from a protein source other than an antibody.

In certain embodiments, the antibody or antigen binding fragment thereof binds canine PD-L1 with specificity. As used herein, an antibody or antigen binding fragment thereof binds "with specificity" to a polypeptide comprising a given antigen sequence (e.g., a portion of an amino acid sequence of a canine antigen, e.g., cPD-L1) if it binds to polypeptides comprising that portion of the amino acid sequence of the canine antigen, for example, cPD-L1, but does not bind to other canine proteins lacking that portion of the sequence of the canine antigen. For example, an antibody that specifically binds to a polypeptide comprising canine PD-L1 can bind to a FLAG-tagged form of canine PD-L1 but will not bind to other FLAG-tagged canine proteins with specificity. An antibody, or binding compound derived from the antigen-binding site of an antibody, binds to its canine antigen (or a variant or mutein thereof) "with specificity" when it has an affinity for that canine antigen or a variant or mutein thereof that is at least ten-times greater, at least fifteen-times greater, at least 20-times greater, or at least 100-times greater than its affinity for any other canine antigen tested.

The cPD-L1 antibody can comprise the amino acid sequence of SEQ ID NOS: 1 and/or 3, or SEQ ID NOS: 5 and/or 7 or SEQ ID NOS: 27 and/or 3. The cPD-L1 antibody is encoded by the nucleotide sequence comprising SEQ ID NOS: 2 and/or 4, or SEQ ID NOS: 6 and/or 8, or SEQ ID NOS: 28 and/or 29.

In certain embodiments, the antibody (or an antigen binding fragment thereof) is caninized. In certain embodiments, the antibody (or an antigen binding fragment thereof) is completely caninized. In certain embodiments, the antibody (or an antigen binding fragment thereof) is incompletely caninized. As used herein, the term "caninized antibody" refers to forms of antibodies that contain sequences from both canine and non-canine (e.g., murine or rat) antibodies. In general, the caninized antibody can comprise substantially all of at least one, and typically two, variable domains, in which all or substantially all of the hypervariable loops correspond to those of a non-canine immunoglobulin (e.g., comprising 6 murine anti-canine PD-L1 CDRs as exemplified below), and all or substantially all of the parental framework. A caninized antibody can also refer to an antibody where point mutations are made changing one amino acid to reflect that commonly found at that position in canines versus that commonly found at that position in a mouse or rat species.

The caninized regions are those in which the amino acid identity at selected positions is changed from the original (i.e., rat or mouse) amino acid to ones that more closely reflect common canine amino acids at those position. These changes are made in an attempt to prevent or reduce host anti-antibody responses during or after therapy. These undesired anti-antibody responses are commonly found when the host (in this case, a dog) detects an unusual amino acid identity in a position of importance. As a non-limiting example, a dog can raise an undesired immune response to a lysine found at position 29 (Lys29) because dog antibodies rarely, if ever, have a lysine at position 29. The caninization process can then result in changing Lysine 29 to Alanine (Lys29Ala) in an attempt to avoid a strong immune response to the antibody which could have severe side effects. Most common caninization changes are placed in the variable domains of a therapeutic antibody, though it is possible to need caninization changes in one or more other antibody regions as well. The anti-PD-L1 antibody (or an antigen binding fragment thereof) can comprise a caninized murine PD-L1 antibody or an antigen binding fragment thereof.

In certain embodiments, the antibody or an antigen binding fragment thereof comprises a caninized antibody wherein all or a portion of the mouse (or other mammalian) CDR sequences are replaced with the corresponding canine CDR sequences or portion(s) thereof. The antibody or an antigen binding fragment thereof can comprise a fusion of one or more variable regions of mouse DNA with constant regions for canine DNA. In certain embodiments, caninized anti-canine PD-L1 antibodies are caninized mammalian (e.g., murine) anti-canine PD-L1 antibodies.

CDRs are those portions of variable regions of immunoglobulins (i.e., antibodies) and T cell receptors that participate in the binding of specific antigens, epitopes, or peptides. There are three CDRs (CDR1, CDR2, and CDR3), arranged non-consecutively, on an amino acid sequence of a variable domain of a complete antigen receptor, for example. As antigen receptors are typically comprised of two variable domains (on two different chains-heavy and light chain), there are six CDRs for each antigen receptor that can collectively come into contact with an antigen.

The antibodies (or antigen binding fragments thereof) can comprise one or more genetically modified CDRs. In certain embodiments, a CDR (e.g., of the antibody or antigen binding fragment thereof) comprises AAS, SEQ ID NO: 9, and/or SEQ ID NO: 10, or has at least 90%, or about 90%-100% (such as about 90% to 100%, 90% to about 100%, or 90-100%), sequence identity to AAS, SEQ ID NO: 9, and/or SEQ ID NO: 10. In certain embodiments a CDR comprises at least 95%, or between about 95%-100% (such as about 95% to 100%, 95% to about 100%, or 95-100%), sequence identity to AAS, SEQ ID NO: 9, and/or SEQ ID NO: 10. In certain embodiments, a CDR comprises about 97%-100% (such as about 97% to 100%, 97% to about 100%, or 97-100%) sequence identity to AAS, SEQ ID NO: 9, and/or SEQ ID NO: 10. In certain embodiments a CDR comprises about 95% (such as 95%) sequence identity to AAS, SEQ ID NO: 9, and/or SEQ ID NO: 10. The ranges specified in this paragraph are inclusive of the stated end points and all 1% increments therein. In certain embodiments, the CDR (e.g., of the antibody or antigen binding fragment thereof) comprises AAS, SEQ ID NO: 9, and/or SEQ ID NO: 10 or a sequence that is 90%, 95%, 97%, 98%, or 99% identical to the sequence of AAS, SEQ ID NO: 9, and/or SEQ ID NO: 10. In certain embodiments, the CDR comprises a sequence that is substantially identical to AAS, SEQ ID NO: 9, and/or SEQ ID NO: 10.

In certain embodiments, a CDR comprises SEQ ID NO: 15, SEQ ID NO: 16, and/or SEQ ID NO: 11 or has at least about 90%, or has about 90%-100% (such as about 90% to 100%, 90% to about 100%, or 90-100%), sequence identity (or is substantially identical) to SEQ ID NO: 15, SEQ ID NO: 16, and/or SEQ ID NO: 11. In certain embodiments a CDR comprises between about 95%-100% (such as about 95% to 100%, 95% to about 100%, or 95-100%) sequence identity to SEQ ID NO: 15, SEQ ID NO: 16, and/or SEQ ID NO: 11. In certain embodiments, a CDR comprises between about 97%-100% (such as about 97% to 100%, 97% to about 100%, or 97-100%) sequence identity to SEQ ID NO: 15, SEQ ID NO: 16, and/or SEQ ID NO: 11. In certain embodiments a CDR comprises about 95% (such as 95%) sequence identity to SEQ ID NO: 15, SEQ ID NO: 16, and/or SEQ ID NO: 11. The ranges specified in this paragraph are inclusive of the stated end points and all 1% increments therein. In certain embodiments, the CDR (e.g., of the antibody or antigen binding fragment thereof) comprises SEQ ID NO: 15, SEQ ID NO: 16, and/or SEQ ID NO: 11 or a sequence that is 90%, 95%, 97%, 98%, or 99% identical to the sequence of SEQ ID NO: 15, SEQ ID NO: 16, and/or SEQ ID NO: 11.

In certain embodiments, an anti-cPD-L1 antibody or antigen binding fragment, can comprise one or more CDRs independently comprising at least about 90% sequence identity to AAS, SEQ ID NO: 9, and/or SEQ ID NO: 10. In still further embodiments, the antibody or antigen binding fragment can comprise one or more CDRs independently comprising at least about 95% sequence identity to AAS, SEQ ID NO: 9, and/or SEQ ID NO: 10, or at least about 97% or more sequence identity to AAS, SEQ ID NO: 9, and/or SEQ ID NO: 10. In certain embodiments, a cPD-L1 antibody or antigen binding fragment can comprise one or more CDRs independently comprising at least about 90% sequence identity to SEQ ID NO: 15, SEQ ID NO: 16, and/or SEQ ID NO: 11. In still further embodiments, the antibody or antigen binding fragment can comprise one or more CDRs independently comprising at least about 95% sequence identity to SEQ ID NO: 15, SEQ ID NO: 16 and/or SEQ ID NO: 11, or at least about 97% or more sequence identity to SEQ ID NO: 15, SEQ ID NO: 16 and/or SEQ ID NO: 11.

In certain embodiments, an antibody hereof (or an antigen binding fragment thereof) comprises two or more of the CDRs described herein.

In certain embodiments, the antibody hereof is a monoclonal antibody. In certain embodiments, the monoclonal antibody is a murine antibody. In certain embodiments, the monoclonal antibody is a caninized antibody. In certain embodiments, the monoclonal antibody hereof is a caninized murine antibody. The antibodies (and/or their antigen binding fragments) can be isolated antibodies (or isolated antigen binding fragments). "Isolated antibody" or "isolated antigen binding fragment" refers to the purification status and in such context means the molecule is substantially free of other biological molecules such as nucleic acids, proteins, lipids, carbohydrates, or other material such as cellular debris and growth media. Generally, unless otherwise specified, the term "isolated" is not intended to refer to a complete absence of such material or to an absence of water, buffers, or salts, unless they are present in amounts that substantially interfere with experimental or therapeutic use of the binding compound as described herein.

In certain embodiments, the antibody is a recombinant antibody or antigen binding fragment. In certain embodiments, the heavy chain variable domain and the light chain variable domain are connected by a flexible linker to form a single chain antibody.

The antibody or antigen binding fragment can be a Fab fragment. The antibody or antigen binding fragment can be a Fab' fragment. The antibody or antigen binding fragment can be a $F(ab')_2$ molecule. In certain embodiments, the antibody or antigen binding fragment is a diabody. In certain embodiments, the antibody or antigen binding fragment is a domain antibody.

Nucleic acids (including isolated nucleic acids) encoding any of the antibodies, fragments, and/or portions thereof (including CDRs) are also provided. In certain embodiments, nucleic acids that encode any of the light chains or caninized antibodies or portions thereof are provided. Similarly, nucleic acids that encode any of the heavy chains or caninized antibodies or portions thereof are provided.

The nucleic acid sequence encoding an antibody hereof can comprise SEQ ID NO: 2. In examples, the nucleic acid sequence encoding an antibody hereof comprises at least about 80% sequence identity to SEQ ID NO: 2, or has about 80%-100% (such as about 80% to 100%, 80% to about 100%, or 80-100%) sequence identity (or is substantially identical), to SEQ ID NO: 2. In examples, the nucleic acid sequence encoding an antibody hereof comprises between about 85%-95% (such as about 85% to 95%, 85% to about 95%, or 85-95%) sequence identity to SEQ ID NO: 2. In examples, the nucleic acid sequence encoding an antibody hereof comprises 87%-93% (such as about 87% to 93%, 87% to about 93%, or 87-93%) sequence identity to SEQ ID NO: 2. The nucleic acid sequence encoding an antibody hereof comprises about 90% (such as 90%) sequence identity to SEQ ID NO: 2. The ranges specified in this paragraph are inclusive of the stated end points and all 1% increments therein. In examples, the nucleic acid sequence encoding an antibody hereof comprises SEQ ID NO: 2 or a sequence that is 90%, 95%, 98%, or 99% identical to the sequence of SEQ ID NO: 2.

The nucleic acid sequence encoding an antibody hereof can comprise SEQ ID NO: 4. In examples, the nucleic acid sequence encoding an antibody hereof comprises at least about 80% sequence identity to SEQ ID NO: 4, or has about 80%-100% (such as about 80% to 100%, 80% to about 100%, or 80-100%) sequence identity (or is substantially identical) to SEQ ID NO: 4. In examples, the nucleic acid sequence encoding an antibody hereof comprises between about 85%-95% (such as about 85% to 95%, 85% to about 95%, or 85-95%) sequence identity to SEQ ID NO: 4. In examples, the nucleic acid sequence encoding an antibody hereof comprises 87%-93% (such as about 87% to 93%, 87% to about 93%, or 87-93%) sequence identity to SEQ ID NO: 4. The nucleic acid sequence encoding an antibody hereof comprises about 90% (such as 90%) sequence identity to SEQ ID NO: 4. The ranges specified in this paragraph are inclusive of the stated end points and all 1% increments therein. In examples, the nucleic acid sequence encoding an antibody hereof comprises SEQ ID NO: 4 or a sequence that is 90%, 95%, 98%, or 99% identical to the sequence of SEQ ID NO: 4.

In certain examples, the nucleic acid sequence encoding an antibody hereof comprises SEQ ID NOS: 2 and 4.

The nucleic acid sequence encoding an antibody hereof can comprise SEQ ID NO: 28. In certain embodiments, the nucleic acid sequence encoding an antibody hereof comprises at least about 80% sequence identity to SEQ ID NO: 28, or has about 80%-100% (such as about 80% to 100%, 80% to about 100%, or 80-100%) sequence identity (or is substantially identical), to SEQ ID NO: 28. In certain embodiments, the nucleic acid sequence encoding an antibody hereof comprises between about 85%-95% (such as about 85% to 95%, 85% to about 95%, or 85-95%) sequence identity to SEQ ID NO: 28. In certain embodiments, the nucleic acid sequence encoding an antibody hereof comprises 87%-93% (such as about 87% to 93%, 87% to about 93%, or 87-93%) sequence identity to SEQ ID NO: 28. The nucleic acid sequence encoding an antibody hereof comprises about 90% (such as 90%) sequence identity to SEQ ID NO: 28. The ranges specified in this paragraph are inclusive of the stated end points and all 1% increments therein. In certain embodiments, the nucleic acid sequence encoding an antibody hereof comprises SEQ ID NO: 28 or a sequence that is 90%, 95%, 98%, or 99% identical to the sequence of SEQ ID NO: 28.

The nucleic acid sequence encoding an antibody hereof can comprise SEQ ID NO: 29. In certain embodiments, the nucleic acid sequence encoding an antibody hereof comprises at least about 80% sequence identity to SEQ ID NO: 29, or has about 80%-100% (such as about 80% to 100%, 80% to about 100%, or 80-100%) sequence identity (or is substantially identical), to SEQ ID NO: 29. In certain embodiments, the nucleic acid sequence encoding an antibody hereof comprises between about 85%-95% (such as about 85% to 95%, 85% to about 95%, or 85-95%) sequence identity to SEQ ID NO: 29. In certain embodiments, the nucleic acid sequence encoding an antibody hereof comprises 87%-93% (such as about 87% to 93%, 87% to about 93%, or 87-93%) sequence identity to SEQ ID NO: 29. The nucleic acid sequence encoding an antibody hereof comprises about 90% (such as 90%) sequence identity to SEQ ID NO: 29. The ranges specified in this paragraph are inclusive of the stated end points and all 1% increments therein. In certain embodiments, the nucleic acid sequence encoding an antibody hereof comprises SEQ ID NO: 29 or a sequence that is 90%, 95%, 98%, or 99% identical to the sequence of SEQ ID NO: 29.

In certain embodiments, the nucleic acid sequence encoding an antibody hereof comprises SEQ ID NO: 28 and SEQ ID NO: 29.

The nucleotide sequences SEQ ID NO: 4 and SEQ ID NO: 29 have been codon optimized to give rise to the same amino acid sequence SEQ ID NO: 3. It is well known to those skilled in the art that when making a cell line, multiple nucleotide sequences may be codon optimized such that when expressed in a cell they will give rise to the same amino acid sequence as the non-optimized nucleotide sequence. Additionally, it is well known to those skilled in the art that further codon optimization may be done to make additional nucleic acid sequences which encode to the same amino acid sequence.

In examples, the nucleic acid sequence encoding an antibody hereof comprises SEQ ID NO: 6, has at least 80% sequence identity to, or has about 80%-100% (such as about 80% to 100%, 80% to about 100%, or 80-100%) sequence identity (or is substantially identical) to, SEQ ID NO: 6. In certain examples, the nucleic acid sequence encoding an antibody hereof comprises between about 85%-95% (such as about 85% to 95%, 85% to about 95%, or 85-95%) sequence identity to SEQ ID NO: 6. In certain examples, the nucleic acid sequence encoding an antibody hereof comprises 87%-93% (such as about 87% to 93%, 87% to about 93%, or 87-93%) sequence identity to SEQ ID NO: 6. The nucleic acid sequence encoding an antibody hereof comprises about 90% (such as 90%) sequence identity to SEQ ID NO: 6. The ranges specified in this paragraph are inclusive of the stated end points and all 1% increments therein. In certain examples, the nucleic acid sequence encoding an antibody hereof comprises SEQ ID NO: 6 or a sequence that is 90%, 95%, 98%, or 99% identical to the sequence of SEQ ID NO: 6.

In examples, the nucleic acid sequence encoding an antibody hereof comprises SEQ ID NO: 8, has at least 80% sequence identity to, or has about 80%-100% (such as about 80% to 100%, 80% to about 100%, or 80-100%) sequence identity (or is substantially identical) to, SEQ ID NO: 8. In certain examples, the nucleic acid sequence encoding an antibody hereof comprises between about 85%-95% (such as about 85% to 95%, 85% to about 95%, or 85-95%) sequence identity to SEQ ID NO: 8. In certain examples, the nucleic acid sequence encoding an antibody hereof comprises 87%-93% (such as about 87% to 93%, 87% to about 93%, or 87-93%) sequence identity to SEQ ID NO: 8. The nucleic acid sequence encoding an antibody hereof comprises about 90% (such as 90%) sequence identity to SEQ ID NO: 8. The ranges specified in this paragraph are inclusive of the stated end points and all 1% increments therein. In certain examples, the nucleic acid sequence encoding an antibody hereof comprises SEQ ID NO: 8 or a sequence that is 90%, 95%, 98%, or 99% identical to the sequence of SEQ ID NO: 8.

In examples, the nucleic acid sequence encoding an antibody hereof comprises SEQ ID NOS: 6 and 8.

In certain embodiments, the antibodies (or antigen binding fragments thereof) to canine PD-L1 comprise one or more of the CDRs described herein and/or bind to an amino acid sequence of PD-L1. In certain embodiments, the dissociation constant ($K_D$) for caninized antibody-canine PD-L1 binding is between about 4.0 nmol/L to 10.0 nmol/L (such as 4.0) nmol/L to about 10.0 nmol/L, about 4.0) nmol/L to about 10.0 nmol/L, or about 4.0 nmol/L to 10.0 nmol/L). In certain embodiments, the antibodies (e.g., caninized antibodies) or their antigen-binding fragments bind to canine PD-L1 with a $K_D$ of at or between about 4.2 nmol/L to 9.8 nmol/L (such as 4.2 nmol/L to about 9.8 nmol/L, about 4.2 nmol/L to about 9.8 nmol/L, or about 4.2 nmol/L to 9.8 nmol/L). In certain embodiments, the antibodies (e.g., caninized antibodies) or their antigen-binding fragments bind to canine PD-L1 with a $K_D$ of at or between about 4.4 nmol/L to 9.6 nmol/L (such as 4.4 nmol/L to about 9.6 nmol/L, about 4.4 nmol/L to about 9.6 nmol/L, or about 4.4 nmol/L to 9.6 nmol/L). In certain embodiments, the antibodies (e.g., caninized antibodies) or their antigen-binding fragments bind to canine PD-L1 with a $K_D$ of at or between about 4.6 nmol/L to 9.4 nmol/L (such as 4.6 nmol/L to about 9.4 nmol/L, about 4.6 nmol/L to about 9.4 nmol/L, or about 4.6 nmol/L to 9.4 nmol/L). In certain embodiments, the antibodies (e.g., caninized antibodies) or their antigen-binding fragments bind to canine PD-L1 with a $K_D$ of at or between about 4.8 nmol/L to 9.2 nmol/L (such as 4.8 nmol/L to about 9.2 nmol/L, about 4.8 nmol/L to about 9.2 nmol/L, or about 4.8 nmol/L to 9.2 nmol/L). In certain embodiments, the antibodies (e.g., caninized antibodies) or their antigen-binding fragments bind to canine PD-L1 with a $K_D$ of at or between about 5.0 nmol/L to 9.0 nmol/L (such as 5.0 nmol/L to about 9.0 nmol/L, about 5.0 nmol/L to about 9.0 nmol/L, or about 5.0 nmol/L to 9.0 nmol/L). In certain embodiments, the antibodies (e.g., caninized antibodies) or their antigen-binding fragments bind to canine PD-L1 with a $K_D$ of at or between about 5.2 nmol/L to 8.8 nmol/L (such as 5.2 nmol/L to about 8.8 nmol/L, about 5.2 nmol/L to about 8.8 nmol/L, or about 5.2 nmol/L to 8.8 nmol/L). In certain embodiments, the antibodies (e.g., caninized antibodies) or their antigen-binding fragments bind to canine PD-L1 with a $K_D$ of at or between about 5.4 nmol/L to 8.6 nmol/L (such as 5.4 nmol/L to about 8.6 nmol/L, about 5.4 nmol/L to about 8.6 nmol/L, or about 5.4 nmol/L to 8.6 nmol/L). In certain embodiments, the antibodies (e.g., caninized antibodies) or their antigen-binding fragments bind to canine PD-L1 with a $K_D$ 8.6 nmol/L, In certain embodiments, the antibodies (e.g., caninized antibodies) or their antigen-binding fragments bind to canine PD-L1 with a $K_D$ of at or between about 5.6 nmol/L to 8.4 nmol/L (such as 5.6 nmol/L to about 8.4 nmol/L, about 5.6 nmol/L to about 8.4 nmol/L, or about 5.6 nmol/L to 8.4 nmol/L). In certain embodiments, the antibodies (e.g., caninized antibodies) or their antigen-binding fragments bind to canine PD-L1 with a $K_D$ of at or between about 5.8 nmol/L to 8.2 nmol/L (such as 5.8 nmol/L to about 8.2 nmol/L, about 5.8 nmol/L to about 8.2 nmol/L, or about 5.8 nmol/L to 8.2 nmol/L). In certain embodiments, the antibodies (e.g., caninized antibodies) or their antigen-binding fragments bind to canine PD-L1 with a $K_D$ of at or between about 6.0 nmol/L to 8.0 nmol/L (such as 6.0 nmol/L to about 8.0) nmol/L, about 6.0 nmol/L to about 8.0 nmol/L, or about 6.0 nmol/L to 8.0 nmol/L). In certain embodiments, the antibodies (e.g., caninized antibodies) or their antigen-binding fragments bind to canine PD-L1 with a $K_D$ of at or between about 6.2 nmol/L to 7.8 nmol/L (such as 6.2 nmol/L to about 7.8 nmol/L, about 6.2 nmol/L to about 7.8 nmol/L, or about 6.2 nmol/L to 7.8 nmol/L). In certain embodiments, the antibodies (e.g., caninized antibodies) or their antigen-binding fragments bind to canine PD-L1 with a $K_D$ of at or between about 6.4 nmol/L to 7.6 nmol/L (such as 6.4 nmol/L to about 7.6 nmol/L, about 6.4 nmol/L to about 7.6 nmol/L, or about 6.4 nmol/L to 7.6 nmol/L). In certain embodiments, the antibodies (e.g., caninized antibodies) or their antigen-binding fragments bind to canine PD-L1 with a $K_D$ of at or between about 6.6 nmol/L to 7.4 nmol/L (such as 6.6 nmol/L to about 7.4 nmol/L, about 6.6 nmol/L to about 7.4 nmol/L, or about 6.6 nmol/L to 7.4 nmol/L). The ranges specified in this paragraph are inclusive of the stated end points and all 0.1 increments encompassed thereby.

The antibodies or their antigen-binding fragments can stimulate antigen-specific memory responses to a tumor or pathogen. In certain embodiments, the antibodies or their antigen-binding fragments can stimulate an antibody response in vivo in a subject. In certain embodiments, the antibodies or their antigen-binding fragments can stimulate an immune response in an animal subject (e.g., a canine animal subject). The term "immune response" refers to the action of, for example, lymphocytes, antigen-presenting cells, phagocytic cells, granulocytes, and soluble macromolecules produced by the above cells or the liver (including antibodies, cytokines, and complement) that can result in selective damage to, destruction, or elimination of the mammalian body (e.g., canine body) results from cancer cells, cells, or tissues infected with invading pathogens or pathogens.

In certain embodiments, the antibodies or their antigen binding fragments can bind to canine PD-L1 and also block the binding of canine PD-L1 to PD-1. In certain embodiments, the caninized antibodies and their antigen-binding fragments hereof can bind to canine PD-L1 and block the binding of canine PD-L1 to PD-1.

The antibodies or antigen-binding fragments can be used for the preparation of a medicament for treating cancer in a canine subject. The antibodies (or antigen binding fragments thereof) can be administered in unit dosage forms and/or compositions containing one or more pharmaceutically acceptable carriers, adjuvants, diluents, excipients, and/or vehicles, and combinations thereof. The term "administering" and its formatives generally refer to any and all means of introducing compounds described herein to the host subject including, but not limited to, by oral, intravenous, intramuscular, subcutaneous, transdermal, inhalation, buccal, ocular, sublingual, vaginal, rectal, and like routes of administration.

Alternatively, or in conjunction, the use of any of the antibodies or antibody fragments hereof is provided for diagnostic use. In certain embodiments, an expression vector is provided comprising an isolated nucleic acid encoding any of the caninized murine anti-canine PD-L1 antibodies or antigen-binding fragments hereof. Host cells are also provided that comprise one or more expression vectors described herein. In particular embodiments, these nucleic acids, expression vectors, or polypeptides can be useful in methods for preparing an antibody.

Pharmaceutical compositions are also provided. The pharmaceutical compositions can comprise one or more of the antibodies, antigen binding fragments described herein, antigenic peptides (including isolated antigenic peptides) of canine PD-L1, fusion proteins comprising the canine PD-L1 antigenic peptides, nucleic acids encoding the antigenic fragments and/or fusion proteins hereof, the expression vectors comprising such nucleic acids, or any combination thereof, and a pharmaceutically acceptable carrier or diluent. The term "composition" generally refers to any product comprising more than one ingredient, including without limitation the antibodies or antigen binding fragments thereof. In certain embodiments, the pharmaceutical composition comprises the caninized antibody, a chimerized antibody, or an antigen binding fragment thereof and a pharmaceutically acceptable excipient.

The compositions can be prepared from isolated antibodies or antigen binding fragments thereof or from salts, solutions, hydrates, solvates, and other forms of the antibodies or antigen binding fragments thereof. The compositions can be prepared from various amorphous, non-amorphous, partially crystalline, crystalline, and/or other morphological forms of the antibodies or antigen binding fragments thereof, and the compositions can be prepared from various hydrates and/or solvates of the compounds.

The antibodies or antigen binding fragments thereof can be formulated as pharmaceutical compositions and administered to a mammalian host, such as a human or canine subject, in a variety of forms adapted to the chosen route of administration. For example, the pharmaceutical composition can be formulated for and administered via oral or parenteral, intravenous, intraarterial, intraperitoneal, intrathecal, epidural, intracerebroventricular, intraurethral, intrasternal, intracranial, intra-tumoral, intramuscular, topical, inhalation and/or subcutaneous routes. Indeed, in at least one embodiment, a compound and/or composition can be administered directly into the blood stream, into muscle, or into an internal organ.

For example, in at least one embodiment, the antibodies or antigen binding fragments thereof can be systemically administered (orally, for example) in combination with a pharmaceutically acceptable vehicle, such as an inert diluent or an assimilable edible carrier. For oral therapeutic administration, the antibody or an antigen binding fragment thereof can be combined with one or more excipients and used in the form of ingestible tablets, buccal tablets, troches, capsules, elixirs, suspensions, syrups, wafers, and the like. The percentage of the compositions and preparations can vary and can be between about 1 to about 99% weight of the active ingredient(s) and a binder, excipients, a disintegrating agent, a lubricant, and/or a sweetening agent (as are known in the art). The amount of antibody or an antigen binding fragment thereof in such therapeutically useful compositions is such that an effective dosage level will be obtained.

The preparation of parenteral compounds/compositions under sterile conditions, for example, by lyophilization, can readily be accomplished using standard pharmaceutical techniques well-known to those skilled in the art. In at least one embodiment, the solubility of a compound used in the preparation of a parenteral composition can be increased by the use of appropriate formulation techniques, such as the incorporation of solubility-enhancing agents.

As previously noted, the antibodies or antigen binding fragments thereof can also be administered via infusion or injection (e.g., using needle (including microneedle) injectors and/or needle-free injectors). Solutions of the active composition can be aqueous, optionally mixed with a nontoxic surfactant and/or can contain carriers or excipients such as salts, carbohydrates and buffering agents (preferably at a pH of from 3 to 9), but, for some applications, they can be more suitably formulated as a sterile non-aqueous solution or as a dried form to be used in conjunction with a suitable vehicle such as sterile, pyrogen-free water or phosphate-buffered saline (PBS). For example, dispersions can be prepared in glycerol, liquid PEGs, triacetin, and mixtures thereof and in oils. Under ordinary conditions of storage and use, these preparations can further contain a preservative to prevent the growth of microorganisms.

Methods for Treatment

A method of treating animal cancers is provided using the antibodies or antigen binding fragments hereof, particularly invasive urothelial carcinoma (InvUC) in canines, which comprises greater than about 90% of dog bladder cancers. In at least one embodiment, the method comprises administering a therapeutically effective amount of any of the antibodies or antigen binding fragments thereof to a canine subject (e.g., to treat a cancer). The cancer can be, for example, any canine cancer including, without limitation, InvUC. In certain embodiments, administration of the therapeutically effective amount of the caninized antibody, chimeric antibody, or an antigen binding fragment thereof inhibits PD-L1/PD-1 interaction in the subject. In certain embodiments, administration of the therapeutically effective amount of the caninized antibody, chimeric antibody, or an antigen binding fragment thereof increases the activity of an immune cell in the subject.

The subject can be a mammal. The subject can be a canine. The subject can be a companion dog.

"Effective amount" or "therapeutically effective amount" refers to an amount of a therapeutic agent (e.g., an antibody or antigen binding fragment thereof), or composition comprising the same, that elicits the desired biological or medicinal response in a subject (i.e., a tissue, organ, or organism, such as a vertebrate, e.g., mammal, such as a human or a canine) that is being sought by a researcher, veterinarian, medical doctor, or other clinician, which includes, but is not limited to, imaging and/or alleviation of the signs and/or symptoms of the disease or disorder being treated. In one aspect, the effective amount is an amount of an active agent which can treat or alleviate the signs and/or symptoms of the disease at a reasonable benefit/risk ratio applicable to any medical treatment. An "effective amount" or "therapeutically effective amount" with respect to use in treatment refers to an amount of the active agent/antibody in a preparation which, when administered as part of a desired dosage regimen (e.g., to a mammal, such as a human or canine) alleviates a symptom, ameliorates a condition, or slows the onset of disease according to clinically acceptable standards for the disorder or condition to be treated or the cosmetic purpose, e.g., at a reasonable benefit/risk ratio applicable to any medical treatment.

Combined with the teachings provided herein, by choosing among the various active agents and weighing factors such as potency, relative bioavailability, subject body weight, severity of adverse side-effects and mode of administration, an effective prophylactic or therapeutic treatment regimen can be planned which does not cause substantial unwanted toxicity and yet is effective to treat the particular subject.

Depending upon the type of cancer, the route of administration and/or whether the antibodies or antigen binding fragments thereof are administered locally or systemically, a wide range of permissible dosages are contemplated herein. The amount of the composition required for use in treatment (e.g., the therapeutically or prophylactically effective amount or dose) will vary not only with the particular application and dosage structure, but also with the salt selected (if applicable) and the characteristics of the subject (such as, for example, species, breed, age, condition, sex, the subject's body surface area and/or mass, tolerance to drugs) and will ultimately be at the discretion of the attendant physician, veterinarian, clinician, or otherwise.

Therapeutically effective amounts or doses can range, for example, from about 0.05 mg/kg of subject body weight to about 30.0 mg/kg of subject body weight, or from about 0.01 mg/kg of subject body weight to about 5.0 mg/kg of subject body weight, including but not limited to 0.01 mg/kg, 0.02 mg/kg, 0.03 mg/kg, 0.04 mg/kg, 0.05 mg/kg, 0.1 mg/kg, 0.2 mg/kg, 0.3 mg/kg, 0.4 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, and 5.0 mg/kg, all of which are kg of subject body weight. The total therapeutically effective amount of the compound can be administered in single or divided doses and can, at the practitioner's discretion, fall outside of the typical range given herein.

Higher doses can be required for parenteral administration. The effective amount for any particular application can vary depending on such factors as the disease or condition being treated, the particular antibodies being administered, the size of the subject, or the severity of the disease or condition. One of ordinary skill in the art can empirically determine the effective amount of a particular antibody, antigen binding fragment thereof, and/or other therapeutic agent without necessitating undue experimentation. A maximum dose can be used, that is, the highest safe dose according to some medical judgment. Multiple doses per day can be used to achieve appropriate systemic levels of compounds. Appropriate systemic levels can be determined by, for example, measurement of the patient's peak or sustained plasma level of the drug. "Dose" and "dosage" are used interchangeably herein.

Adjusting the dose to achieve maximal efficacy based on the methods described and other methods well-known in the art is well within the capabilities of the ordinarily skilled artisan. Dosage can be adjusted appropriately to achieve desired drug levels, local or systemic, depending upon the mode of administration. For example, the dose for intravenous administration can vary from one order to several orders of magnitude lower per day. If the response in a subject is insufficient at such doses, even higher doses (or effective higher doses by a different, more localized delivery route) can be employed to the extent that subject tolerance permits. Multiple doses per day are contemplated to achieve appropriate systemic levels of the compound.

Any effective regimen for administering the antibodies or antigen binding fragments thereof can be used. The dosages can be single or divided and can be administered according to a wide variety of protocols, including q.d., b.i.d., t.i.d., or even every other day, biweekly (b.i.w.), once a week, once a month, once a quarter, and the like. In each of these cases it is understood that the effective amounts described herein correspond to the instance of administration, or alternatively to the total daily, weekly, month, or quarterly dose, as determined by the dosing protocol.

For example, an antibody can be administered as a single dose, or the dose can be divided and administered as a multiple-dose daily regimen. Further, a staggered regimen, for example, one to five days per week can be used as an alternative to daily treatment. Such intermittent or staggered daily regimen is considered equivalent to daily treatment. The subject can be treated with multiple injections of an antibody or antigen binding fragment thereof to treat cancer. The subject can be injected multiple times (e.g., approximately 2-50×) with an antibody or an antigen binding fragment thereof, for example, at 12-72 hours intervals or at 48-72 hours intervals. Additional injections of an antibody or an antigen binding fragment thereof can be administered to the subject at an interval of days or months after the initial injection(s), and the additional injections can prevent the recurrence of the cancer.

The methods can be used in combination with one or more additional therapies and/or active agents. Such additional therapies include, without limitation, additional immunotherapies, the administration of a DNA damage response pathway inhibitor, chemotherapy, radiation and/or a surgery.

Methods for Predicting and Modeling Anti-Cancer Activity of a Test Compound

Companion dogs naturally develop several types of cancer that in many respects resemble clinical cancer in human patients. Although mouse models are the most commonly used animal model in cancer research, they do not possess collective features such as tumor heterogeneity, mutational landscape, cancer molecular subtypes, and immune cell responsiveness that mimics the conditions desired for optimal animal models. Studies in the mouse models can be complemented by other models such as specific forms of naturally occurring cancer in pet dogs. This can be especially beneficial when developing or studying new immune-oncology drugs such as novel immune checkpoint inhibitors (ICIs) or their combination regimens where companion dogs can offer naturally occurring cancer in the context of an intact immune system and an aggressive heterogeneous cancer. The development of canine ICIs can expand comparative oncology approaches to improve the current therapeutic efficacy of immunotherapies in human cancer. Accordingly, the canine studies of immune-oncology drugs can be convertible into knowledge that informs and prioritizes new immune-oncology therapy in humans. Conventionally, however, the challenge has been that ICIs that target canine immune checkpoint molecules such as cPD-1 and cPD-L1 are not available.

In the development of immuno-oncology drugs, particularly immunotherapeutic antibodies, translation of the discoveries from mouse models to clinical trials has been hindered by many biological differences between mice and humans, such as no cross-reactivity between species and/or that the mouse physiological system can react differently to cancer and other pathologic insults than does the human or dog system. For example, if anti-human or canine PD-L1 antibody does not recognize mouse PD-L1 protein, the human or canine antibody's therapeutic efficacy cannot be evaluated in a syngeneic mouse model. Human immune system-engrafted mice have been developed for translational research to overcome this constraint. Indeed, pembrolizumab, an anti-human PD-1 antibody, showed tumor growth inhibition and CD8+ T cell activation in the humanized NSG (HuNSG) mice that received tumor implant from patient-derived xenografts (PDX) (see, e.g., Wang et al., Humanized mice in studying efficacy and mechanisms of PD-1-targeted cancer immunotherapy; *FASEB J* 32:1537-1549 (2018)). Despite human tumor-bearing human immune system engrafted mice being an important model for preclinical immuno-oncology research, there are considerable obstacles such as a limited source of human cells and tissues, immune rejection, and high cost in these humanized mouse models (see, e.g., Yong et al., Humanized mice as unique tools for human-specific studies, *Arch Immunol Ther Exp* (*Warsz*) 66:245-266 (2018)).

As an alternative mouse model for immunotherapeutic antibody development, mice that are humanized for immune checkpoint molecules are commercially available. For example, the humanized PD-L1 mouse has been generated by replacing the mouse PD-L1 gene (cd274) with the human PD-L1 gene ((I) 274) using the clustered regularly interspaced short palindromic repeats (CRISPR)/CAS9 strategy. The humanized PD-L1 mouse can be used for evaluating anti-human PD-L1 antibody's therapeutic efficacy in vivo; however, the canine PD-L1 gene knock-in mouse model hereof that can be used for evaluating anti-canine PD-L1 antibody's therapeutic efficacy has heretofore not been available, which has caused a major roadblock for developing canine immune checkpoint inhibitors such as PD-1/PD-L1 blockade antibodies. The PD-L1 mouse model hereof can be used not only for preclinical immune-oncology research, but also as a translational research tool to bridge the gap between canines and humans and, thus, increase success rates of immunotherapy applications in humans.

Methods for predicting and modeling (e.g., optimizing) anti-cancer activity of a test compound in a secondary subject using the antibodies or antigen binding fragments hereof are also provided. In certain embodiments, the antibodies or antigen binding fragments thereof are caninized and evaluated in canines (e.g., the primary subject), and those test compounds with the highest success are advanced to human trials (e.g., wherein the secondary subject is human).

In certain embodiments, a method for predicting and modeling anti-cancer activity of a test compound in a subject comprises generating a population of mice that express canine PD-L1 on a cell surface; evaluating toxicity risk and/or efficacy in treating a cancer of a set of test compounds in the population of PD-L1 mice; and selecting one or more test compounds of the set that satisfy established toxicity risk and/or efficacy criteria. The set of test compounds can comprise, for example, at least a compound that inhibits (or is reasonably expected could inhibit) PD-L1/PD-1 interaction in the subject.

In certain embodiments, the method further comprises evaluating oral bioavailability, adsorption, distribution, metabolism, and excretion (ADME) values of the set of test compounds in the population of mice that contain canine PD-L land PD-1. In certain embodiments, the method further comprises evaluating oral bioavailability and ADME values of the selected one or more test compounds in the population of PD-L1 mice.

The method can further comprise evaluating the toxicity risk and/or efficacy of the one or more selected compounds in treating a cancer in a human or canine cohort.

The toxicity risk and/or efficacy criteria can be established pursuant to known protocols.

Generating the population of PD-L1 mice can further comprise replacing a mouse cd274 gene in a population of mice with a canine PD-L1 gene using CRISPR or other known technologies.

The canine models hereof can be useful in studies of InvUC-specific therapies. This concept is supported by the data that human InvUC can replicate in canines and the similarities between human InvUC and canine InvUC. Canine InvUC mimics human InvUC in presentation, pathology, local invasion, distant metastases (lung, etc., in greater than 50% of cases), and chemotherapy response (see, e.g., Cekanova et al., Molecular imaging of cyclooxygenase-2 in canine transitional cell carcinomas in vitro and in vivo. *Cancer Prev Res* (*Phila*) 6:466-76 (2013); Fulkerson et al., Naturally occurring canine invasive urinary bladder cancer: A complementary animal model to improve the success rate in human clinical trials of new cancer drugs, *Int J Genomics,* 6589529 (2017); Knapp et al., Cisplatin versus cisplatin combined with piroxicam in a canine model of human invasive urinary bladder cancer, *Cancer Chemother Pharmacol* 46:221-226 (2000); Knapp et al., Urinary bladder cancer in dogs, a naturally occurring model for cancer biology and drug development, *ILAR J* 55:100-118 (2014); Lin et al., Targeting canine bladder transitional cell carcinoma with a human bladder cancer-specific ligand, Mol Cancer 10:9 (2011); Patrick et al., Classification of canine urinary bladder urothelial tumours based on the World Health Organization/International Society of Urological Pathology consensus classification, *J Comp Pathol* 135:190-199 (2006); Sommer et al., Naturally-occurring canine invasive urothelial carcinoma: A model for emerging therapies, *Bladder Cancer* 4:149-159 (2018); and Suarez-Bonnet et al., Expression of cell cycle regulators, 14-3-3sigma and p53 proteins, and vimentin in canine transitional cell carcinoma of the urinary bladder, *Urol Oncol* 33:332 e1-7 (2015)). With InvUC comprising two percent (2%) of the roughly six million new canine cancer cases each year in the United States, ample number of dogs are available for translational studies (see, e.g., Davis and Ostrander, Domestic dogs and cancer research: a breed-based genomics approach, *ILAR J* 55:59-68 (2014)). Canine clinical trials in which the test subjects continue life as pets following the studies can be win-win with benefits to each dog and the knowledge gained to help people and pet dogs. Accordingly, dogs offer an excellent opportunity to advance PD-1/PD-L1 blockade therapies in humans. Successful treatment approaches in rodents can then be evaluated in dogs, and those with the highest success moved into human trials.

EXAMPLES

The present disclosure will be better understood by reference to the following Examples, which are provided as exemplary examples and not by way of limitation.

Materials

BT549 human breast cancer and MB49 mouse bladder cancer cell lines were obtained from the American Type Culture Collection (ATCC) (Manassas, VA) and Sigma-Aldrich (St. Louis, MO), respectively. Canine bladder cancer cell line, K9TCC, was generated in the Knapp Lab. (see Igase et al. (2020), supra). Human embryonic kidney cell line HEK293FT was obtained from Thermo Fisher Scientific (Waltham, MA). Cell lines were validated by short tandem repeat DNA fingerprinting using the AmpFlSTR Identifier PCT Amplification Kit (Thermo Fisher Scientific, Waltham, MA) according to manufacturer's instructions.

The cells were tested for *Mycoplasma* using the *Mycoplasma* PCR Detection Kit (ABM).

Cells were grown in Dulbecco's Modified Eagle Medium (DMEM) or DMEM/Nutrient Mixture F-12 (DMEM/F-12) medium supplemented with 10% fetal bovine serum (FBS) for no more than 15 passages.

For stable expression of PD-L1, cDNA of canine PD-L1 (Sino Biological, Wayne, PA) was inserted into a pGIPZ vector (Horizen Discovery, Waterbeach, UK) as described in Lim et al. (2016), supra. Using a pGIPZ-shPD-L1/Flag-cPD-L1 dual-expression construct to knockdown endogenous human PD-L1 and reconstitute Flag-cPD-L1 simultaneously, endogenous PD-L1 knockdown and Flag-cPD-L1 expressing BT549 cell lines were established. See, e.g., Lim et al., EGFR signaling enhances aerobic glycolysis in triple negative breast cancer cells to promote tumor growth and immune escape, Cancer Res (2016).

Lentivirus was packaged by co-transfecting transfer plasmids with plasmid pMD2.G (Addgene #12259) and pCMV dR8.2 (Addgene #12263) to HEK293FT cells with X-tremeGENE HP (Roche Diagnostics, Indianapolis, IN), and the supernatant was harvested for lentiviral transduction. Selection with 1 μg/mL puromycin (InvivoGen, San Diego, CA) was routinely performed to maintain ectopic gene expression.

For mouse PD-L1 knockout, mouse PD-L1 double nickase plasmid (Santa Cruz Biotechnology, Dallas, TX) was transfected into MB49 cells using X-tremeGENE transfection reagent.

For canine PD-L1 overexpression MB49 cells ($MB49^{cPDL1}$), mouse PD-L1 KO MB49 cells were infected with lentivirus carrying pGIPZ-Flag-cPD-L1 followed by selection with puromycin.

All animal work was approved by the Purdue Animal Care and Use Committee (PACUC) at Purdue University.

For flow cytometry analysis, MB49 or BT549 cells were washed twice with ice-cold cell staining buffer (Biolegend, San Diego, CA) and stained with cIgG control, or cPD-L1 12C10E4 cIgG or cPD-L1 A12C10E4 cIgG for 1 hour at 4° C. After three washes with staining buffer, cell samples were stained with Alexa Fluor 488-conjugated anti-canine IgG specific secondary antibody for 30 minutes at 4° C. Cell samples were loaded on BD LSRFortessa (BD, Franklin Lakes, NJ) for analysis. Data analysis was performed on FlowJo v9 software (BD). Every hour, green fluorescent signal was measured and quantified by IncuCyte S3 (Sartorius, Goettingen, Germany). The Image analysis was performed according to the manufacturer's protocol.

Example 1

Creation and Selection of Anti-Canine PD-L1 Monoclonal Antibodies

Monoclonal antibodies 3C8D3 (mAb 3C) and cPD-L1 12C10E4 (mAb 12C) were generated via conventional hybridoma procedures using A/J mice immunized with the extracellular domain of canine programmed death-ligand 1 (cPD-L1) (attached to a human Fc tag) at the Vanderbilt University Antibody and Protein Resource Core Facility. Briefly, splenocytes were isolated from the immunized mice and fused with SP2/0 myeloma cells (see FIG. 1). Supernatants from isolated clones were screened for the ability to block the canine programmed cell death protein 1 (cPD-1)/cPD-L1 interaction through cPD-L1 expressing cell-based enzyme-linked immunosorbent assays (ELISAs), with the mAbs 3C and 12C selected for further study. Clonal antibodies were purified from supernatants and the same assays were repeated. Anti-cPD-L1 mAbs were successfully generated using these conventional hybridoma procedures.

To screen for antibodies that could block the cPD-1/cPD-L1 interaction for use in a therapeutic setting, live cell-based antibody binding and PD-1/PD-L1 blockade assays were developed (see FIGS. 2A and 2B) similar to those previously published. See, e.g., Li et al., Eradication of triple-negative breast cancer cells by targeting glycosylated PD-L1. *Cancer Cell* 33:187-201 e10 (2018); Lim et al., Deubiquitination and stabilization of PD-L1 by SCN5. *Cancer Cell* (2016); Li et al., Glycosylation and stabilization of programmed death ligand-1 suppresses T-cell activity. *Nat Commun* 7:12632 (2016).

Figure 2A:
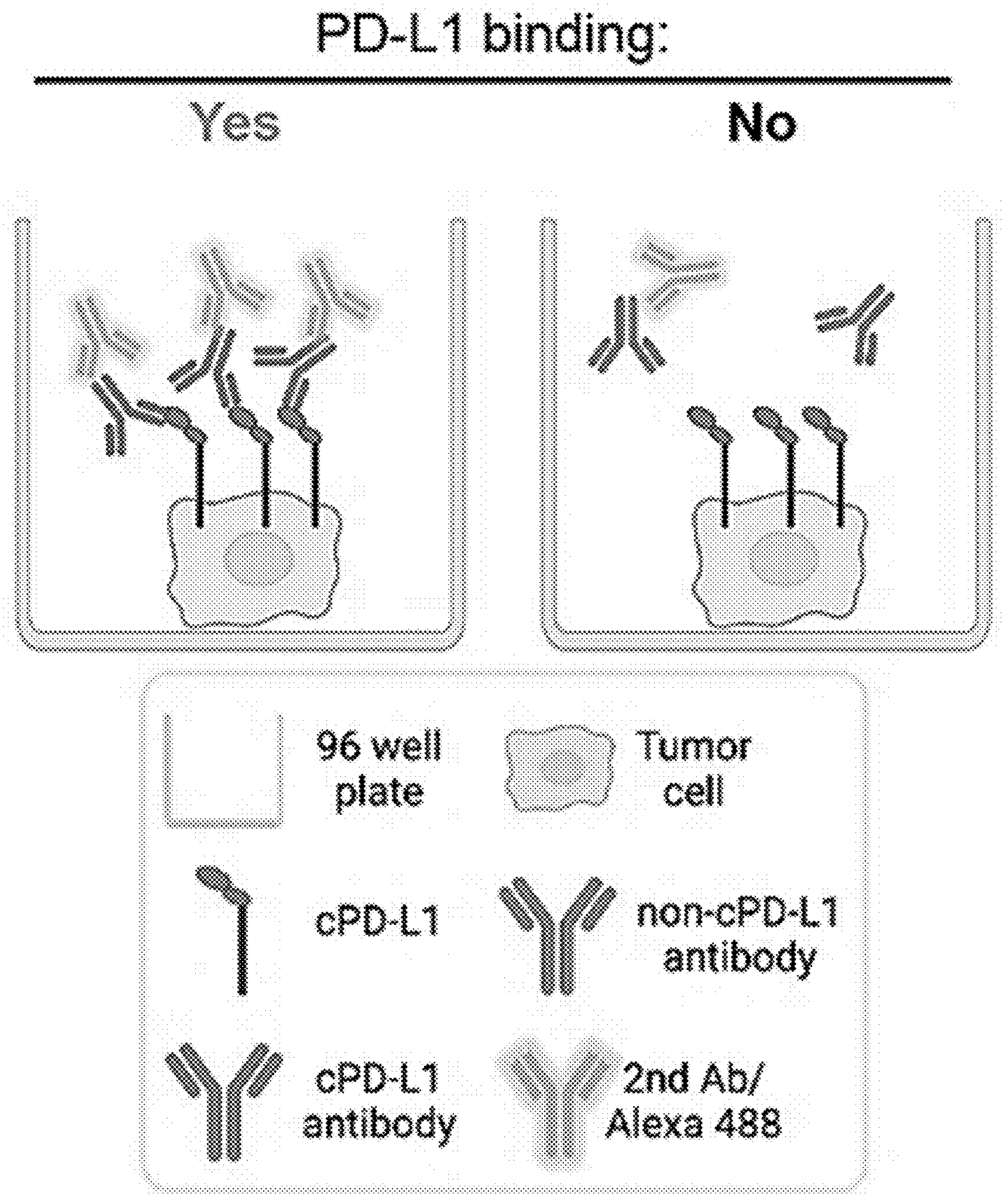
FIG. 2A is a schematic diagram of the canine programmed death-ligand 1 (cPD-L1) antibody binding assay.

Human cancer cell line BT549 cells expressing cPD-L1 were seeded on 96-well or 384-well plates, cPD-L1 antibodies (from hybridomas) and Alexa Fluor® 488-conjugated anti-mouse IgG fc specific secondary antibody were added, and green fluorescence signal was measured to quantify the amount of bound PD-L1 antibody by the IncuCyte® S3 Live-Cell Analysis System (Sartorius AG, Gottingen, Germany) (FIG. 2A).

Figure 2B:
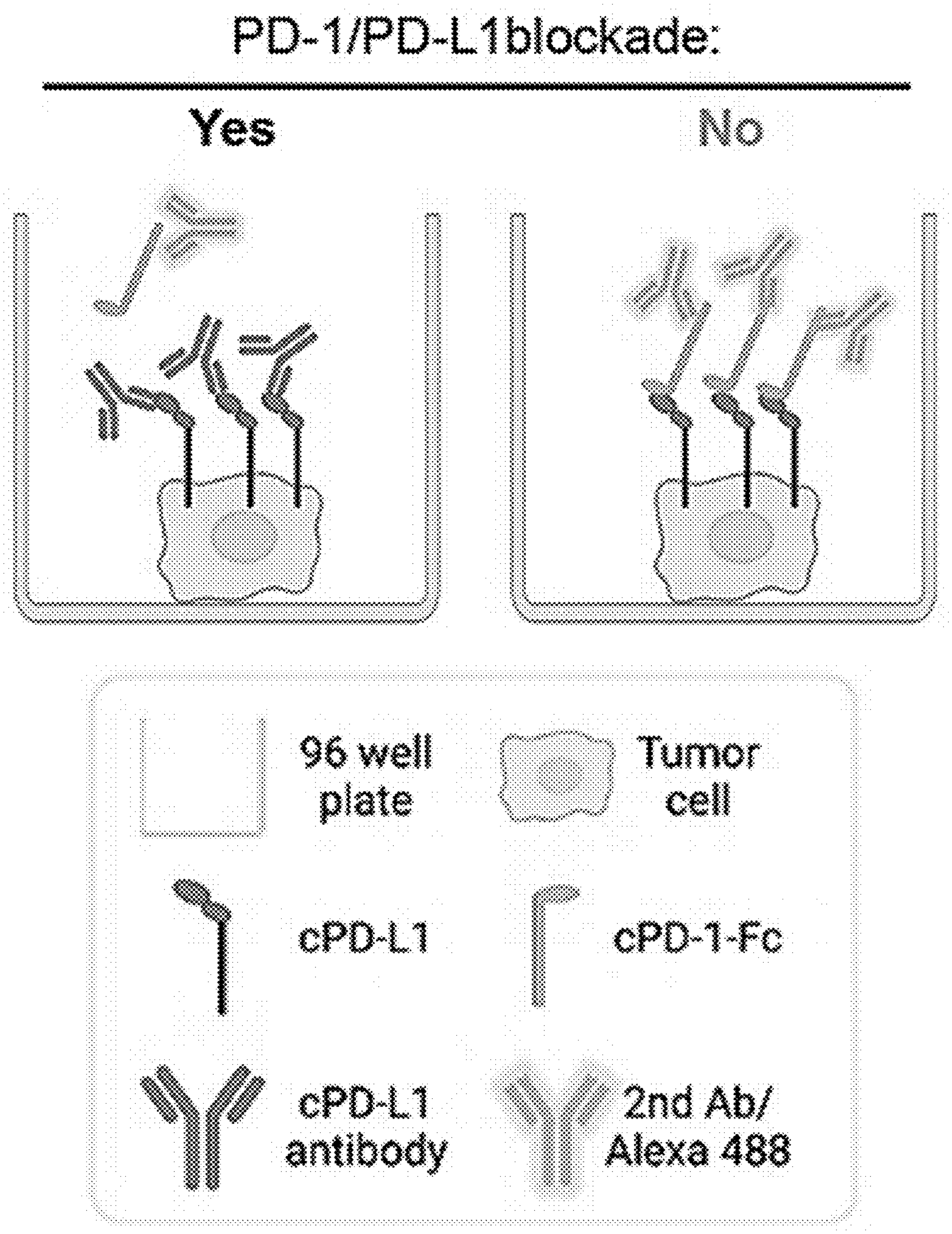
FIG. 2B is a schematic diagram of the cPD-L1/canine programmed death protein 1 (cPD-1) blockade assay.

BT549 cells expressing cPD-L1 were seeded on 96-well or 384-well plates, cPD-1-human Fc (hFc) protein. Alexa Fluor® 488-conjugated anti-human IgG Fc specific secondary antibody and/or cPD-L1 antibody were added and then green fluorescence signal was measured to quantify the amount of bound PD-1 protein by IncuCyte® S3 Live-Cell Analysis System (Sartorius AG. Gottingen, Germany) (FIG. 2B).

Figure 2C:
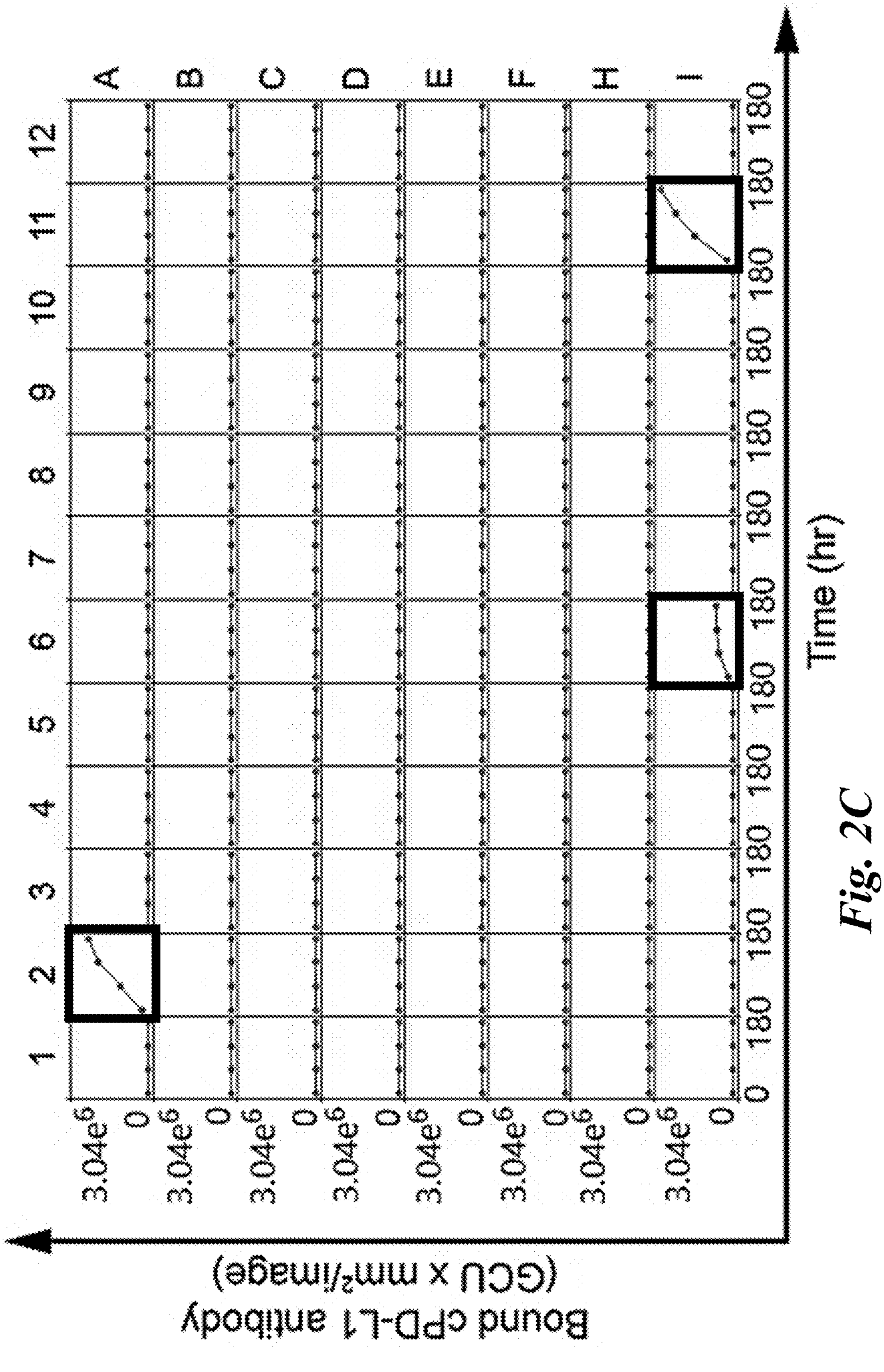
FIG. 2C is a kinetic graph showing quantitative binding of programmed death-ligand 1 (PD-L1) antibodies on BT549 cells expressing cPD-L1 at every 3-hour time point with the positive clones highlighted in red.
Figure 2D:
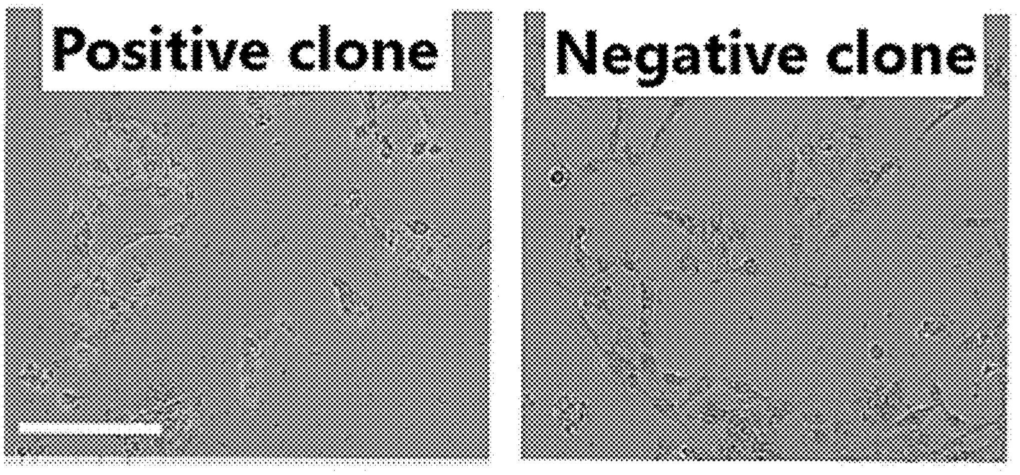
FIG. 2D are representative images (at 18 hours) of cPD-L1 antibody binding, with green fluorescent merged images of cPD-L1 expressing cells shown.

Among over 2.000 hybridomas, 154 clones were screened against membrane-localized cPD-L1 protein by the live cell-based antibody binding assay. Clonal antibodies were purified from supernatants and the same assays were rerun. FIG. 2C shows a kinetic graph of the quantitative binding of PD-L1 antibodies on BT549 cells expressing cPD-L1 at every 3-hour time point. The positive clones are highlighted in bolded boxes. FIG. 2D shows representative images (taken at 18 hours) of cPD-L1 antibody binding, with the green-fluorescent merged images of cPD-L1 expressing cells shown.

Figure 2E:
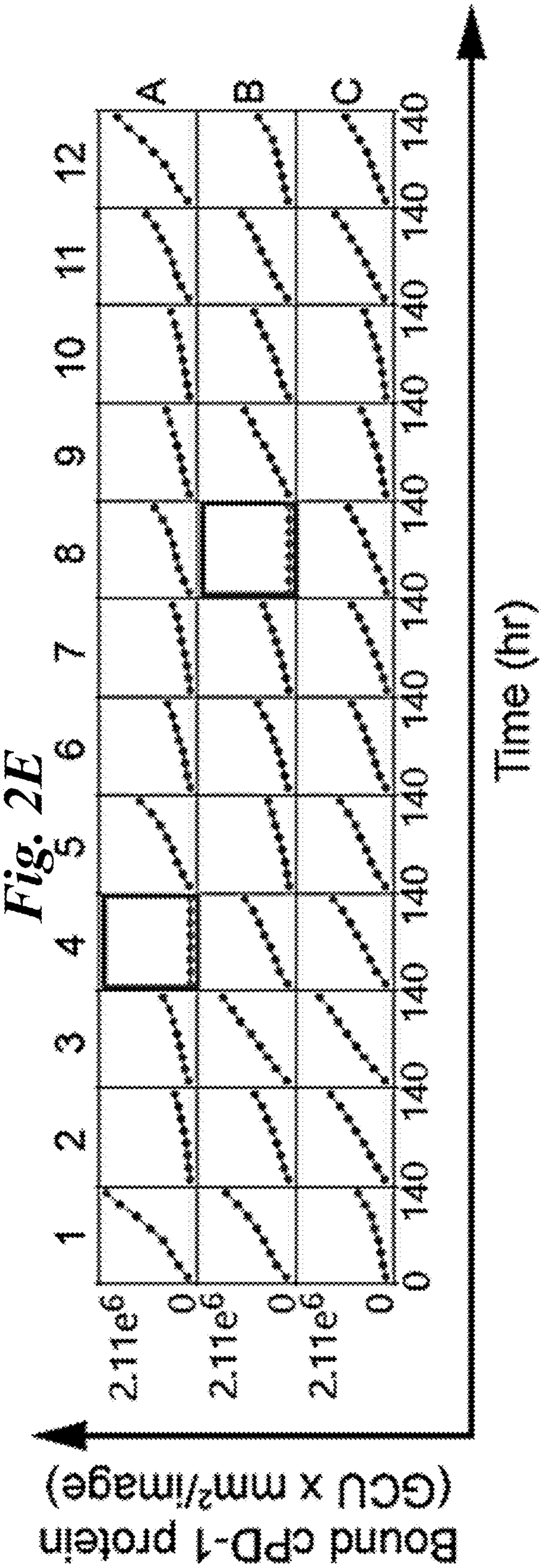
FIG. 2E is a kinetic graph showing quantitative binding of PD-1 protein on BT549 cells expressing cPD-L1 at every 3-hour time points after the addition of cPD-L1 antibodies. The positive clones that blocked the interaction of PD-L1/PD-1 proteins are highlighted in red.
Figure 2F:
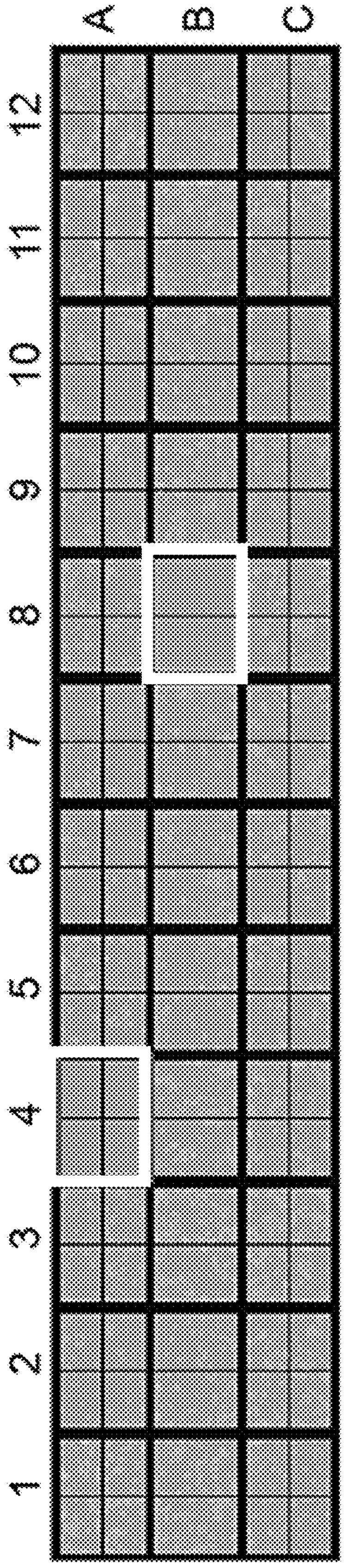
FIG. 2F are representative images (at 18 hours) of the cPD-L1 blockade, with green fluorescent merged images of cPD-L1 expressing cells shown. Note the lack of fluorescence due to the antibody binding to PD-L1 and blocking the interaction with cPD-1.

Ten of these clones had the ability to block cPD-L1/cPD-1 interaction. FIG. 2E shows a kinetic graph of the quantitative binding of PD-1 protein on BT549 cells expressing cPD-L1 at every 3-hour time points after the addition of cPD-L1 antibodies. The positive clones that blocked the interaction of PD-L1/PD-1 proteins are highlighted in black boxes. FIG. 2F shows representative images (taken at 18 hours) of the cPD-L1 blockade, with the green-fluorescent merged images of cPD-L1 expressing cells shown. Note the lack of fluorescence (in the squares highlighted by white boxes) due to the antibody binding to PD-L1 and blocking the interaction with cPD-1.

Representative positive clones are shown in FIGS. 2B-2F. Based on the specificity, binding affinity, and PD-1/PD-L1 blockade efficacy, mAb 3C, and mAb 12C were selected for further analysis.

Example 1B

Creation of Anti-Canine PD-L1 Monoclonal Antibody cPD-L1 A12C10E4 in CHO Cells

Monoclonal antibody cPD-L1 A12C10E4 (mAb A12C), was generated in CHO cells. A CHO cell line was originally derived from CHO-K1 (GenScript USA). Stable expression heavy and light chain DNA vectors were designed and optimized for CHO expression, with the heavy chain vector containing a puromycin resistance gene as a selectable marker and the light chain vector containing a blastocidin S resistance gene as a selectable marker, respectively (GenScript USA). The sequence of each completed construct was confirmed prior to initiating scale up experiments. The suspension CHO cells were cultured in a humidified 5% $CO_2$ incubator at 37° C. in a chemically defined media (Dynamis plus 8 mM glutamine. ThermoFisher). No serum or other animal-derived products were used in culturing the CHO cells.

Approximately 80 million suspension-adapted CHO cells, growing in Dynamis plus 8 mM glutamine media during the exponential growth phase, were transfected with HC:LC DNA in roughly a 1:1 molar ratio to a create a stable CHO cell line for the anti-canine PD-L1 monoclonal antibody cPD-L1 A12C10E4 (DNA construct contains the full-length sequence of the anti-canine PD-L1 monoclonal antibody cPD-L1 A12C10E4). After twenty-four hours, the transfected cells were counted and placed under selection for stable integration of anti-canine PD-L1 monoclonal antibody genes. The transfected cells were seeded into Dynamis plus 8 mM glutamine selection media containing low and then later at increasing amounts of both puromycin and blastocidin S concentrations in media at a cell density of $0.5\times10^6$ cells/mL in a shaker flask and incubated at 37° C. with 5% CO2. During a selection process, the cells were spun down and resuspended in fresh selection media every 2-3 days until the pool recovered its growth rate and viability. The cell culture was monitored for growth and titer.

The cells were grown to $2.5\times10^6$ cells per mL. At the time of harvest for cell banking, the viability was above 95%. The cells were then centrifuged, and the cell pellet was resuspended in the Dynamis plus 8 mM glutamine with 7.5% dimethyl sulfoxide (DMSO) to a cell count of $15\times10^6$ cells per mL per vial. Vials were cryopreserved for storage in liquid nitrogen.

A small-scale-up production was performed using the CHO cells as follows. The cells were scaled up for production in Dynamis plus 8 mM glutamine medium at 37° C. and fed every 2-4 days as needed, with Dynamis plus 8 mM glutamine medium supplemented with glucose and additional amino acids as necessary for approximately 14-21 days. The conditioned media supernatant harvested from the stable pool production run was clarified by centrifuge spinning. The protein was run over a Protein A (MabSelect, GE Healthcare, Little Chalfont, United Kingdom or Ampshere A3, JSR Life Sciences) column and eluted using a pH gradient. Filtration using a 0.2 μM membrane filter was performed.

The cell line was optionally further subcloned to monoclonality and optionally further selected for high titer anti-canine PD-L1 monoclonal antibody cPD-L1 A12C10E4 protein-expressing clones using the method of limiting dilution, a method known to those skilled in the art. After obtaining a high titer, anti-canine PD-L1 monoclonal antibody cPD-L1 A12C10E4 protein-expressing cell line, production of the cPD-L1 A12C10E4 protein was accomplished as described above in Dynamis plus 8 mM glutamine, to obtain a cell culture supernatant that containing the recombinant, CHO-made, cPD-L1 A12C10E4 antibody protein.

Example 2

Generation of the Canine PD-L1 Knock-In Mouse as a Pre-Clinical Model

Figure 3A:
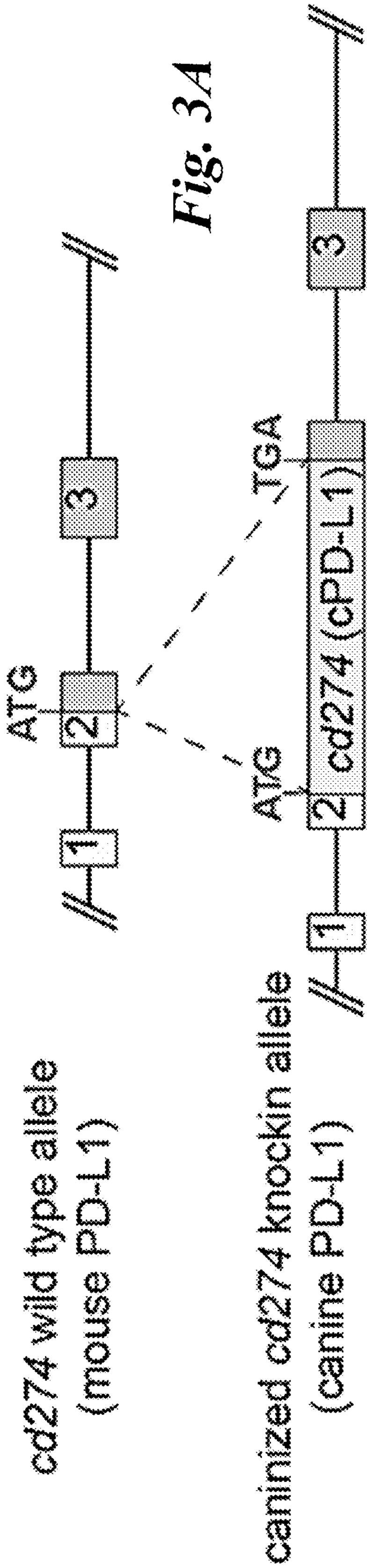
FIG. 3A is a schematic depicting the knock-in strategy of the mice containing the canine PD-L1 and PD-1 molecules (c57BL/c background).

To further assess the clinical use of the cPD-L1 antibody as an immunotherapeutic drug, its therapeutic efficacy was evaluated in an in vivo model. To do this. (C57BL/6 background) mice were generated that expressed a canine form of PD-L1. This was accomplished by generating cPD-L1 mice in which the mouse cd274 (PD-L1) gene was replaced with cPD-L1 using the CRISPR knock-in mouse strategy using a long single-strand DNA (ssDNA) donor and CRISPR ribonucleoproteins (FIG. 3A).

More specifically, the Efficient Additions with ssDNA inserts-CRISPR (Easi-CRISPR) method for human CD247 knock-in mouse generation was employed to create mice that expressed PD-L1 on the cell surface (C57BL/6 background) by replacing the mouse (I) 274 with canine CD274. See Quadros et al., Easi-CRISPR: a robust method for one-step generation of mice carrying conditional and insertion alleles using long single-stranded DNA (ssDNA) donors and CRISPR ribonucleoproteins. *Genome Biol* 18:92 (2017). Easi-CRISPR is a targeting strategy in which long ssDNA donors are injected with preassembled crRNA+tracrRNA+Cas9 ribonucleoprotein (ctRNP) complexes into mouse zygotes to generate targeted insertion alleles in the resulting live offspring (here replacing the mouse cd274 (PD-L1) gene with the canine PD-L1 gene). The long ssDNA (a full length of canine (D) 274 cDNA; NM_001291972) was injected with pre-assembled guide RNA (gRNA, CAGCAAATATCCTCATGTTTTGG (SEQ ID NO: 20)) and Cas9 ribonucleoprotein (ctRNP) complexes into mouse zygotes. The ssDNA and sgRNA were synthesized at Integrated DNA Technologies (IDT. Coralville, IA, USA). All animal experiments for the knock-in mouse generation performed were approved by the Purdue Animal Care and Use Committee (PACUC) at Purdue University (West Lafayette, IN). C57BL/6N female mice at 4 weeks of age (Envigo, Indianapolis, IN, USA) were superovulated and then mouse zygotes were obtained by mating C57BL/6N males with the superovulated females.

Pronuclei of one-cell stage fertilized mouse embryos were injected with 20 ng/μl Cas9 protein, 10 ng/μl sgRNA, and 5 ng/μl ssDNA. Microinjections and mouse transgenesis were performed as described (40). Mouse genomic DNA was extracted from the tail tip and then used for the genotyping (Primer set 1 forward, 5'-CCACTTGGTTCTACATGGCT-3" (SEQ ID NO: 21 Primer set 1 reverse, 5'-CCTCAGCCTGACACATTAGTT-3' (SEQ ID NO: 22); Primer set 2 forward, 5'-CCTGTCACCTCTGAACATGAA- 3' (SEQ ID NO: 23); Primer set 2 reverse, 5'-GACTAAGCTCTAGGTTGTCC-3' (SEQ ID NO: 24); Primer set 3 forward, 5'-GACTGGCTTTTAGGGCT-TATGT-3' (SEQ ID NO: 25); Primer set 3 reverse, 5'-ACACCCCACAAATTACTTCCATT-3' (SEQ ID NO: 26)) and sequencing (Primer set 3 forward, 5'-GACTGGCTTTTAGGGCTTATGT-3' (SEQ ID NO: 25); Primer set 3 reverse, 5'-ACACCCCACAAATTACTTC-CATT-3' (SEQ ID NO: 26)) to verify the location of insertion and DNA sequence of canine (I) 274.

Figure 3B:
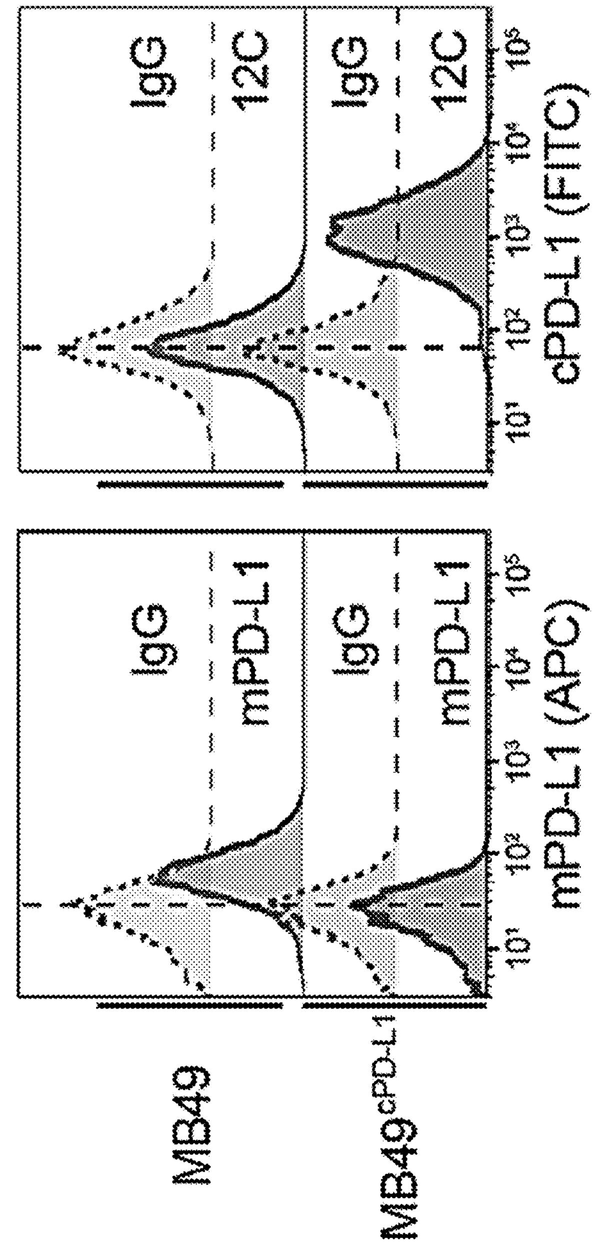
FIG. 3B is a validation of cPD-L1 protein expression in the MB49$^{cPD\text{-}L1}$ cells, showing flow cytometric analysis of membrane-located mPD-L1 and cPD-L1 protein in MB49 cells expressing cPD-L1 (MB49$^{cPD\text{-}L1}$) or MB49 parental cells.
Figure 3C:
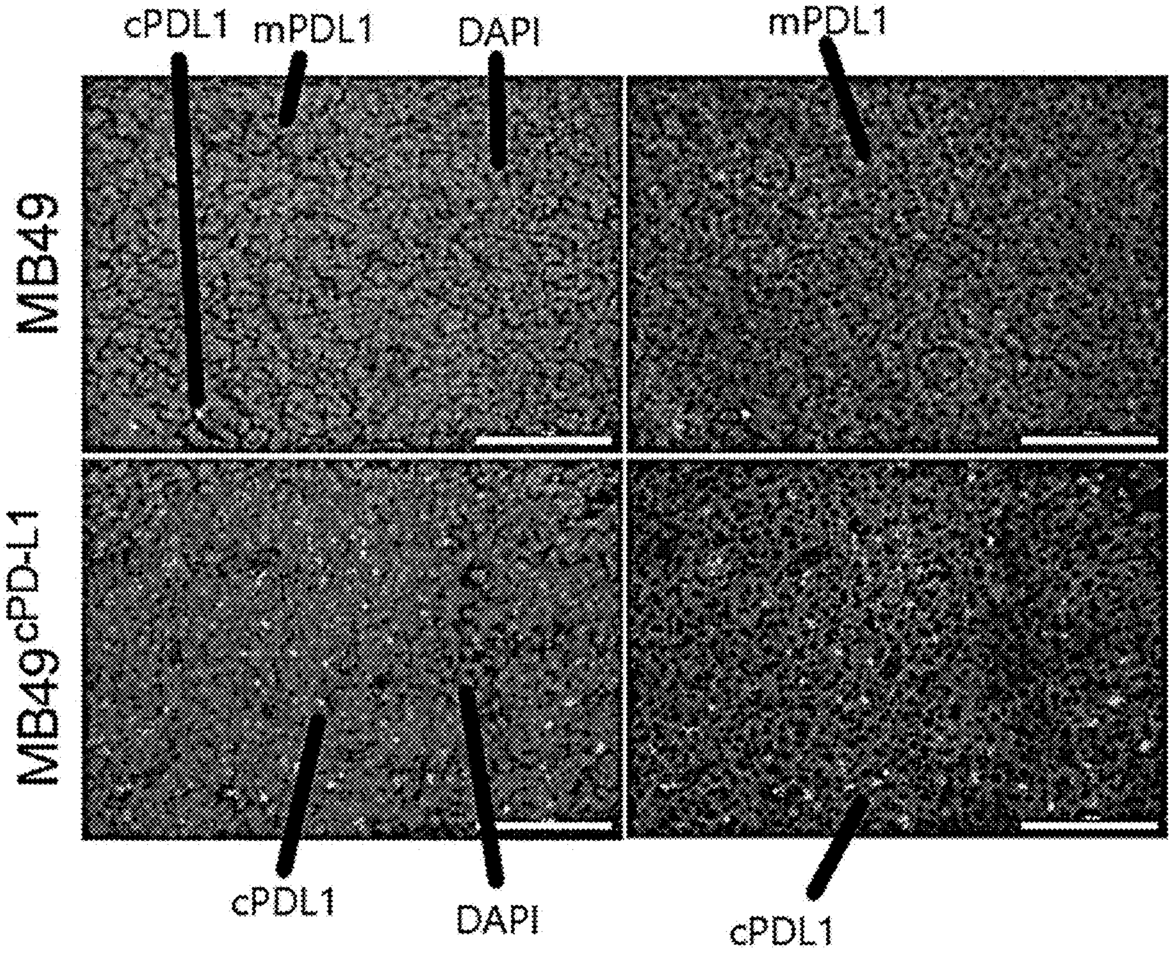
FIG. 3C shows immunofluorescence staining and protein expression patterns of mPD-L1 and cPD-L1 in MB49 or MB49$^{cPD\text{-}L1}$ tumor masses from the caninized PD-L1 mice (DAPI used for nuclear counterstaining; scale bar 100 μM).

To evaluate the therapeutic efficacy of the cPD-L1 antibody in a syngeneic animal model, a mouse bladder cancer MB49 cell line was generated that expressed cPD-L1 ($MB49^{cPD-L1}$) by knocking out mPD-L1 and re-expressing cPD-L1 (FIGS. 3B and 3C). FIG. 3B shows a flow cytometric analysis of membrane located cPD-L1 protein in MB49 cells expressing cPD-L1 ($MB49^{cPD-L1}$).

Example 3

Interaction of cPD-1 or mPD-1 Protein with cPD-L1 or mPD-L1 In Vitro With or Without cPD-L1 Antibody (mAb 12C) Treatment Although $MB49^{cPD-L1}$ and the canine PD-L1 mice expressed cPD-L1 protein instead of mPD-L1 protein, the canine PD-L1 mice expressed mouse PD-1 protein. Accordingly, it was first examined if the cPD-L1 protein interacts with mPD-1 protein before evaluating the therapeutic efficacy of cPD-L1 antibody in the canine PD-L1 mice.

To measure immune receptor and ligand interaction. His-tagged canine or mouse PD-L1 protein (cPD-L1-His or mPD-L1-His, respectively) were incubated on a nickel-nitriloacetic acid (Ni-NTA) coated 96-well plates. The plates were then incubated with recombinant Fc-tagged protein for 1 hour, and the secondary antibodies used were anti-human or canine IgG Fc-specific Alexa 488 dye conjugate (Jackson ImmunoResearch Inc., West Grove, PA). Fluorescence intensity of Alexa fluor 488 dye was measured by microplate reader (Synergy Neo2; BioTek Instruments, Inc., Winooski, VT).

Figure 3D:
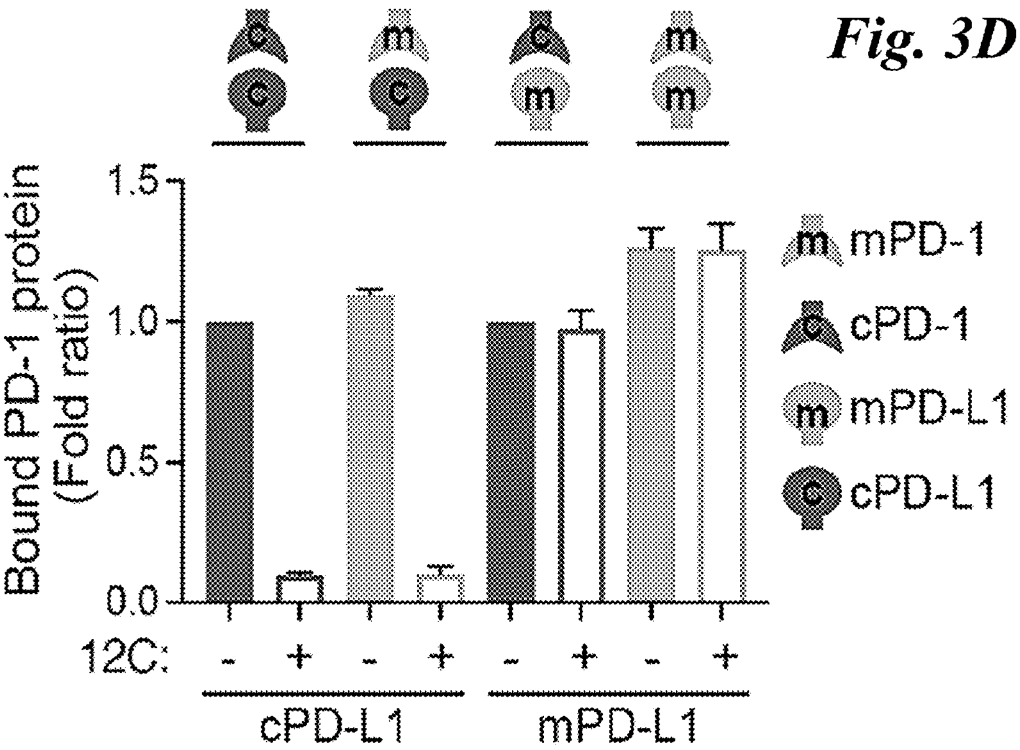
FIG. 3D shows a graph indicative of the interaction of canine PD-1 (cPD-1) or mouse PD-1 (mPD-1) protein with cPD-L1 or mouse PD-L1 (mPD-L1) protein with or without canine PD-L1 antibody (12C). Histidine (His)-tagged canine or mPD-L1 protein was immobilized on the nickel-nitriloacetic acid (Ni-NTA) 96-well plate and horseradish peroxidase (HRP)-conjugated anti-human IgG Fc-specific secondary with mPD-1-hFc or cPD-1-hFc protein was added. $OD_{450}$ was measured to quantify the amount of bound PD-1 protein.
Figure 3E:
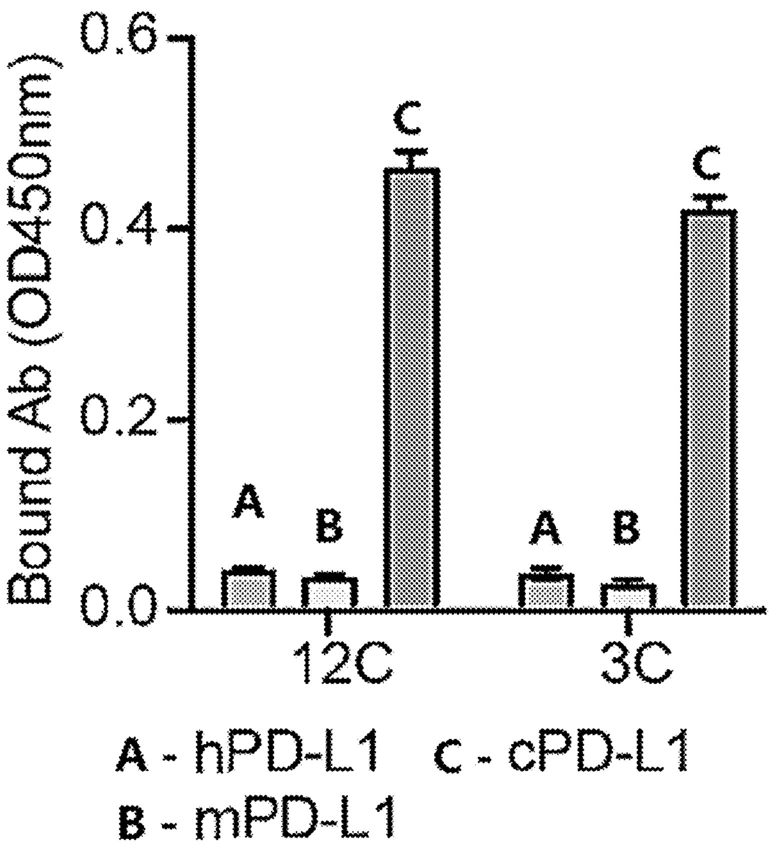
FIG. 3E shows the binding of cPD-L1 antibodies, 12C and 3C, with human PD-L1 (hPD-L1), mPD-L1, and cPD-L1 proteins. His-tagged human PD-L1, mPD-L1, or cPD-L1 protein was immobilized on the Ni-NTA 96-well plate, and anti-cPD-L1 Abs, 12C or 3C, with HRP-conjugated anti-canine IgG-specific secondary was added. $OD_{450}$ was measured to quantify the amount of bound PD-L1 antibodies (Ab=antibody).

The binding of cPD-L1 and mPD-1 was similar to the cognate cPD-L1 and cPD-1 pair (OD450 was measured to quantify the amount of bonded PD-1 protein (FIG. 3D)). Consistently, the cPD-L1 antibody (mAb 12C) efficiently blocked cPD-L1/mPD-1 interaction as well as cPD-L1/cPD-1 but did not block mPD-L1/mPD-1 or mPD-L1/cPD-1 interactions (as the present cPD-L1 antibodies did not recognize mPD-L1) (FIGS. 3D and 3E).

Example 3B

Interaction of cPD-1 or mPD-1 Protein with cPD-L1 or mPD-L1 In Vitro With or Without cPD-L1 Antibody (mAb cPD-L1 A12C10E4) Treatment Although $MB49^{cPD-L1}$ and the canine PD-L1 mice expressed cPD-L1 protein instead of mPD-L1 protein, the canine PD-L1 mice expressed mouse PD-1 protein. Accordingly, it is first examined if the cPD-L1 protein interacts with mPD-1 protein before evaluating the therapeutic efficacy of cPD-L1 antibody in the canine PD-L1 mice.

To measure immune receptor and ligand interaction, His-tagged canine or mouse PD-L1 protein (cPD-L1-His or mPD-L1-His, respectively) are incubated on a nickel-nitriloacetic acid (Ni-NTA) coated 96-well plates. The plates are then incubated with recombinant Fc-tagged protein for 1 hour, and the secondary antibodies used are anti-human or canine IgG Fc-specific Alexa 488 dye conjugate (Jackson ImmunoResearch Inc., West Grove, PA). Fluorescence intensity of Alexa fluor 488 dye is measured by microplate reader (Synergy Neo2; BioTek Instruments, Inc., Winooski, VT).

The binding of cPD-L1 and mPD-1 is similar to the cognate cPD-L1 and cPD-1 pair (OD450 was measured to quantify the amount of bonded PD-1 protein). Consistently, the cPD-L1 antibody (mAb cPD-L1 A12C10E4) is expected to efficiently block cPD-L1/mPD-1 interaction as well as cPD-L1/cPD-1 but not block mPD-L1/mPD-1 or mPD-L1/cPD-1 interactions (as the present cPD-L1 antibodies do not recognize mPD-L1).

Example 4

Evaluation of Therapeutic Efficacy of cPD-L1 Antibodies in Canine PD-L1 Mice All procedures with the canine PD-L1 B mice (C57BL/c background strain; 6- to 8-week-old) were conducted under guidelines approved by the PACUC at Purdue University. Mice were divided according to the mean tumor volume in each group. $MB49^{cPD-L1}$ ($2\times10^5$ cells in 25 μL of medium mixed with 25 μL of Matrigel Basement Membrane Matrix (BD Biosciences, San Jose. CA)) were injected into the flank of the caninized PD-L1 mice.

Following the establishment of $MB49^{cPD-L1}$ tumors in the cPD-L1 mice, the mice were divided into a control group, a mAb 12C treatment group, and a mAb 3C treatment group, with mice within each subset divided according to mean tumor volume in each group.

For treatment with antibodies, 100 μg of cPD-L1 antibody (mAb 12C or mAb 3C clone) or control mouse IgG (BioXCell) was injected intraperitoneally on days 4, 6, 8, 10, and 12 after tumor cell inoculation when tumor size was approximately 30 to 40 $mm^3$. Tumors were measured every other day with a caliper, and tumor volume was calculated using the following formula:

$$\pi/6\times\text{length}\times\text{width}^2.$$

Figure 3F:
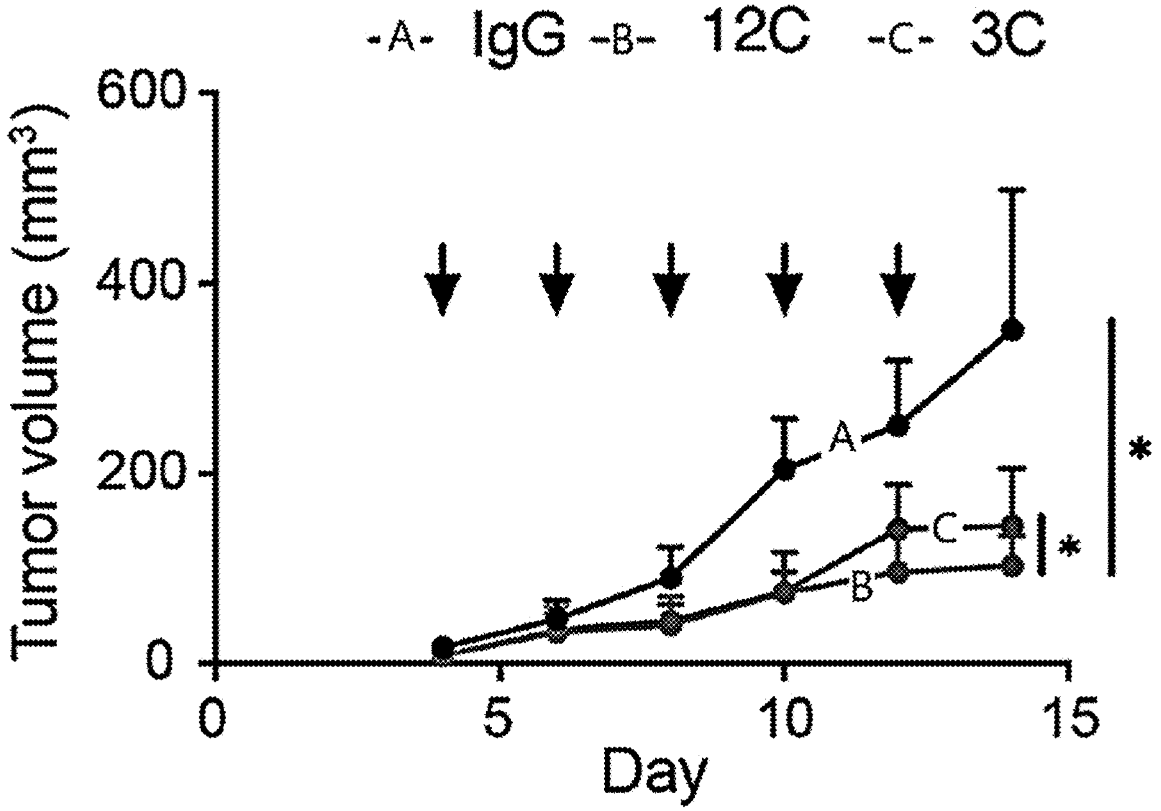
FIG. 3F shows data related to tumor growth of MB49$^{cPD\text{-}L1}$ in the caninized PD-L1 mice treated with cPD-L1 antibody, 12C or 3C. The IgG isotype of 12C and 3C antibodies is mouse IgG1, which is equivalent to human IgG4. Tumors were measured at the indicated time points and dissected at the endpoint (n=8 per group).
Figure 3F:

Tumors were dissected at the endpoint (n=8 per group) (FIG. 3F).

Figure 3G:
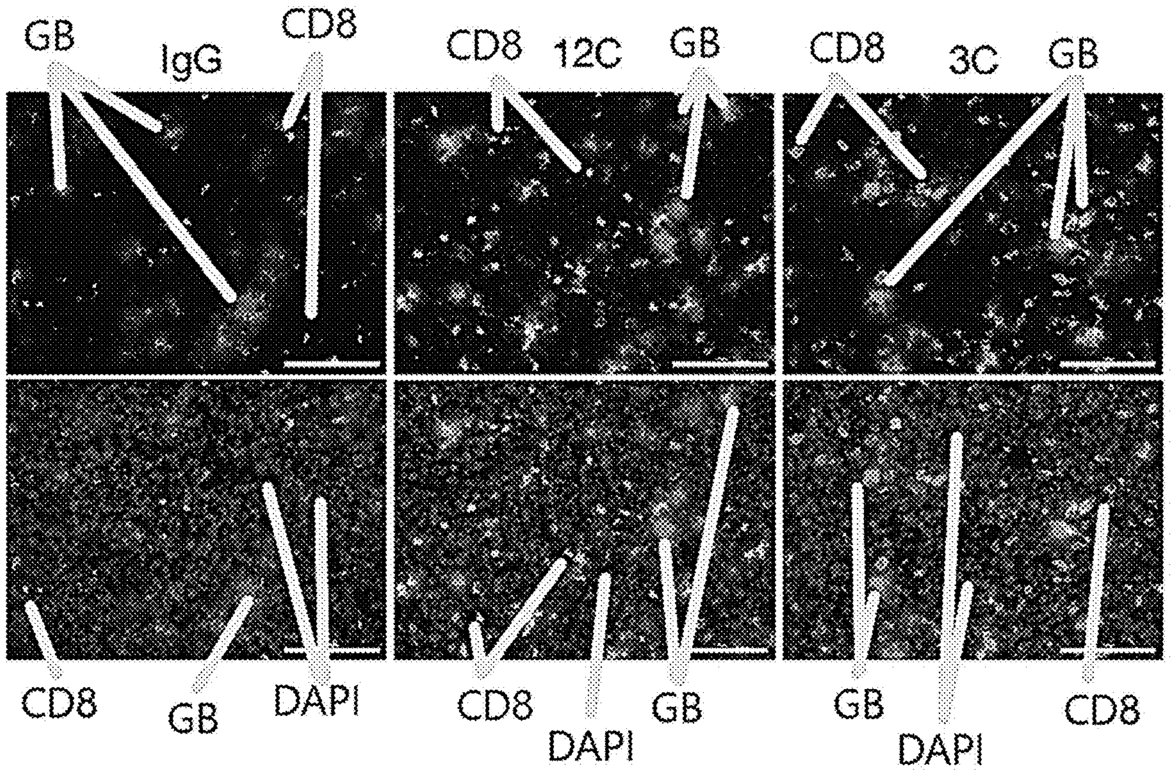
FIG. 3G shows representative images of immunofluorescence staining of the protein expression pattern of CD8 and granzyme B in MB49 tumor masses from IgG-, 12C-, or 3C-treated mice. DAPI was used for nuclear counterstaining. Scale bar, 100 μm.
Figure 3H:
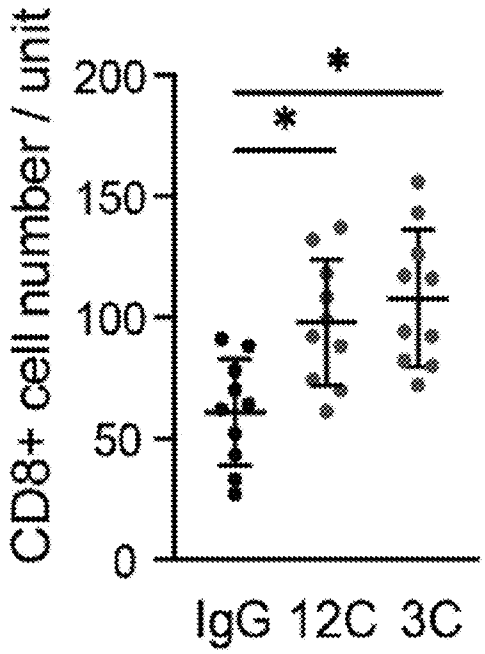
FIGS. 3H and 3I show quantification of CD8 (FIG. 3H) and granzyme B (FIG. 3I) in the immunofluorescence staining and protein expression patterns using Gen5 software (BioTek, Winooski, VT), n=10.
Figure 3I:
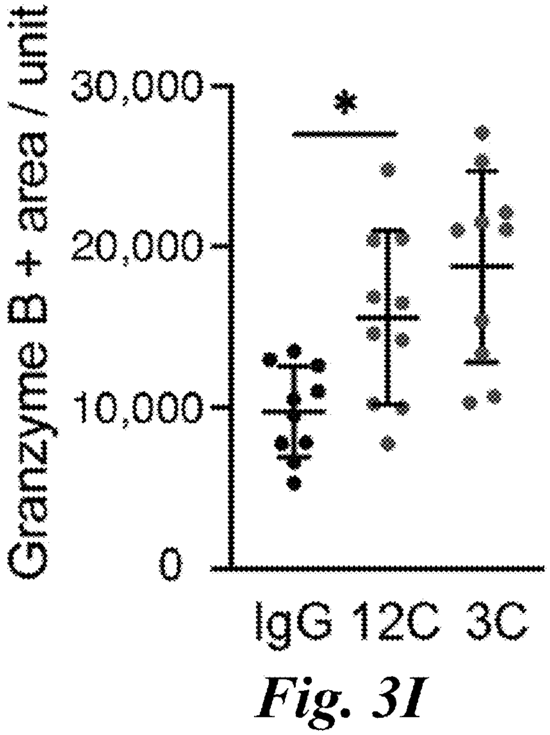

Immunofluorescence staining was performed of the protein expression pattern of CD8 and granzyme B in the MB49 tumor masses from the IgG-treated mice (control group), 12C-treated mice, and the 3C-treated mice (FIGS. 3G-3I). Tumor masses were frozen in an optimal cutting temperature (OTC) block immediately after excision. Cryostat sections of 5 μm thickness were attached to saline-coated slides. Cryostat sections were fixed with 4% paraformaldehyde for 30 minutes at room temperature and blocked with blocking solution (1% bovine serum albumin. 2% donkey and/or chicken serum, and 0.1M phosphate buffered saline (PBS)) at room temperature for 30 minutes. Samples were stained with primary antibodies against CD8 and granzyme B overnight at 4° C. followed by secondary antibodies at room temperature for 1 hour. Nuclear staining was performed with Hoechst 33342 (Thermo Fisher Scientific, Waltham, MA). The stained sections were visualized by automated microscopy (Lionheart LX; BioTek Instruments, Inc., Winooski, VT). Granzyme B positive area and the number of CD8 positive cytotoxic T lymphocytes (CTLs) were assessed per high power field (200×). Fourteen randomly chosen microscope fields from 4 serial sections in each tissue block were examined for the number of CD8 positive CTL and granzyme B positive areas for each tissue.

CD8 (FIG. 3H) and granzyme B (FIG. 3I) were also quantified using BioTek Gen5 Data Analysis Software (Agilent Technologies, Santa Clara, CA) (n=10). The treatment with either mAb 12C or mAb 3C significantly reduced the tumor size (FIG. 3F) and increased the number of infiltrating cytotoxic T cells relative to mice treated with control IgG as measured by CD8+ and granzyme B expression (FIGS. 3G-3I).

Figure 3J:
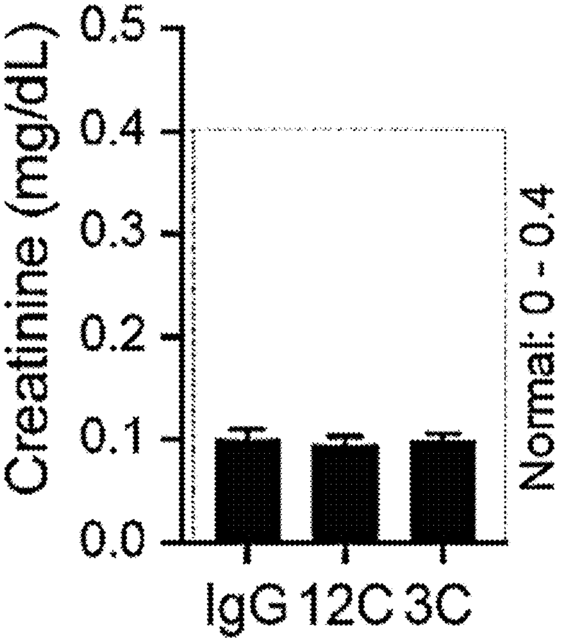
FIGS. 3J and 3K are graphs representative of the effect of treatment on the PD-L1 mice, with mice kidney (FIG. 3J) and liver (FIG. 3K) functions measured at the end of the experiments. ALT, alanine aminotransferase. Treatment with the PD-L1 antibody did not affect kidney function (serum creatinine) or liver enzyme activity (ALT=alanine aminotransferase), measured in blood collected at the end of the experiment.
Figure 3K:
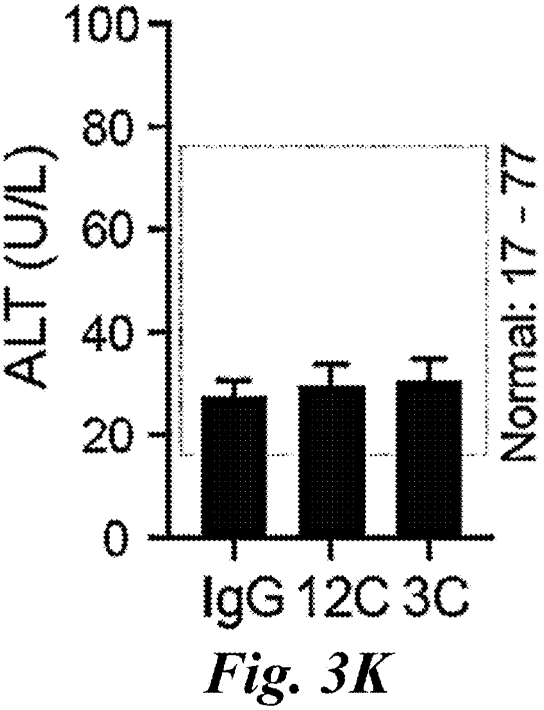

Additionally, the effect of treatment on the PD-L1 mice was assessed at the conclusion of treatment by measuring mice kidney (FIG. 3J) and liver (FIG. 3K) functions. The data support that both cPD-L1 antibodies enhanced anti-tumor immunity in the PD-L1 syngeneic mouse model and demonstrated good safety profiles as the mice maintained body weight, and there was no changes to kidney function as assessed by serum creatinine or liver enzyme activity. The in vitro and in vivo validation results indicated that the cPD-L1 antibodies that recognized canine PD-L1 effectively inhibited the PD-1/PD-L1 pathway and enhanced mouse anti-tumor immunity.

Example 4B

Evaluation of Therapeutic Efficacy of cPD-L1 Antibodies in Canine PD-L1 Mice All procedures with the canine PD-L1 B mice (C57BL/c background strain; 6- to 8-week-old) are conducted under guidelines approved by the PACUC at Purdue University. Mice are divided according to the mean tumor volume in each group. MB49$^{cPD\text{-}L1}$ ($2\times10^5$ cells in 25 μL of medium mixed with 25 μL of Matrigel Basement Membrane Matrix (BD Biosciences, San Jose, CA)) and are injected into the flank of the caninized PD-L1 mice.

Following the establishment of MB49$^{cPD\text{-}L1}$ tumors in the cPD-L1 mice, the mice are divided into a control group, a cPD-L1 A12C10E4 treatment group, with mice within each subset divided according to mean tumor volume in each group.

For treatment with antibodies, 100 μg of cPD-L1 antibody (mAb cPD-L1 A12C10E4) or control mouse IgG (BioXCell) are injected intraperitoneally on days 4, 6, 8, 10, and 12 after tumor cell inoculation when tumor size is approximately 30 to 40 $mm^3$. Tumors are measured every other day with a caliper, and tumor volume is calculated using the following formula:

$$\pi/6\times\text{length}\times\text{width}^2.$$

Tumors are dissected at the endpoint (n=8 per group).

Immunofluorescence staining is performed of the protein expression pattern of CD8 and granzyme B in the MB49 tumor masses from the IgG-treated mice (control group), cPD-L1 A12C10E4-treated mice. Tumor masses are frozen in an optimal cutting temperature (OTC) block immediately after excision. Cryostat sections of 5 μm thickness are attached to saline-coated slides. Cryostat sections are fixed with 4% paraformaldehyde for 30 minutes at room temperature and blocked with blocking solution (1% bovine serum albumin, 2% donkey and/or chicken serum, and 0.1M phosphate buffered saline (PBS)) at room temperature for 30 minutes. Samples are stained with primary antibodies against CD8 and granzyme B overnight at 4° C., followed by secondary antibodies at room temperature for 1 hour. Nuclear staining is performed with Hoechst 33342 (Thermo Fisher Scientific, Waltham, MA). The stained sections are visualized by automated microscopy (Lionheart LX; BioTek Instruments, Inc., Winooski, VT). Granzyme B positive area and the number of CD8 positive cytotoxic T lymphocytes (CTLs) are assessed per high power field (200×). Fourteen randomly chosen microscope fields from 4 serial sections in each tissue block are examined for the number of CD8 positive CTL and granzyme B positive areas for each tissue.

CD8 and granzyme B are quantified using BioTek Gen5 Data Analysis Software (Agilent Technologies, Santa Clara, CA) (n=10). The treatment with mAb cPD-L1 A12C10E4 is expected to significantly reduce the tumor size and increase the number of infiltrating cytotoxic T cells relative to mice treated with control IgG as measured by CD8+ and granzyme B.

Additionally, the effect of treatment on the PD-L1 mice is assessed at the conclusion of treatment by measuring mice kidney and liver functions. The data is expected to indicate that the cPD-L1 A12C10E4 antibody enhances anti-tumor immunity in the PD-L1 syngeneic mouse model and demonstrates a good safety profile, maintaining mice body weight, and causing no change to kidney function as assessed by serum creatinine or liver enzyme activity. The in vitro and in vivo validation results are expected to indicate that the cPD-L1 A12C10E4 antibody recognizes the canine PD-L1 effectively and will inhibit the PD-1/PD-L1 pathway and enhance mouse anti-tumor immunity.

Example 5

Characterization of the Caninized PD-L1 Chimeric Antibody

Figure 4A:
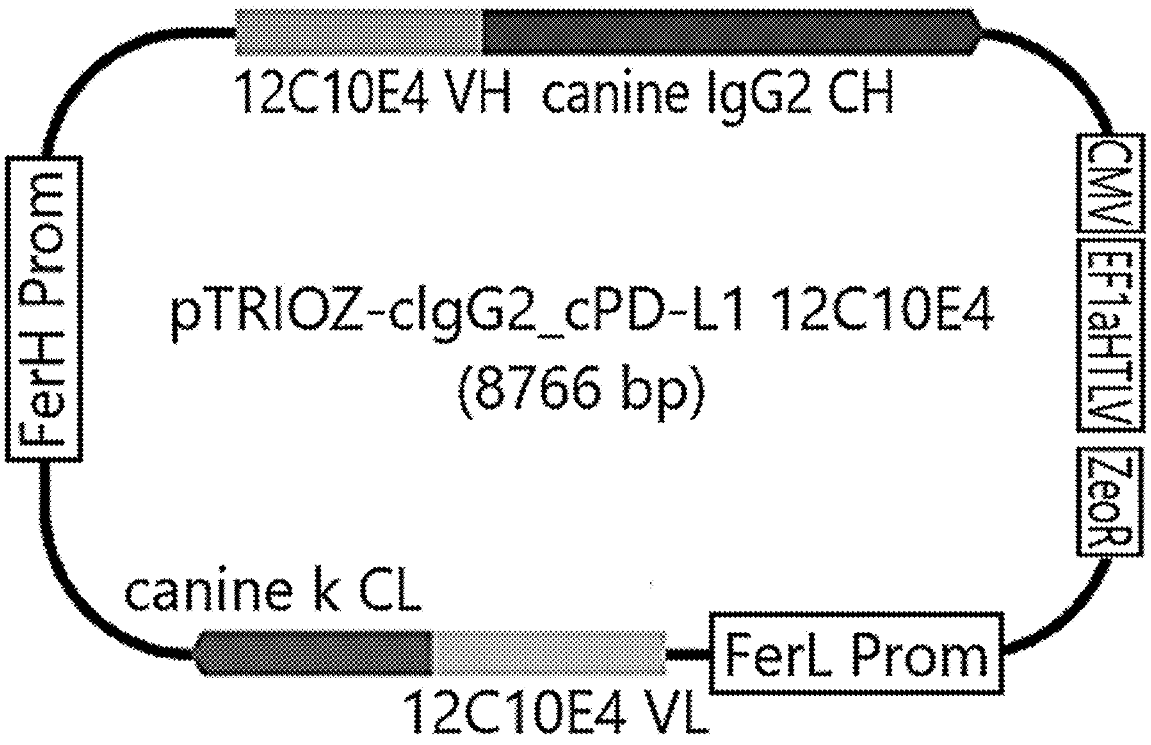
FIGS. 4A-4F show the quality attributes of purified anti-cPD-L1, 1210E4 (12C) chimeric antibody, with FIG. 4A showing a schematic of the cPD-L1, 12C10E4 chimeric antibody expression construct, pTRIOZ-cIgG2-cPD-L1 12C10E4.

For the clinical use of canine PD-L1 antibodies in dogs, mAb 12C was caninized by replacing the mouse constant domain with canine IgG2 (equivalent to human IgG1) constant domain Fc fragments. Briefly, full-length variable heavy (VH) and variable light (VL) RNA transcripts obtained from hybridoma clones were sequenced by 5'/3' rapid amplification of cDNA ends (RACE) and codon-optimized for CHO VL and VH chains were cloned into the pTRIOZ-cIgGB-ck vector (InvivoGen, San Diego, CA, USA), a vector designed for high-yield production of whole monoclonal antibodies with the use of a single plasmid. Then the constant light and heavy chains were replaced with canine kappa light constant chain and canine IgG2 heavy constant chains: pTRIOZ-cIgG2-12C10E4. FIG. 4A shows a schematic representation of a cPD-L1 (mAb 12C) chimeric antibody expression construct (pTRIOZ-cIgG2-cPD-L1 mAb 12C). The cPD-L1 A12C10E4 chimeric antibody construct follows the same schematic representation as shown in FIG. 4A, though it was expressed in cells via recombinant means once the full sequence from 12C was known using methods known to those skilled in the art using the cell line development Example 1B. The chimeric cPD-L1 antibody retained the cPD-L1 binding VH and VL chains of the mouse hybridoma.

Plasmids encoding the 12C chimeric antibody, pTRIOZ cIgG2 12C10E4, were transfected into ExpiCHO-S cells following the transfection kit instructions (GIBCO, A29133). ExpiCHO-S cells were cultured with ExpiCHO Expression Medium (Thermo Fisher Scientific, Waltham, MA) in a shaker incubator set at 120 rpm, 37° C. and 8.0% $CO_2$. Cells were collected 10 days post-transfection at 4.000× g and 4° C. for 20 minutes. The antibody supernatant passed through a 0.22-μm filter and neutralized with 10×PBS buffer (Lonza™ BioWhittaker™ Phosphate Buffered Saline (10×), BW17-517Q). The antibody supernatant was pre-incubated with protein A agarose for 2 hours. The agarose A-conjugated antibody were applied to the column (BioRad poly-prep chromatography column. #731-1550). The column was washed with low-endotoxin PBS (Lonza™ BioWhittaker™ Dulbecco's Phosphate Buffered Saline (1×) w/o Calcium and Magnesium, BW17512F24). The bound antibody was eluted with elution buffer (ThermoFisher Scientific, Waltham, MA; Elution Buffers, 0.1M Glycin-HCl. pH 2.8. #21004) into Neutralization Buffer (Tris HCl, 1M, BP1757-500). The purified antibody was concentrated and buffer exchanged with PBS, pH 7.0. The antibody concentration of 12C10E4 was determined by UV absorbance at 280 nm.

Figure 4B:
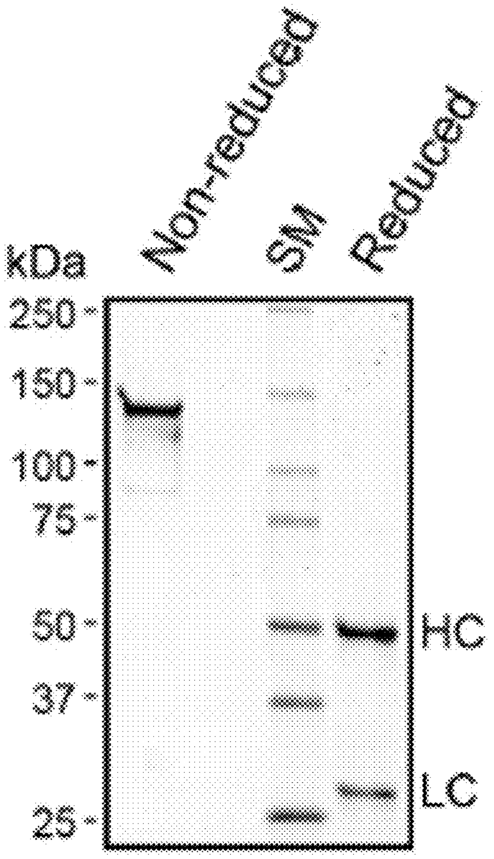
Figure 4C:
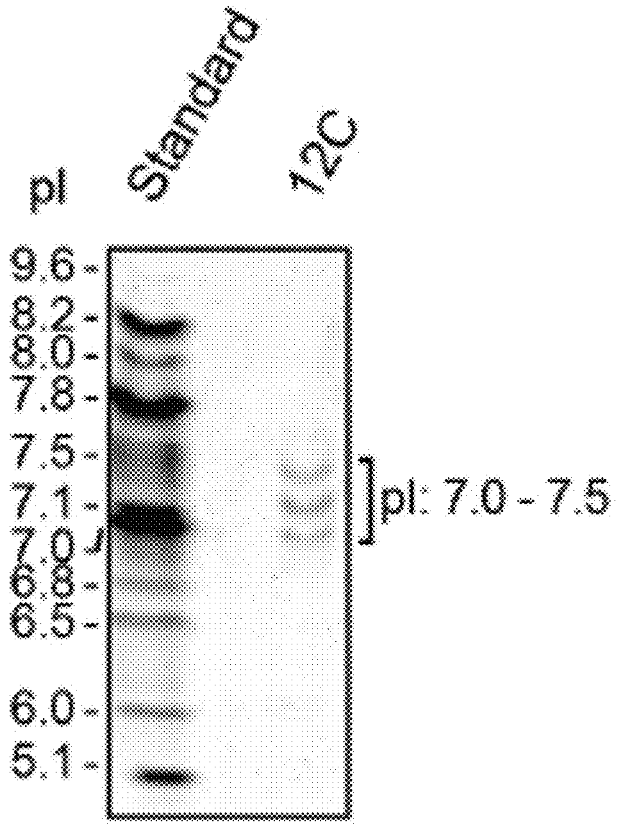

To monitor batches during antibody production of 12C10E4, attributes of the purified chimeric antibodies, such as purity, isoelectric point (pI) value, amino acid sequence, and N-glycomic profile were assessed (FIGS. 4B-4F). Briefly, purity and pI values were determined by a sodium dodecyl sulfate-polyacrylamide gel electrophoresis (SDS-PAGE) analysis and isoelectric focusing (IEF), respectively. SDS-PAGE or IEF gels were purchased from Bio-Rad Laboratories (Hercules, CA) or ThermoFisher Scientific (Waltham, MA). SDS-PAGE was performed of the 12C chimeric antibody purity under nonreducing and reducing (2-mercaptoethanol) conditions according to the manufacturer's protocol (FIG. 4B). IEF and Coomassie blue staining were also performed according to the manufacturer's protocol. The SDS-PAGE, image acquisition and quantitation of band intensity were performed using Odyssey CLx infrared imaging system (L1-COR Biosciences, Lincoln, NE). FIG. 4B shows SDS-PAGE analysis and FIG. 4C shows IEF analysis of the 12C chimeric antibody.

A peptide mapping comparison for cPD-L1 chimeric antibody (each mAb 12C and cPD-L1 A12C10E4 batch) was also performed to assess amino acid sequence. Briefly, the antibody was enzymatically digested with trypsin on S-trap micro columns from Protifi (Farmingdale, NY) after reduction and alkylation. Peptides were then separated and analyzed by reverse phase liquid chromatography-tandem mass spectrometry (RP-LC-MS/MS) using a Q Exactive HF Hybrid Quadrupole-Orbitrap MS equipped with a Nanospray Flex Ion Source and coupled with a Dionex UltiMate 3000 RSLC Nano System (ThermoFisher Scientific, Waltham, MA). The resultant mass spectrometric data was analyzed using the PEAK PTM workflow in the PEAKS X PRO Studio 10.6 software package from Bioinformatics Solutions Incorporated to map the detected MS1 and MS2 ions to the amino acid sequence of antibody. See Ma et al., PEAKS: powerful software for peptide de novo sequencing by tandem mass spectrometry. *Rapid Commun Mass Spectrom* 17:2337-2342 (2003). The peptide mapping analysis was performed in the Proteomics core facility at Purdue University (West Lafayette, IN). LC/MS-MS data were used for mapping glycosylation (0.98 Da) of asparagine (N) and glutamine (Q) residues of the mapped antibody sequences.

Figure 4D:
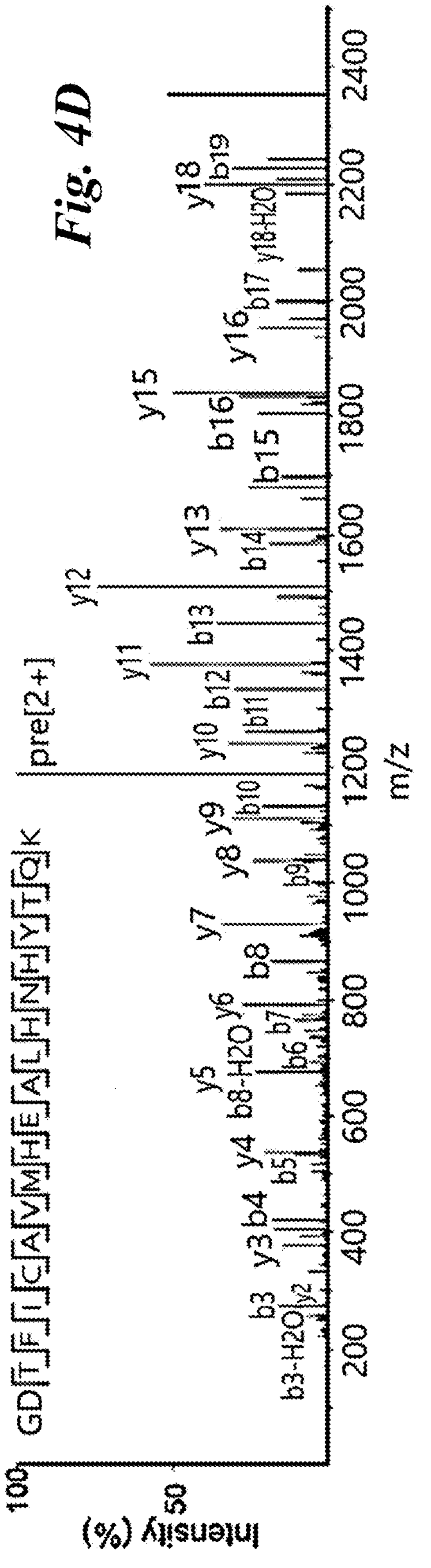

The sequence coverage of heavy and light chains was 100% (453 of 453 amino acids) and 98.2% (223 of 227 amino acids), respectively for 12C10E4, which is a strong positive indicator for SEQ ID NO: 14 being present (FIG. 4D). The chimeric cPD-L1 antibody retained the cPD-L1 binding VH and VL chains of the mouse hybridoma.

Figure 4E:
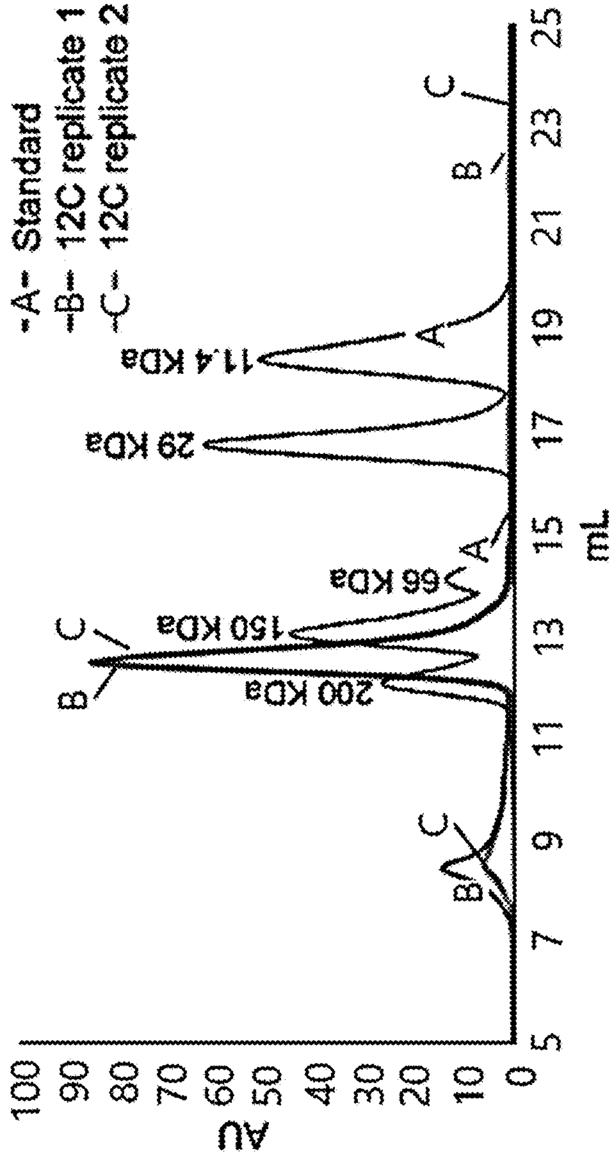

Size exclusion chromatography (SEC) analysis was performed on the 12C and cPD-L1 A12C10E4 chimeric antibodies to detect antibody aggregates and monomers. The AKTA Pure 150 M (Cytiva, Marlborough, MA) and Superdex 200 Increase 10/300 GL column (Cytiva. Marlborough, MA) were used to analyze antibodies at a flow rate 0.3 ml/min for 135 minutes. Elution was monitored using UV absorption at 280 nm and data were processed by Unicorn 7 software (Cytiva. Marlborough, MA). The SEC analysis was performed in the Molecular Evolution, Protein Engineering, and Production core facility at Purdue University (West Lafayette. IN). FIG. 4E shows SEC analysis results for 12C10E4.

Figure 4F:
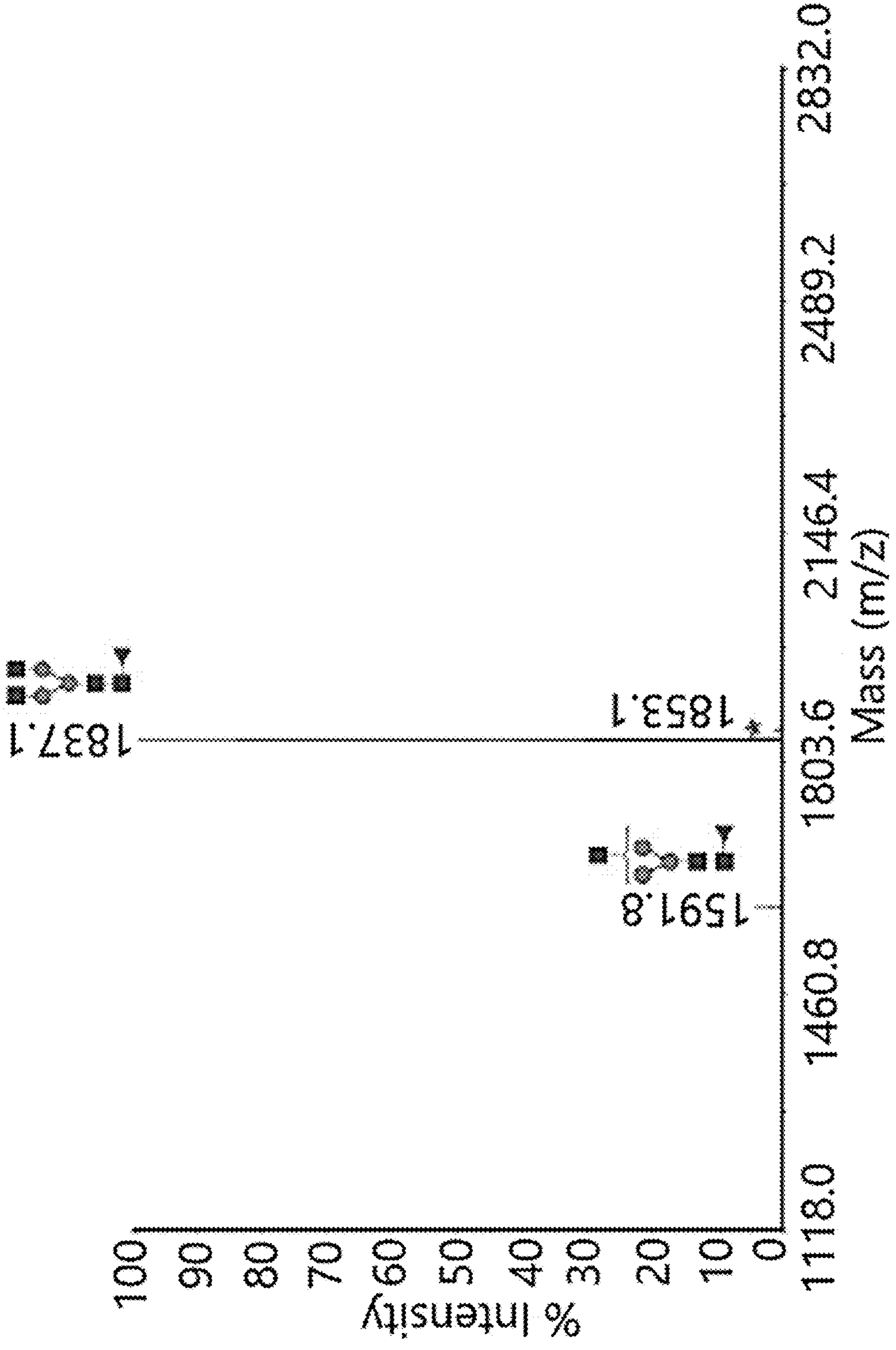

In addition, matrix-assisted laser desorption/ionization time-of-flight mass spectrometry profiling (MALDI-TOF MS profiling) of premethylated N-glycans released from PNGase F-treated the 12C and cPD-L1 A12C10E4 chimeric antibodies was performed by methods described in Shajahan et al., Glycomic and glycoproteomic analysis of glycoproteins-a tutorial, *Anal Bioanal Chem* 409:4483-4505 (2017). Briefly. N-glycans of 12C10E4 and cPD-L1 A12C10E4 antibodies were released by treating the reduced and alkylated protein with PNGase F. The released N-glycan fractions were then permethylated. The permethylated N-glycans were evaluated by Matrix-assisted laser desorption/ionization-mass spectrometry (MALDI-MS) using the AB SCIEX TOF/TOF 5800 mass spectrometer (Applied Biosystem/MDS Analytical Technologies, Sunnyvale, CA). The structural assignments of the N-glycans were based on molecular weight and followed the principles of the N-glycan bio-synthesis pathway. The carbohydrate analysis was performed at the Complex Carbohydrate Research Center, the University of Georgia (supported by NIH R24GM137782 grant). FIG. 4F shows MALD-MS profiling results for 12C10E4.

Example 6

Caninized cPD-L1 Chimeric Antibody Binding and Blockade Assays

The caninized cPD-L1 chimeric antibody was assessed using a cell-free cPD-L1/cPD-1 blockade assay pursuant to known protocols. See Li et al. (2018), supra.

Figure 5A:
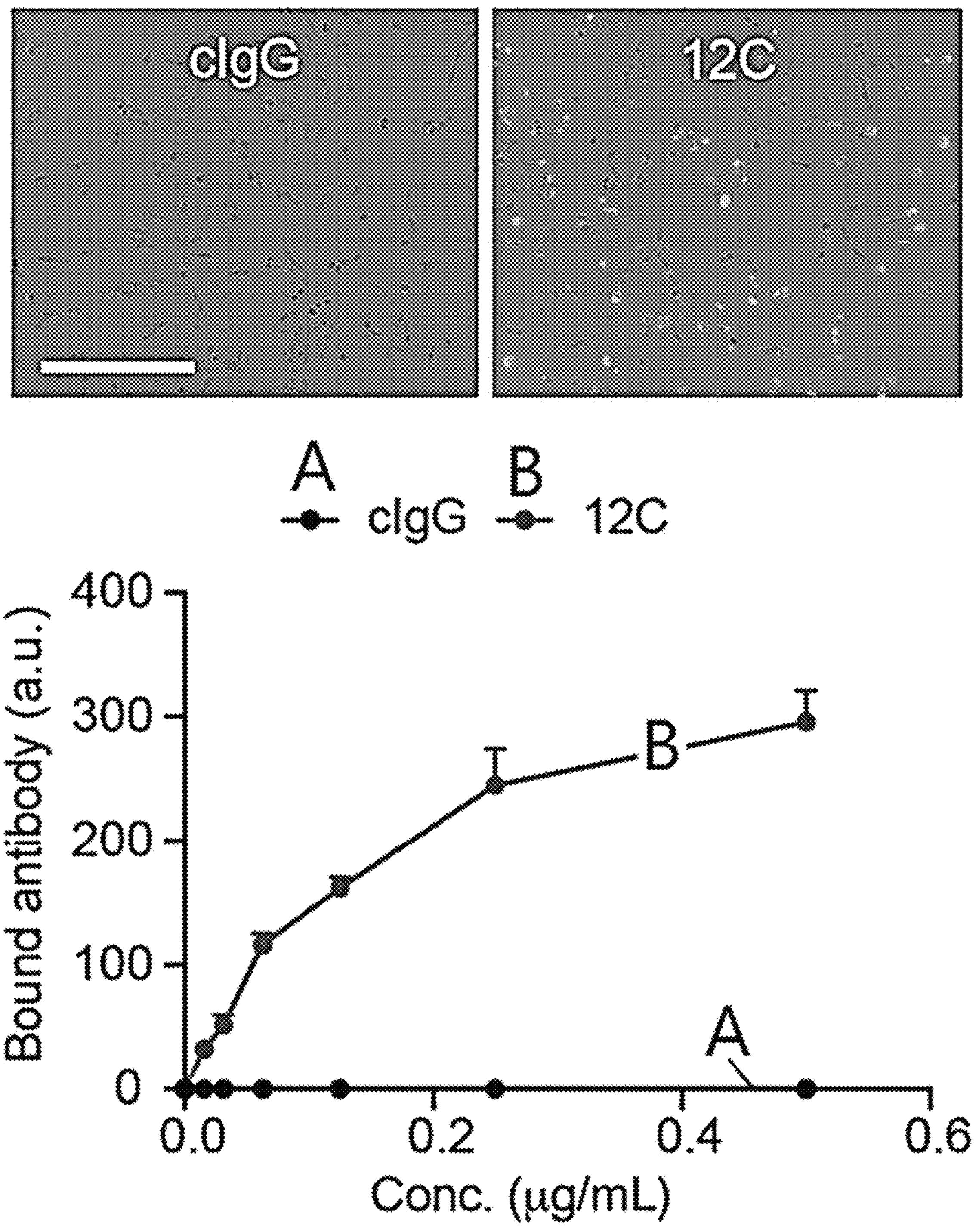
FIG. 5A shows 12C antibody binding on the BT549$^{cPD\text{-}L1}$ cells.

Antibody binding and blockade assays were performed as described in Li et al. (2018), supra. Briefly, to measure PD-L1 protein and PD-L1 antibody interaction, $1\times10^4$ $BT549^{cPD-L1}$ cells were seeded per well in 96-well plates. The plates were then incubated with cIgG control (Rockland Immunochemicals, Pottstown, PA), 12C10E4 antibody, or cPD-L1 A12C10E4 antibody and anti-canine Alexa Fluor 488 dye conjugate (SouthernBiotech, Birmingham, AL). Every hour green fluorescent signal was measured and quantified by IncuCyte S3 (Sartorius, Goettingen, Germany) (FIG. 5A).

Figure 5B:
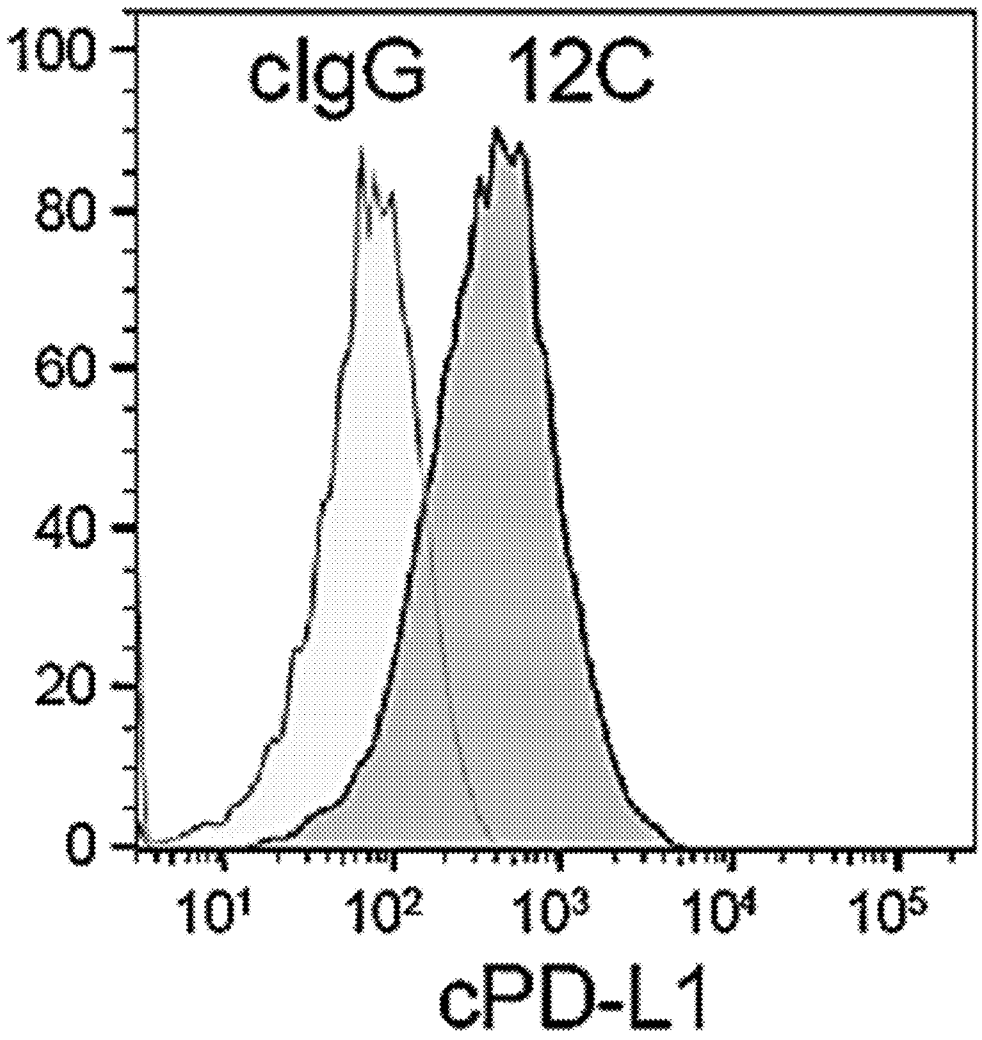
FIG. 5B shows a flow cytometer analysis by 12C chimeric antibody in the BT549$^{cPD\text{-}L1}$ cells, with cIgG serving as a negative control.

To measure PD-1 protein on the cells, $1\times10{+}BT549^{cPD-L1}$ cells were seeded per well in 96-well plates. The plates were then incubated with cIgG control (Rockland Immunochemicals. Pottstown, PA), 12C10E4 antibody or cPD-L1 A12C10E4 antibody, cPD-1-hFc protein (human Fc protein conjugated; Sino Biological US, Wayne, PA), and/or anti-human Alexa Fluor 488 dye conjugate (ThermoFisher Scientific, Waltham, MA). Every 3 hours green fluorescent signal was measured and quantified by IncuCyte S3 (Sartorius, Goettingen, Germany) (FIG. 5B). The image analysis was performed according to the manufacturer's protocol.

Figure 7A:
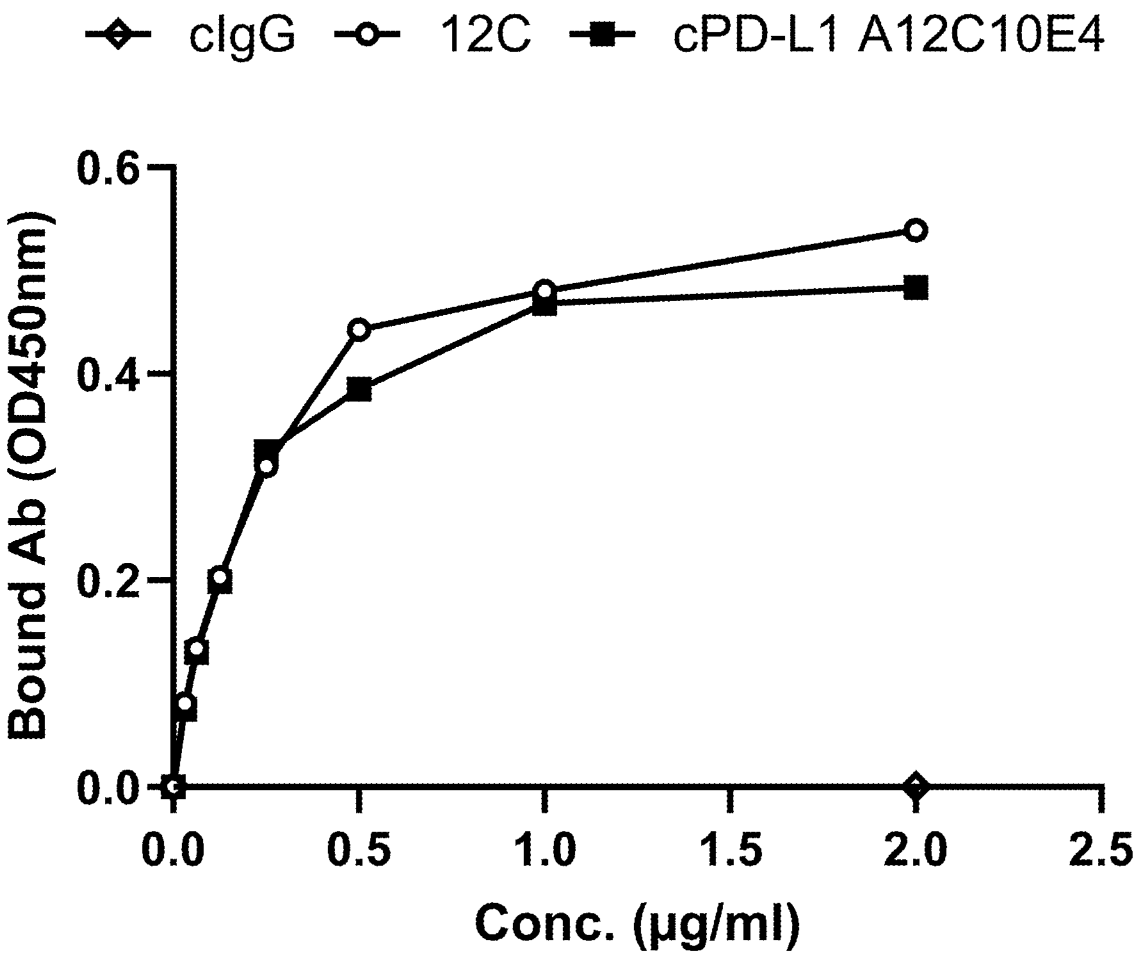
FIG. 7A shows the antibody binding detected in a cell free assay using cPD-L1 12C10E4 (incorporating the light chain SEQ ID NO: 1 and heavy chain SEQ ID NO: 3) and cPD-L1 A12C10E4 (incorporating the light chain SEQ ID NO: 27 and the heavy chain SEQ ID NO: 3).

ELISA based assays were also performed to compare the receptor/ligand and receptor/antibody binding. The 6× His tagged extracellular domain of cPD-L1 proteins were expressed in the ExpiCHO cell system (ThermoFisher Scientific, Waltham, MA) and purified by the Ni-NTA agarose (ThermoFisher Scientific, Waltham, MA) according to the manufacturer's protocol. FIG. 7A illustrates that the antibodies 12C and cPD-L1 A12C10E4 showed equivalent binding activity.

Figure 7B:
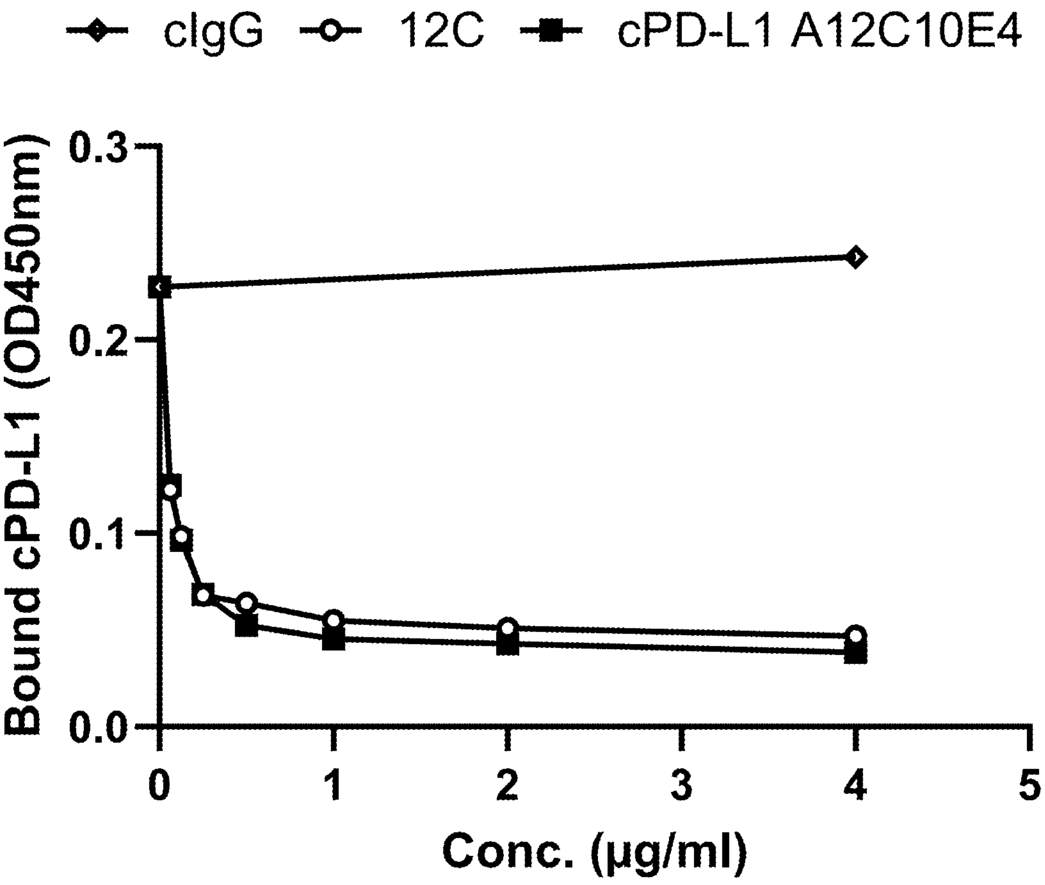
FIG. 7B shows the antibody blockade detected in a cell free assay using cPD-L1 12C10E4 (incorporating the light chain SEQ ID NO: 1 and heavy chain SEQ ID NO: 3) and cPD-L1 A12C10E4 (incorporating the light chain SEQ ID NO: 27 and the heavy chain SEQ ID NO: 3) quantified by measuring green fluorescence at the IncuCyte® S3 Live-Cell Analysis System (Sartorius AG, Gottingen, Germany).

For the cPD-L1/cPD-L1 blockade assays. Pierce Ni-NTA coated 96-well plates (ThermoFisher Scientific, Waltham, MA) were coated with canine PD-L1-His proteins and PD-1-Fc proteins (human Fc-protein conjugated) (SinoBiological US, Wayne, PA), and anti-human IgG Fc specific horseradish peroxidase (HRP)-conjugated secondary antibodies (SouthernBiotech, Birmingham, AL) were added, followed by the addition of anti-canine PD-L1, 12C10E4 or cPD-L1 A12C10E4 antibodies. The bound PD-1-Fc protein was quantified by measuring $OD_{450}$ value with a Synergy LX multi-mode reader. FIG. 7B shows a comparison of the blockade activity of the two chimeric antibodies 12C and cPD-L1 A12C10E4, illustrating that the 12C and cPD-L1 A12C10E4 antibodies showed equivalent blockade activity.

The chimeric antibody 12C10E4 bound to the membrane-localized cPD-L1 protein (FIGS. 5A and 5B), but did not recognize cPD-L2 protein (FIG. 5C).

Example 7

Binding Affinity ($K_D$) Determination of Caninized cPD-L1 Chimeric Antibody The binding affinity ($K_D$) of the chimeric cPD-L1/cPD-L1 antibody (12C10E4) for canine PD-L1 was determined by Octet Biolayer interferometry (BLI) using the Octet RED384 system (Sartorius, Bohemia, NY). Briefly. His-tagged cPD-L1 protein was loaded on the Octet NTA biosensor at a concentration of 200 nM. The association step was performed by submerging the sensors in three concentrations of the chimeric cPD-L1/cPD-L1 antibody (12C10E4) (50, 100, 200 nmol/L) in the kinetic buffer. Dissociation was performed and monitored in fresh kinetic buffer. Data were analyzed with Octet Analysis HT software (Sartorius, Bohemia, NY), and the bound cPD-1 proteins were quantified by measuring green fluorescence at the IncuCyte S3.

Figure 5E:
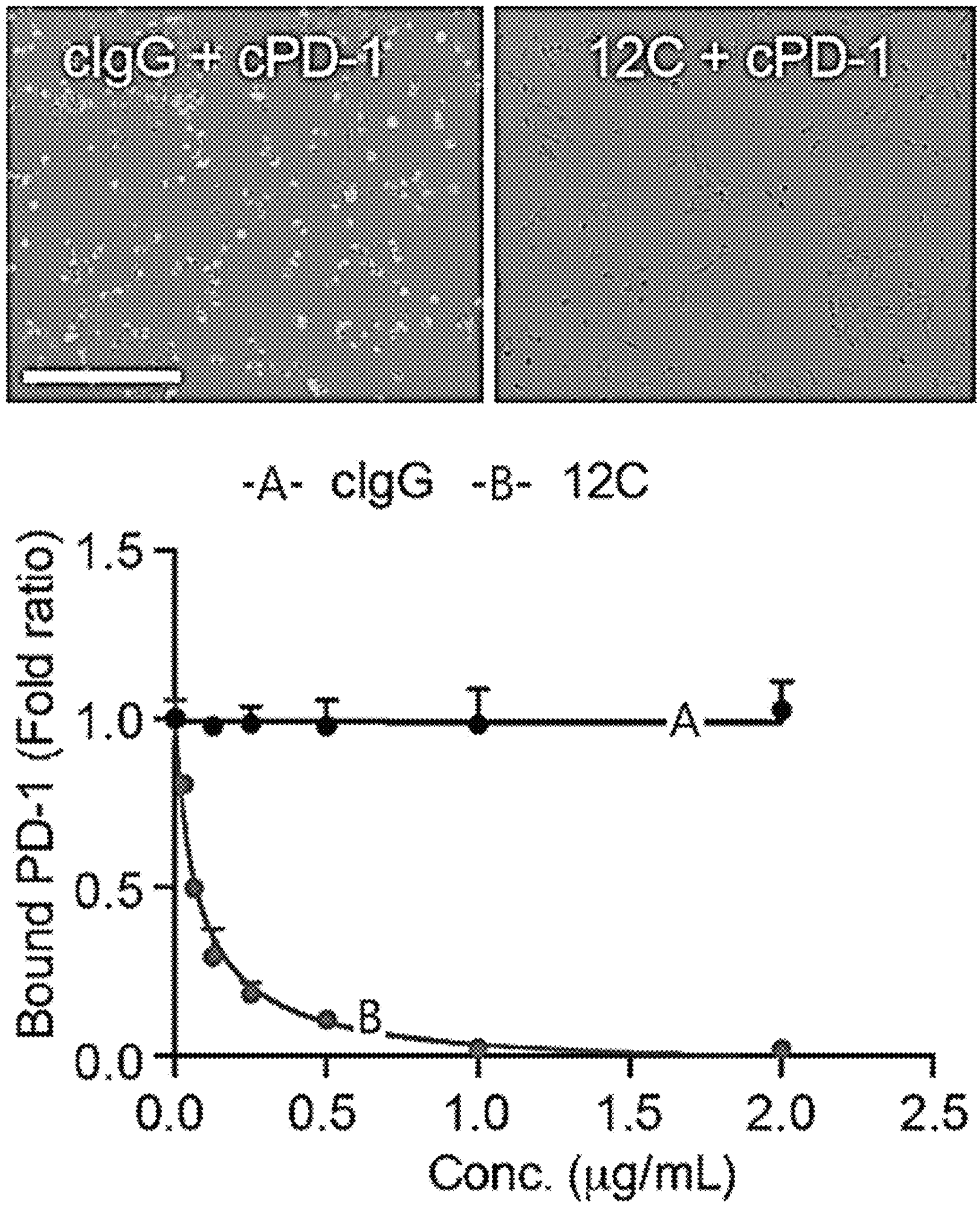
FIG. 5E shows $EC_{50}$ of 12C chimeric antibody, 12C10E4. $EC_{50}$=0.419 μg/ml, with the bound cPD-1 proteins quantified by measuring green fluorescence at the IncuCyte® S3 Live-Cell Analysis System (Sartorius AG, Gottingen, Germany).

The $K_D$ of the chimeric antibody 12C10E4 as determined by Octet was 8.6 nmol/L (FIG. 5D). Similar to the murine 12C antibody obtained from the hybridoma, the 12C chimeric antibody blocked the cPD-L1/cPD-1 interaction ($EC_{50}$=0.419 μg/ml; FIG. 5E).

Example 7B

Binding Affinity ($K_D$) Determination of Caninized cPD-L1 Chimeric Antibody The binding affinity ($K_D$) of the chimeric cPD-L1/cPD-L1 antibody (cPD-L1 A12C10E4) for canine PD-L1 is determined by Octet Biolayer interferometry (BLI) using the Octet RED384 system (Sartorius, Bohemia, NY). Briefly. His-tagged cPD-L1 protein is loaded on the Octet NTA biosensor at a concentration of 200 nM. The association step is performed by submerging the sensors in three concentrations of the chimeric cPD-L1/cPD-L1 antibody (cPD-L1 A12C10E4) (50, 100, 200 nmol/L) in the kinetic buffer. Dissociation is performed and monitored in fresh kinetic buffer. Data is analyzed with Octet Analysis HT software (Sartorius, Bohemia, NY), and the bound cPD-1 proteins are quantified by measuring green fluorescence at the IncuCyte S3.

The $K_D$ of the chimeric antibody cPD-L1 A12C10E4 is determined by Octet. The cPD-L1 A12C10E4 chimeric antibody is expected to block the cPD-L1/cPD-1 interaction.

Example 8

Activation of Peripheral Blood Mononuclear Cells (PBMCs) and Cytokine Measurement Primary canine PBMCs (cPBMC) were isolated from dog blood using SepMate PBMC isolation tubes (Stemcell Technologies, Inc., Vancouver. B.C., Canada) and Histopaque-1077 (Millipore Sigma, Burlington, MA) per the manufacturer's protocol. The activation of canine T ells by anti-canine CD3 and CD28 antibodies has been well established in previous studies.

Briefly, the canine T cells in PBMCs were activated with 10 ng/ml canine interleukin-2 (IL-2) (10 ng/ml) (Novus Biologicals, Centennial, CO), and co-treated with and without 1 μg/ml anti-canine CD38 antibody (CA17.2A12 clone, coated; ThermoFisher Scientific, Waltham, MA) and 3 μg/mL (in medium) anti-canine CD28 antibody (1C6 clone; ThermoFisher Scientific, Waltham, MA) for 48 hours. MILLIPLEX Canine Cytokine/Chemokine Magnetic Bead Panel (Sigma-Aldrich, St Louis, MO) was used to multiplex and measure IFNγ, IL-10, and TNFα in these activated canine PBMCs following manufacturer's protocols.

Samples were incubated with the cytokine magnetic beads on shaker for 2 hours followed by incubation with secondary detection antibody provided in the kit. The plate was read on Attune flow cytometer by using the FL2 channel for the reporter (PE channel) and FL4 (APC) channel for classification. For each of the cytokines, 300 beads were measured, and data were collected as forward and side scatter and on a log scale FL2 vs FL4. Concentrations of cytokines were quantified as ng/ml using Cytokine Multiplex Analysis Software (MPLEX, Cytomic Analytical LLC). The data showed a significant induction in the expression of IFNγ, IL-10 and TNFα with anti-CD3/CD28 and IL2 treatment as compared to IL-2 treatment alone, and this activation protocol was used for the remainder of the studies.

Example 9

Gene Expression Analysis of Caninized cPD-L1 Chimeric Antibody

Canine IO Panel (NanoString Technologies, Inc., Seattle, WA) analyses were used to query changes in gene expression upon activation of PBMCs from three healthy pet dogs in Example 8. Activation of the cPBMCs was performed as described previously in Example 8.

RNAs from resting and activated cPBMCs were isolated (RNeasy kit, Qiagen, Germantown, MD) and submitted to Stark Neurosciences Research Institute Biomarker Core, Indiana University School of Medicine (Indiana University, Indianapolis, IN) for detection of modulation of genes upon activation using nCounter® Canine IO Panel (NanoString Technologies, Inc., Seattle, WA).

The Canine IO panel was used to query the changes in about 700 genes. Groupwise analyses of the data were conducted using Rosalind (Rosalind, San Diego, CA) using control cPBMCs (n=3) and compared with activated cells (n=3). There were 65 genes that were differentially expressed when comparing control PBMCs with activated PBMCs (FC≥1.5; $P<0.05$), including 30 upregulated and 35 downregulated genes.

Data were visualized using heatmap, volcano plot and histogram for specific genes. In the heatmap, each column consists of data from one sample. IFNγ (FIG. 5H) and TNFα (FIG. 5I) concentrations were also analyzed in the activated canine PBMCs.

Figure 5F:
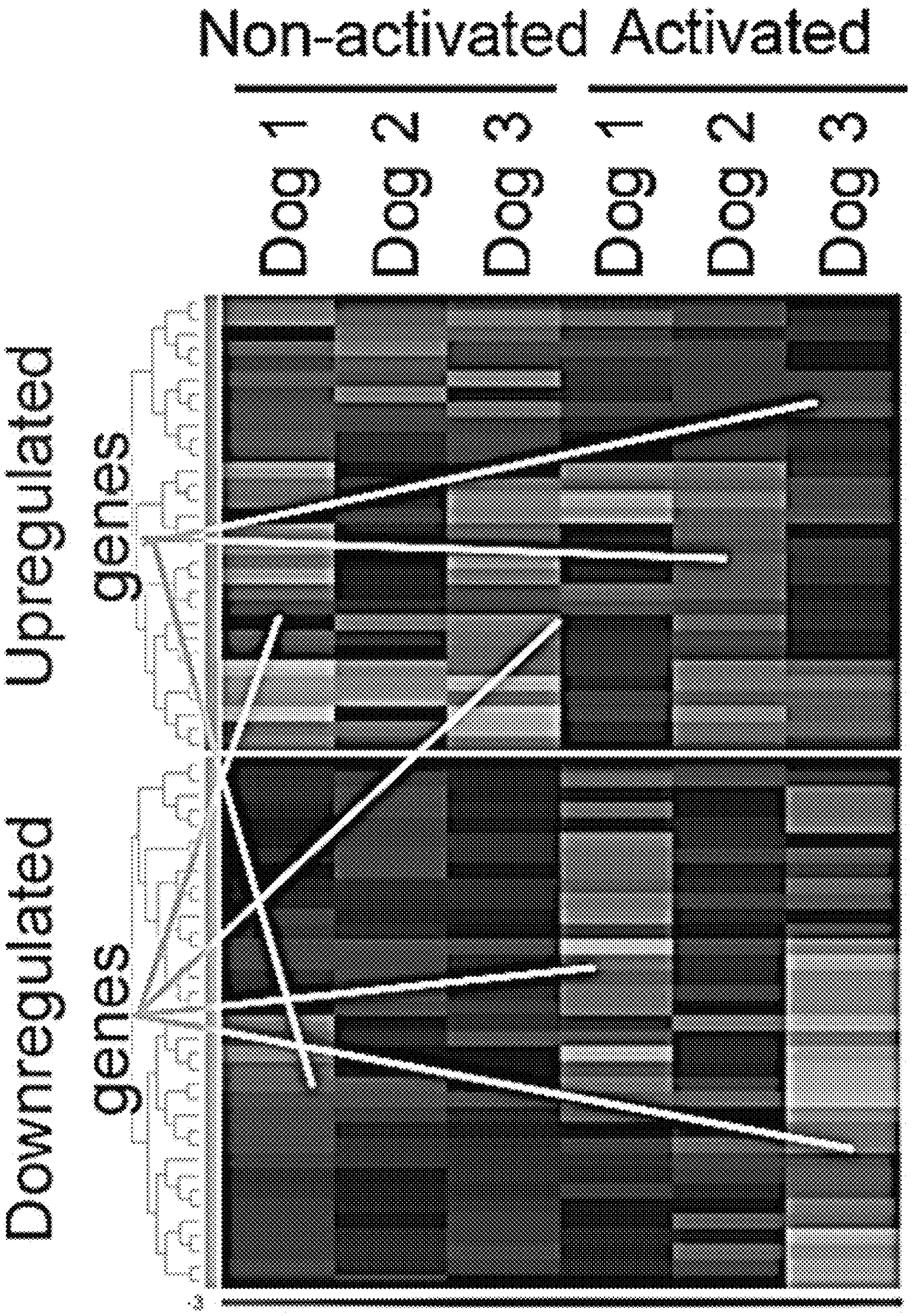
FIGS. 5F and 5G show images related to data from Canine IO Panel (NanoString) analyses, which were used to query changes in gene expression upon activation of canine peripheral blood mononuclear cells (cPBMCs) from three healthy pet dogs. The RNA from the resting and activated PBMCs was used for NanoString work. The Canine IO Panel was used to query the changes in approximately 700 genes. Groupwise analyses were conducted using "Rosalind." There were 65 genes that were differentially expressed when comparing control PBMCs with activated PBMCs ($P<0.05$, $FC>1.5$) including 30 upregulated and 35 down-regulated genes. In the heatmap, each column consists of data from one sample.
Figure 5G:
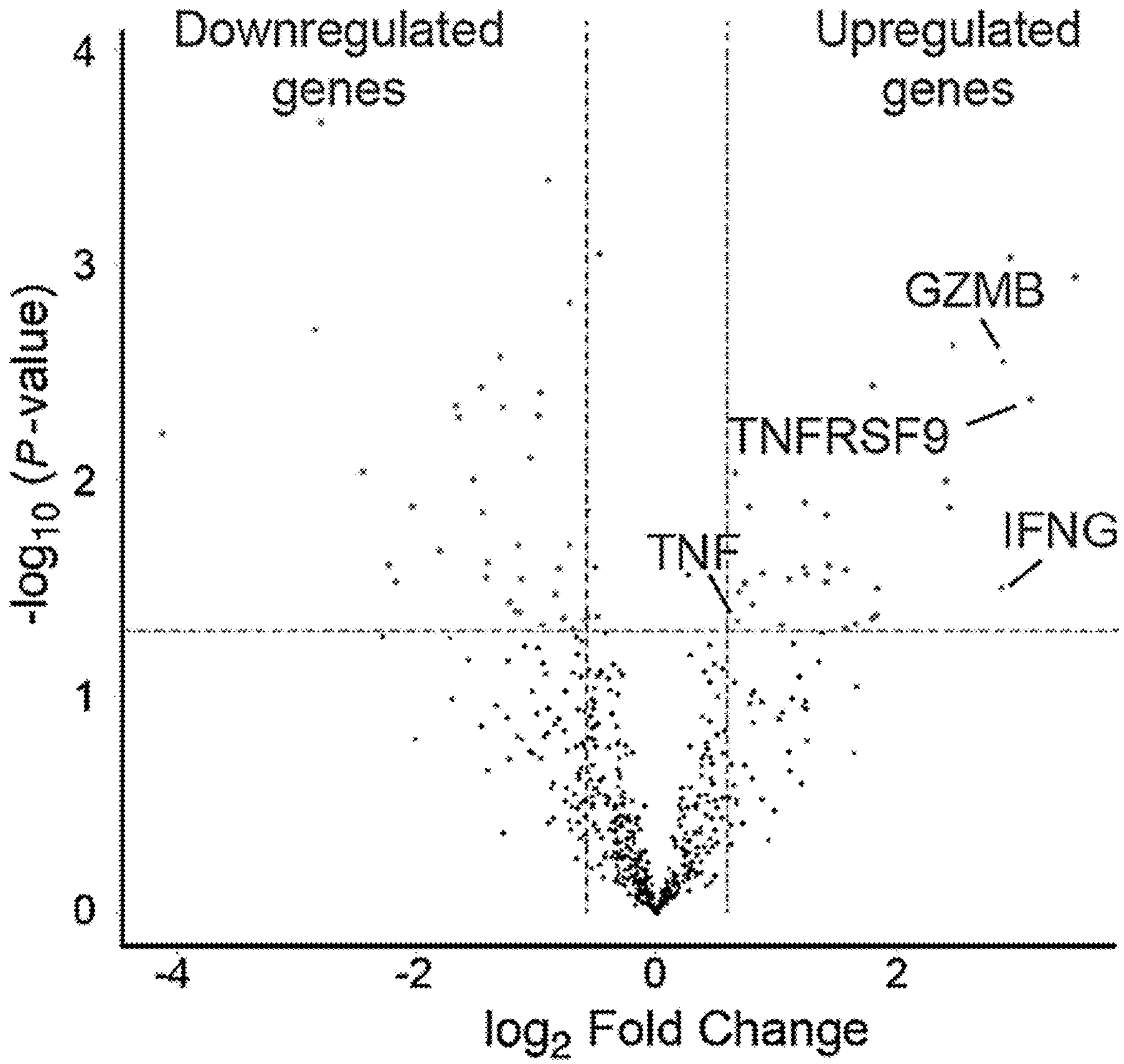
Figure 5H:
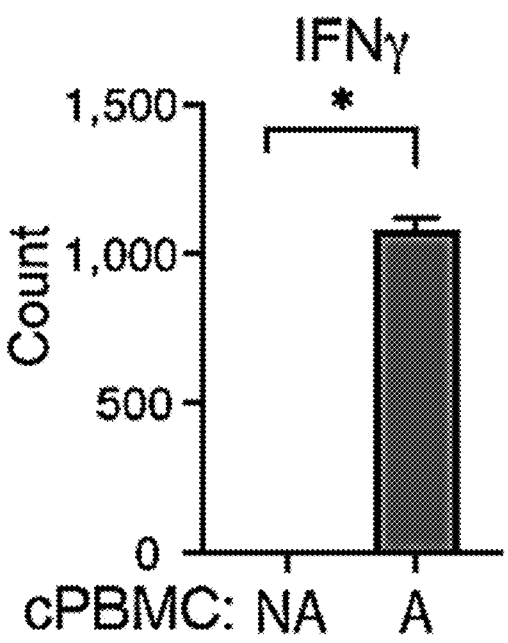
FIGS. 5H and 5I show data related to interferon gamma (IFNγ) and tumor necrosis factor alpha (TNFα) concentrations, respectively, in activated cPBMCs.
Figure 5I:
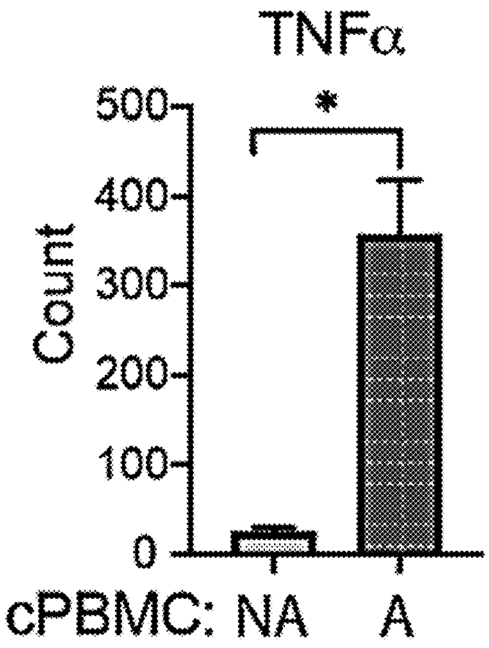

The canine immune-oncology panel analysis (FIGS. 5F and 5G; Table 1) and analysis of secreted cytokines (IFNγ and TNFα; FIGS. 5H and 5I) demonstrated the activation of canine PBMCs by anti-canine CD3 and CD28 antibodies and canine IL2 treatment.

TABLE 1

Genes altered in the activated cPBMCs from the nCounter canine immune-oncology panel analysis.

| Name | Description | Fold Change | Log2 Fold Change | p-Value | p-Adj | Ave. Log2 Exp. |
|---|---|---|---|---|---|---|
| S100A4 | S100 calcium binding protein A4 | 2.70 | 1.43 | 0.02 | 0.34 | 11.23 |
| IFNG | interferon gamma | 7.32 | 2.87 | 0.03 | 0.35 | 8.35 |
| IL2RA | interleukin 2 receptor, alpha | 1.84 | 0.88 | 0.03 | 0.34 | 9.80 |
| TNF | tumor necrosis factor | 1.60 | 0.67 | 0.04 | 0.39 | 8.56 |
| CSF2 | colony stimulating factor 2 | 2.98 | 1.57 | 0.03 | 0.34 | 7.21 |
| IL12A | interleukin 12A | 1.61 | 0.68 | 0.03 | 0.35 | 6.15 |
| BIRC5 | baculoviral IAP repeat containing 5 | 2.97 | 1.57 | 0.05 | 0.40 | 6.32 |
| BRCA2 | breast cancer 2, early onset | 5.41 | 2.44 | 0.01 | 0.26 | 5.35 |
| CDKN2C | cyclin-dependent kinase inhibitor 2C | 2.36 | 1.24 | 0.01 | 0.26 | 6.92 |
| PCNA | proliferating cell nuclear antigen | 1.71 | 0.77 | 0.01 | 0.26 | 9.32 |
| C1QA | complement component 1, q subcomponent, A chain | 3.15 | 1.66 | 0.05 | 0.39 | 5.66 |
| CXCL10 | chemokine (C-X-C motif) ligand 10 | 2.66 | 1.41 | 0.03 | 0.34 | 14.16 |
| ILF3 | interleukin enhancer binding factor 3, 90 kDa | 1.67 | 0.74 | 0.03 | 0.34 | 7.37 |
| C1S | complement component 1, s subcomponent | 3.57 | 1.84 | 0.03 | 0.35 | 6.11 |
| LAG3 | lymphocyte-activation gene 3 | 3.56 | 1.83 | 0.04 | 0.39 | 6.69 |
| GZMA | granzyme A | 11.23 | 3.49 | 0.00 | 0.13 | 8.74 |
| BST1 | bone marrow stromal cell antigen 1 | 2.05 | 1.04 | 0.05 | 0.39 | 5.44 |
| PRF1 | perforin 1 | 2.34 | 1.23 | 0.03 | 0.34 | 7.25 |
| CD3G | CD3g molecule, gamma | 1.58 | 0.66 | 0.01 | 0.23 | 9.76 |
| LOC490356 | cytokine SCM-1 beta-like | 7.70 | 2.95 | 0.00 | 0.13 | 8.75 |
| LOC490629 | transmembrane protease serine 9-like | 2.38 | 1.25 | 0.03 | 0.34 | 6.47 |
| GZMB | granzyme B | 7.38 | 2.88 | 0.00 | 0.16 | 8.84 |
| TBX21 | T-box 21 | 2.66 | 1.41 | 0.01 | 0.26 | 8.23 |
| LTA | lymphotoxin alpha | 2.15 | 1.11 | 0.03 | 0.34 | 6.70 |
| TYMS | thymidylate synthetase | 1.74 | 0.80 | 0.04 | 0.38 | 7.87 |
| KLRB1 | killer cell lectin-like receptor subfamily B, member 1 | 3.49 | 1.80 | 0.00 | 0.16 | 7.55 |
| MKI67 | antigen identified by monoclonal antibody Ki-67 | 5.30 | 2.40 | 0.01 | 0.23 | 6.40 |
| CDK1 | cyclin-dependent kinase 1 | 3.49 | 1.80 | 0.04 | 0.39 | 6.07 |
| NKG7 | natural killer cell group 7 sequence | 5.53 | 2.47 | 0.00 | 0.16 | 7.34 |
| IL13RA1 | interleukin 13 receptor, alpha 1 | −1.67 | −0.74 | 0.00 | 0.15 | 8.16 |
| TNFRSF1A | tumor necrosis factor receptor superfamily, member 1A | −1.53 | −0.61 | 0.04 | 0.39 | 8.72 |
| IL1RN | interleukin 1 receptor antagonist | −1.95 | −0.96 | 0.05 | 0.39 | 9.86 |
| PDPN | podoplanin | −4.54 | −2.18 | 0.03 | 0.34 | 6.74 |
| ADORA2A | adenosine A2a receptor | −1.96 | −0.97 | 0.00 | 0.16 | 8.40 |
| IL1B | interleukin 1, beta | −3.51 | −1.81 | 0.02 | 0.34 | 7.40 |
| CD36 | CD36 molecule | −3.15 | −1.66 | 0.01 | 0.16 | 5.36 |
| PLAUR | plasminogen activator, urokinase receptor | −2.49 | −1.31 | 0.00 | 0.16 | 8.56 |
| LRP1 | low density lipoprotein receptor-related protein 1 | −2.44 | −1.29 | 0.00 | 0.16 | 7.54 |
| CSF2RB | colony stimulating factor 2 receptor, beta | −2.35 | −1.23 | 0.04 | 0.38 | 7.54 |
| NCF4 | neutrophil cytosolic factor 4 | −2.19 | −1.13 | 0.03 | 0.34 | 6.64 |
| TLR3 | toll-like receptor 3 | −4.11 | −2.04 | 0.01 | 0.26 | 4.99 |
| SIGLEC1 | sialic acid binding Ig-like lectin 1 | −2.66 | −1.41 | 0.02 | 0.34 | 6.73 |
| HCK | hemopoietic cell kinase | −2.74 | −1.46 | 0.01 | 0.26 | 7.30 |
| SDC4 | syndecan 4 | −2.23 | −1.16 | 0.02 | 0.34 | 10.96 |
| CMKLR1 | chemokine-like receptor 1 | −2.68 | −1.42 | 0.03 | 0.34 | 6.51 |
| ITGA5 | integrin, alpha 5 | −1.66 | −0.73 | 0.02 | 0.34 | 8.59 |
| LTBR | lymphotoxin beta receptor | −2.09 | −1.06 | 0.01 | 0.22 | 6.08 |

TABLE 1-continued

Genes altered in the activated cPBMCs from the nCounter canine immune-oncology panel analysis.

| Name | Description | Fold Change | Log2 Fold Change | p-Value | p-Adj | Ave. Log2 Exp. |
|---|---|---|---|---|---|---|
| THBS1 | thrombospondin 1 | −5.47 | −2.45 | 0.01 | 0.23 | 5.52 |
| IL1RAP | interleukin 1 receptor accessory protein | −2.21 | −1.14 | 0.04 | 0.39 | 7.27 |
| CSF1R | colony stimulating factor 1 receptor | −3.20 | −1.68 | 0.00 | 0.16 | 6.90 |
| ITGAM | integrin, alpha M | −6.96 | −2.80 | 0.00 | 0.12 | 7.36 |
| CXCR3 | chemokine (C-X-C motif) receptor 3 | −1.77 | −0.82 | 0.03 | 0.34 | 8.00 |
| TNFRSF9 | tumor necrosis factor receptor superfamily, member 9 | 8.65 | 3.11 | 0.00 | 0.16 | 6.75 |
| CD55 | CD55 molecule, decay accelerating factor for complement | −1.80 | −0.85 | 0.03 | 0.36 | 7.27 |
| SERPINB2 | serpin peptidase inhibitor, clade B (ovalbumin), member 2 | −17.43 | −4.12 | 0.01 | 0.19 | 6.33 |
| AMICA1 | adhesion molecule, interacts with CXADR antigen 1 | −1.63 | −0.70 | 0.05 | 0.40 | 8.63 |
| FADD | Fas (TNFRSF6)-associated via death domain | −1.51 | −0.60 | 0.01 | 0.22 | 8.23 |
| CD9 | CD9 molecule | −2.76 | −1.47 | 0.00 | 0.16 | 9.46 |
| FCRL2 | Fc receptor-like 2 | −2.89 | −1.53 | 0.01 | 0.23 | 7.50 |
| IL6R | interleukin 6 receptor | −1.98 | −0.99 | 0.01 | 0.16 | 6.12 |
| CEACAM1 | carcinoembryonic antigen-related cell adhesion molecule 1 | −1.72 | −0.79 | 0.04 | 0.39 | 7.89 |
| PYCARD | PYD and CARD domain containing | −2.27 | −1.18 | 0.04 | 0.39 | 6.36 |
| LOC102 153988 | uncharacterized LOC102153988 | −4.71 | −2.24 | 0.02 | 0.34 | 8.47 |
| LOC102 154078 | uncharacterized LOC102154078 | −7.20 | −2.85 | 0.00 | 0.16 | 7.13 |
| VSIR | | −1.89 | −0.92 | 0.00 | 0.12 | 9.24 |

Example 10

Figure 5J:
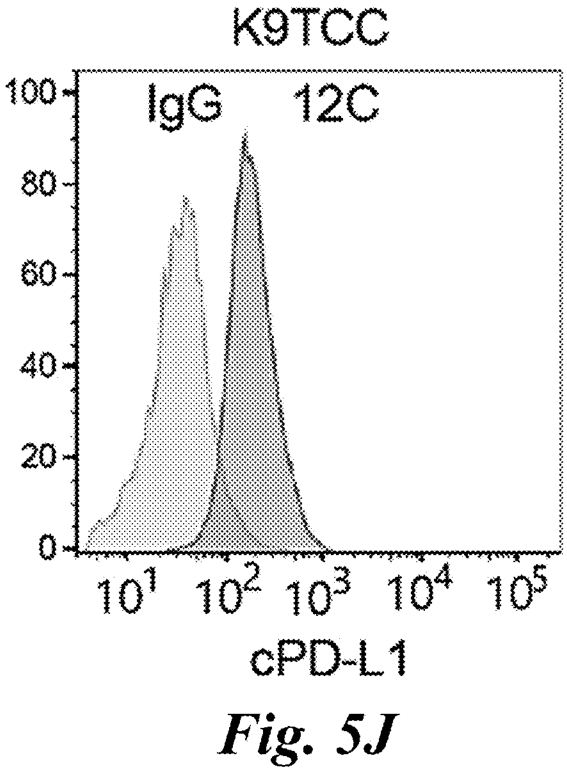
FIGS. 5J and 5K are flow cytometric analysis data of cPD-L1 protein expression on the K9TCC or the nuclear-restricted RFP-expressing K9TCC (K9TCC$^{nRFP}$) cells using the 123C chimeric Ab. The endogenous PD-L1 expression was stimulated by 50 ng/ml canine IFNγ for 12 hours, cIgG served as a negative control.
Figure 5K:
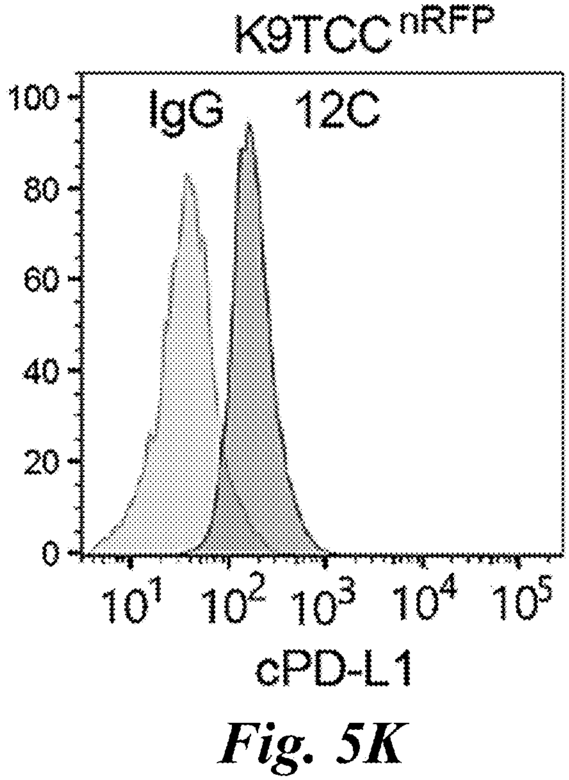
Figure 5L:
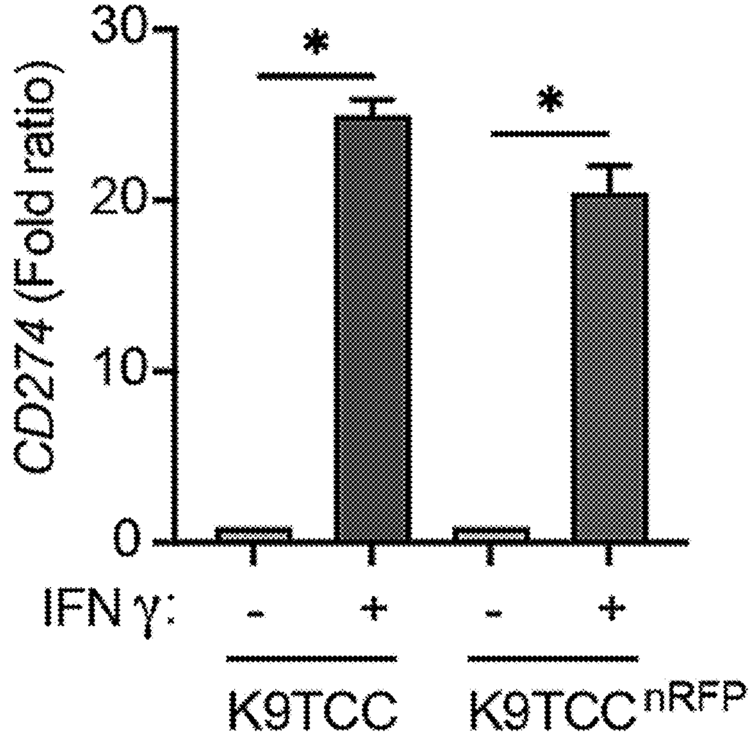
FIG. 5L shows data from a quantitative reverse transcription-polymerase chain reaction (RT-PCR) of cPD-L1 ((D) 274) mRNA expression in the K9TCC or K9TCC$^{nRFP}$ cells.

Caninized cPD-L1 Chimeric Antibody Enhances T Cell-Mediated Tumor Cell Killing To demonstrate immune checkpoint inhibition of the 12C chimeric antibody and analyze the killing of tumor cells by T-cell inactivation, a tumor cell killing assay was performed pursuant to known protocols (see Li et al. (2016), supra) on an ex vivo canine system in which cPD-L1-positive canine bladder cells (K9TCC) were co-cultured with activated canine PBMCs. To quantify the number of surviving or dead tumor cells in a tumor cell killing assay, a K9TCC$^{nRFP}$ cells expressing nuclear-restricted red fluorescent protein (RFP) were established. Expression of endogenous cPD-L1 protein and mRNA in both K9TCC parental and K9TCC$^{nRFP}$ cells upon IFNγ treatment was confirmed (FIGS. 5J-5L). These activated canine PBMCs and K9TCC$^{nRFP}$ cells were then used to perform a tumor cell killing assay.

Briefly, the K9TCC$^{nRFP}$ cells were co-cultured with activated cPBMCs in DMEM/F12 with 10% FBS, cPBMCs were activated via incubation with 100 ng anti-canine CD38 antibody (see Example 8) (CA17.2A12 clone, ThermoFisher Scientific, Waltham, MA)) and 10 ng/ml canine interleukin-2 (IL-2) (Novus Biologicals, Littleton, CO) in DMEM/F12 with 10% FBS. The primary cPBMCs were isolated from dog blood using SepMate PBMC isolation tubes (Stemcell Technologies, Cambridge, MA) and Histopaque-1077 (Sigma-Aldrich, St. Louis, MO) per the manufacturer's protocol.

The live tumor cell count at 72 hours is shown in the bar graph of FIG. 5J. After 96 hours, RFP signals were measured as survived tumor cells, and the expression of IFNγ, IL10, and TNFα in the supernatant of the co-cultured cells was measured by MILLIPLEX Canine Cytokine/Chemokine Magnetic Bead Panel according to manufacturer's protocols.

Figure 5M:
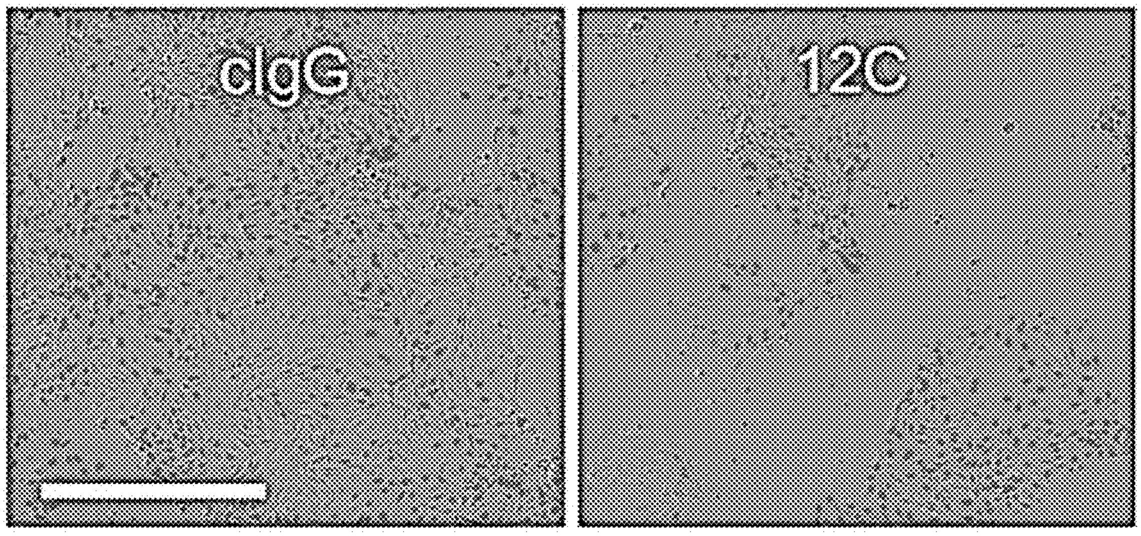
FIG. 5M is images and graphical data related to K9TCC cells that were co-cultured with cPBMCs that were activated with CD3 antibody (100 ng/ml) and interleukin-2 (IL-2) (10 ng/ml) at a ratio of 1 tumor cell:15 cPBMCs, with the live tumor cell count at 72 hours shown in the bar graph (right). The 12C chimeric antibody enhanced the tumor cell killing.
Figure 5M:
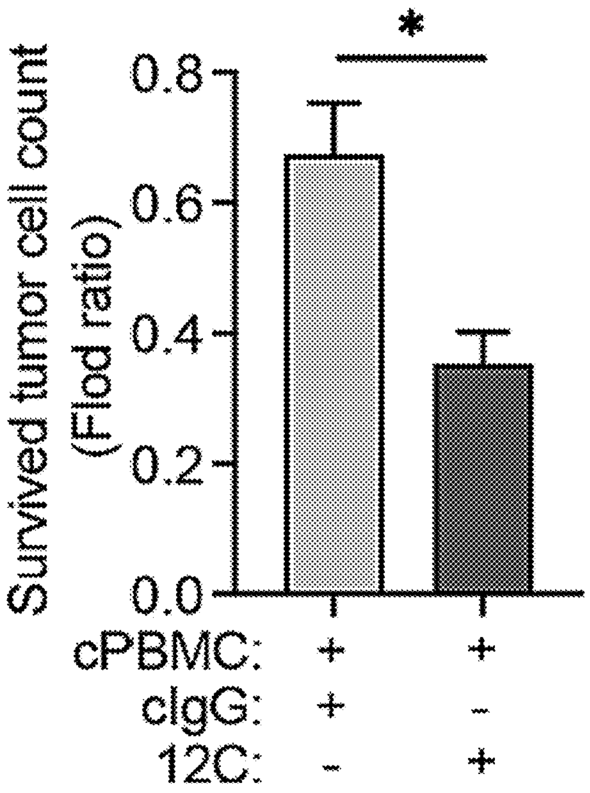
Figure 5N:
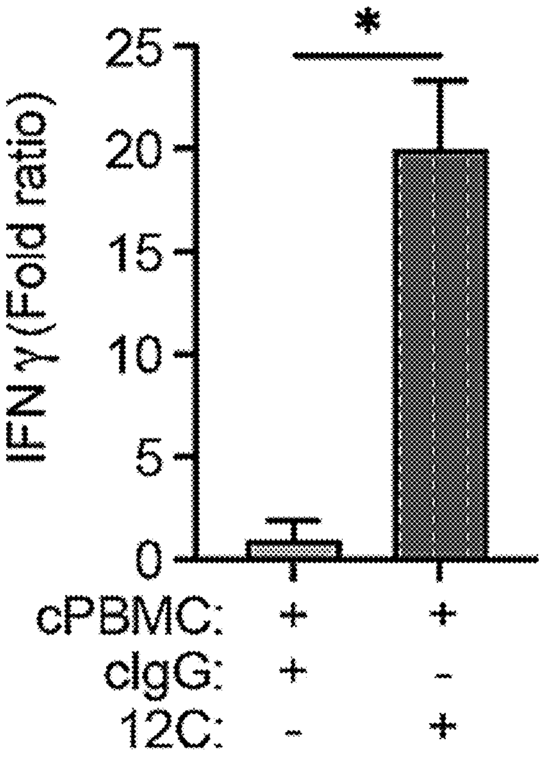
FIG. 5N shows data related to the analysis of IFNγ concentrations in K9TCC cells and activated cPBMCs co-cultured medium with and without the 12C chimeric antibody treatment.

Although the PBMC and tumor cells were from different dogs, and thus the dog lymphocyte antigen (DLA) was not matched between the cPBMCs and K9TCC cells, the 12C chimeric antibody enhanced tumor cell killing activity and IFNγ secretion (FIGS. 5M and 5N).

Example 10B

Caninized cPD-L1 Chimeric Antibody Enhances T Cell-Mediated Tumor Cell Killing To demonstrate immune checkpoint inhibition of the cPD-L1 A12C10E4 chimeric antibody and analyze the killing of tumor cells by T-cell inactivation, a tumor cell killing assay is performed pursuant to known protocols (see Li et al. (2016), supra) on an ex vivo canine system in which cPD-L1-positive canine bladder cells (K9TCC) are co-cultured with activated canine PBMCs. To quantify the number of surviving or dead tumor cells in a tumor cell killing assay. KOTCC$^{nRFP}$ cells expressing nuclear-restricted red fluorescent protein (RFP) are established. Expression of endogenous cPD-L1 protein and mRNA in both K9TCC parental and K9TCC$^{nRFP}$ cells upon IFNγ treatment are confirmed. These activated canine PBMCs and K9TCC$^{nRFP}$ cells are then used to perform a tumor cell killing assay.

Briefly, the K9TCC$^{nRFP}$ cells are co-cultured with activated cPBMCs in DMEM/F12 with 10% FBS, cPBMCs are activated via incubation with 100 ng anti-canine CD38 antibody (see Example 8) (CA17.2A12 clone. ThermoFisher Scientific, Waltham, MA)) and 10 ng/ml canine interleukin-2 (IL-2) (Novus Biologicals, Littleton, CO) in DMEM/F12 with 10% FBS. The primary cPBMCs are isolated from dog blood using SepMate PBMC isolation tubes (Stemcell Technologies, Cambridge, MA) and Histopaque-1077 (Sigma-Aldrich, St. Louis, MO) per the manufacturer's protocol.

The live tumor cell count at 72 hours is determined. After 96 hours, RFP signals are measured to determine survived tumor cells, and the expression of IFNγ, IL10, and TNFα in the supernatant of the co-cultured cells is measured by MILLIPLEX Canine Cytokine/Chemokine Magnetic Bead Panel according to manufacturer's protocols.

Although the PBMC and tumor cells are from different dogs, and thus the dog lymphocyte antigen (DLA) is not matched between the cPBMCs and K9TCC cells, the cPD-L1 A12C10E4 chimeric antibody is expected to show enhanced tumor cell killing activity and IFNγ secretion.

Example 11

Treatment of Laboratory Dogs with 12C10E4 Chimeric Antibody

A single-dose pilot study to assess initial safety and pharmacokinetic parameters was performed in six laboratory beagles approximately 12-15 months old, with male and female dogs included. The dogs were housed and evaluated in the Pre-Clinical Research Laboratory. College of Veterinary Medicine, Purdue University. West Lafayette, IN. The 12C10E4$^{cPD\text{-}L1}$ chimeric antibody for the laboratory dog study was produced in the Molecular Evolution. Protein Engineering, and Production Facility at Purdue University (West Lafayette, IN) as described above. The antibody solution was *Mycoplasma* free and contained less than 0.5 EU endotoxin/mg antibody (consistent with the endotoxin limit for human PD-L1 antibody solutions).

After being acclimated to the facility, the dogs were treated with the 12C10E4$^{cPD\text{-}L1}$ chimera antibody diluted in sterile water for intravenous (IV) administration (6 ml/kg body weight total volume) and administered through an IV catheter over 1 hour. Six dogs were treated and received 2 mg/kg or 5 mg/kg antibody.

Figure 6A:
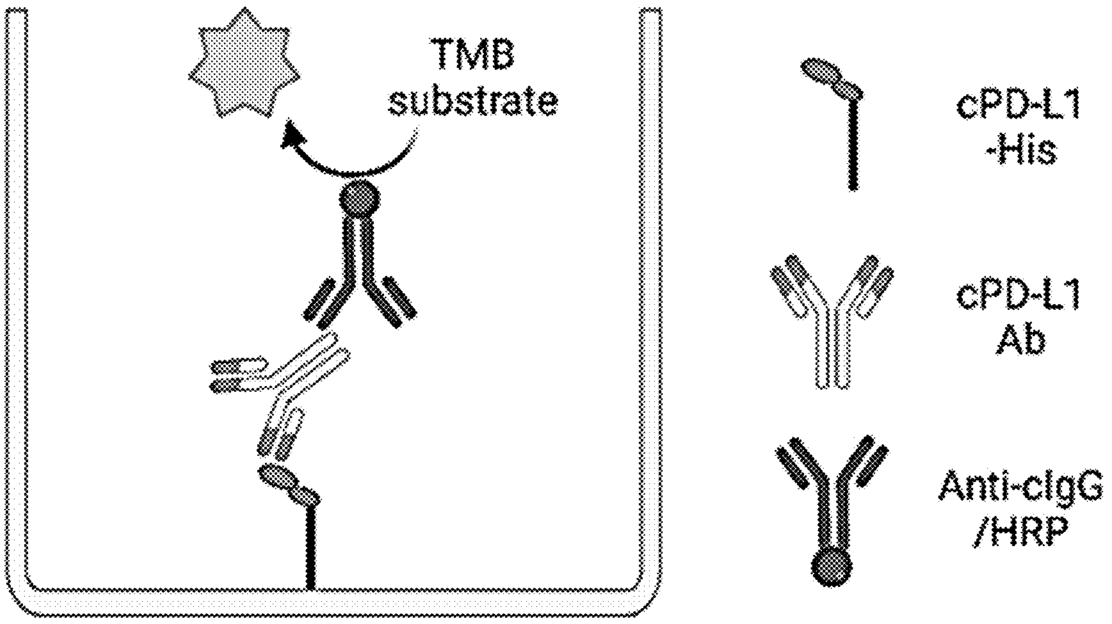
FIG. 6A shows a schematic diagram of enzyme-linked immunosorbent assay (ELISA) for pharmacokinetics analysis.

Blood was collected for pharmacokinetic analyses at 1, 6, 24, 48, and 72 hours after the start of antibody administration, and then once weekly for 4 weeks. Monitoring for adverse events included physical exam before and during treatment, then twice daily for 7 days, and then weekly for 4 weeks; daily observation for 4 weeks; and complete blood count (CBC), serum biochemistry panel (including, without limitation, measurement of the concentration of the 12C10E4 chimeric antibody in the 12C10E4 antibody-treated dogs' serum (FIG. 6A)), and urinalysis before treatment and weekly for 4 weeks. Additional tests were planned specific to any adverse events observed. Adverse events were categorized using Veterinary Cooperative Oncology Group (VCOG) criteria. See VCOG, Common terminology criteria for adverse events (VCOG-CTCAE) following chemotherapy or biological antineoplastic therapy in dogs and cats v1.1, *Vet Comp Oncol* 14:417-446 (2016).

Figure 6B:
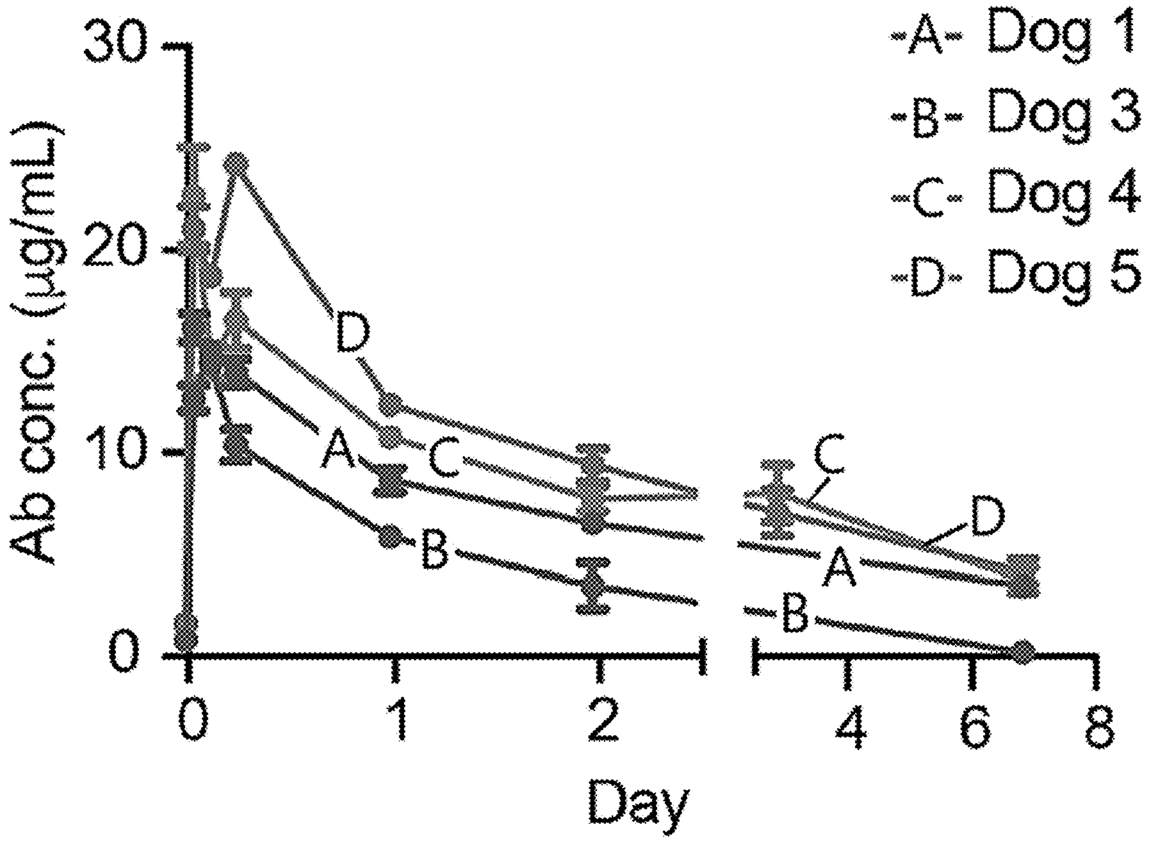
FIG. 6B is a graph of the concentration of the 12C chimeric antibody measured in the 2 mg/kg 12C antibody-treated dogs' serum.
Figure 6C:
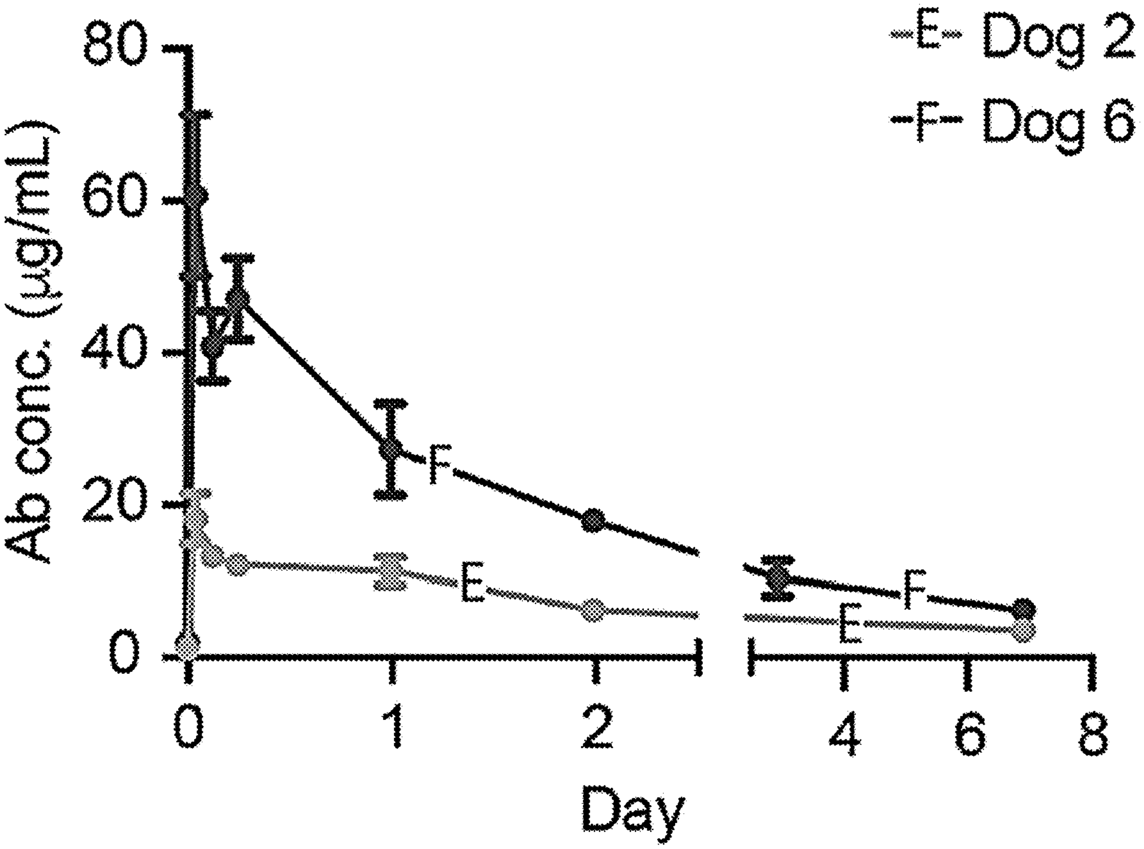
FIG. 6C is a graph of the concentration of the 12C chimeric antibody measured in the 5 mg/kg 12C antibody-treated dogs' serum.

The 12C10E4 chimeric antibody was well tolerated and had a half-life of about 3 days (FIGS. 6B and 6C; Table 2). The half-life of the cPD-L1 antibody was shorter than that for human checkpoint inhibitors and indicated that weekly dosing could be appropriate for dogs. The possible infusion reaction in one dog resolved without intervention. There was good antibody tolerability of the antibody in this single-dose study in the lab dogs and body weight was maintained (Table 2). Nonspecific changes such as a slight reduction in monocyte count reduction and a slight increase in $CO_2$ and gamma-glutamyl transferase (GGT) were transient and resolved without intervention (Table 2).

TABLE 2

Summary of potential adverse events with the initial cPD-L1 antibody administration to laboratory dogs.

| Parameter | Result |
|---|---|
| Dogs | 3 intact female, 3 intact male beagles, 12-15 months of age |
| Antibody dosing | Administered 2 mg/kg (4 dogs) or 5 mg/kg (2 dogs) antibody given by slow intravenous infusion over 1 hour |
| Abnormalities in complete blood counts or serum biochemical profiles | Slightly low monocyte count (0.09 × $10^3$/μL, reference range 0.15-1.35 × $10^3$/μL) at 1 week post treatment; normalized by 2 weeks post treatment (1 dog, 2 mg/kg cPD-L1 antibody). |
| | Slightly high $CO_2$ (25 mmol/L, reference range 13-24 mmol/L) at 1 week post treatment normalized by 2 weeks post treatment in 1 dog and by 4 weeks after antibody treatment in a second dog (1 dog, 2 mg/kg cPDL-1 antibody and the second dog 5 mg/kg cPDL-1 antibody). |
| | Slightly high GGT (18 IU/L, reference range 5-16 IU/L) at 1 week post treatment; normalized by 2 weeks post treatment (1 dog, 5 mg/kg cPD-L1 antibody). |
| | Slightly high cholesterol (306 mg/dL, reference range 124-301 mg/dL) at 1 week after treatment; normalized by 6 weeks after treatment (1 dog, 5 mg/kg cPD-L1 antibody). |

TABLE 2-continued

Summary of potential adverse events with the initial cPD-L1 antibody administration to laboratory dogs.

| Parameter | Result |
|---|---|
| Other observations | Possible infusion reaction in 1 dog who experienced weakness, pale mucous membranes, and bradycardia (reduced heart rate) that started 5 minutes after the completion of the antibody infusion. The dog returned to normal within 10 minutes with no intervention (1 dog, 5 mg/kg cPD-L1 antibody).<br>Mildly decreased appetite the day of treatment in 3 dogs (2 dogs, 2 mg/kg cPD-L1 antibody; 1 dog 5 mg/kg cPD-L1 antibody).<br>Other than these findings, the dogs remained bright, alert, and active, maintained body weight, and had normal temperature/pulse/respiration. |

Example 11B

Treatment of Laboratory Dogs with cPD-L1 A12C10E4 Chimeric Antibody

A single-dose pilot study to assess initial safety and pharmacokinetic parameters is performed in six laboratory beagles approximately 12-15 months old, with male and female dogs included. The dogs are housed and evaluated in the Pre-Clinical Research Laboratory. College of Veterinary Medicine. Purdue University. West Lafayette, IN. The A12C10E4 cPD-L1 chimeric antibody for the laboratory dog study was produced in the Molecular Evolution. Protein Engineering, and Production Facility at Purdue University (West Lafayette, IN) as described above. The antibody solution is *Mycoplasma* free and contains less than 0.5 EU endotoxin/mg antibody (consistent with the endotoxin limit for human PD-L1 antibody solutions).

After being acclimated to the facility, the dogs are first optionally treated with diphenhydramine 2 mg/kg, and after approximately 30 min are then treated with the cPD-L1 A12C10E4 chimera antibody diluted in sterile water for intravenous (IV) administration (6 ml/kg body weight total volume) and administered through an IV catheter over 1 hour. Six dogs are treated and receive 2 mg/kg or 5 mg/kg antibody.

Blood is collected for pharmacokinetic analyses at 1, 6, 24, 48, and 72 hours after the start of antibody administration, and then once weekly for 4 weeks. Monitoring for adverse events includes physical exam before and during treatment, then twice daily for 7 days, and then weekly for 4 weeks: daily observation for 4 weeks; and complete blood count (CBC), serum biochemistry panel (including, without limitation, measurement of the concentration of the cPD-L1 A12C10E4 chimeric antibody in the cPD-L1 A12C10E4 antibody-treated dogs serum), and urinalysis before treatment and weekly for 4 weeks. Additional tests are planned specific to any adverse events observed. Adverse events are categorized using Veterinary Cooperative Oncology Group (VCOG) criteria. See VCOG. Common terminology criteria for adverse events (VCOG-CTCAE) following chemotherapy or biological antineoplastic therapy in dogs and cats v1.1, *Vet Comp Oncol* 14:417-446 (2016).

The cPD-L1 A12C10E4 chimeric antibody is expected to be well tolerated and have a half-life of about 3 days. The half-life of the cPD-L1 antibody is expected to be shorter than that for human checkpoint inhibitors and indicate that weekly dosing could be appropriate for dogs. Antibody tolerability of the antibody in the single-dose study in the lab dogs and body weight is expected to be good.

General and Certain Definitions

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

In the following description, numerous specific details are set forth to provide a thorough understanding of the present disclosure. Particular examples may be implemented without some or all of these specific details and it is to be understood that this disclosure is not limited to particular biological systems, particular cancers, or particular organs or tissues, which can, of course, vary, but remain applicable in view of the data provided herein.

Various techniques and mechanisms of the present disclosure will sometimes describe a connection or link between two components. Words such as attached, linked, coupled, connected, and similar terms with their inflectional morphemes are used interchangeably, unless the difference is noted or made otherwise clear from the context. These words and expressions do not necessarily signify direct connections but include connections through mediate components. It should be noted that a connection between two components does not necessarily mean a direct, unimpeded connection, as a variety of other components may reside between the two components of note. Consequently, a connection does not necessarily mean a direct, unimpeded connection unless otherwise noted.

Further, wherever feasible and convenient, like reference numerals are used in the figures and the description to refer to the same or like parts or steps. The drawings are in a simplified form and not to precise scale. It is understood that the disclosure is presented in this manner merely for explanatory purposes and the principles and embodiments described herein can be applied to antibodies and/or composition components that have configurations other than as specifically described herein. Indeed, it is expressly contemplated that the components of the composition and compounds of the present disclosure may be tailored in furtherance of the desired application thereof.

Unless defined otherwise, all technical and scientific terms used herein have the same meaning as commonly understood by one of skill in the chemical and biological arts. Although any methods and materials similar to or equivalent to those described herein can be used in the practice or testing of the subject of the present application, the preferred methods and materials are described herein. Additionally, as used in this specification and the appended claims, the singular forms "a". "an" and "the" include plural referents unless the content clearly dictates otherwise. Thus, for example, where a compound/composition is substituted with "an" alkyl or aryl, the compound/composition is optionally substituted with at least one alkyl and/or at least one aryl.

When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range can vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Substantially" can allow for a degree of variability in a value or range, for example, within 90%, within 95%, or within 99% of a stated value or of a stated limit of a range.

The terms "sequence identity" or "percent identity," in the context of two or more polypeptide sequences, refer to two or more sequences or subsequences that are the same or have a specified percentage of peptides that are the same (i.e. about 60% identity, preferably 65%, 70%, 75%, 80%, 85%, 90%, 91%, 92%, 93%, 94%, 95%, 96%, 97%, 98%, 99%, or higher identity over a specified region when compared and aligned for maximum correspondence over a comparison window or designated region such as a targeted gene) as measured using sequence comparison algorithms known in the art, or by manual alignment and visual inspection. Such sequences are then said to be "substantially identical." In other words, identity exists over one or more regions of the overall sequence as long as the general shape and structure of the molecule, and hydrogen bond(s) where appropriate, are maintained such that it substantially fits into the targeted binding site and functions as an agonist thereto.

The term "fully canine antibody" refers to an antibody that comprises canine immunoglobulin protein sequences only. A fully canine antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully canine antibody may contain rat carbohydrate chains if produced in a rat, in a rat cell, or in a hybridoma derived from a rat cell. Similarly, "rat antibody" refers to an antibody that comprises rat immunoglobulin sequences only.

In certain embodiments, the compounds, compositions and methods of the present disclosure are useful for the prevention and/or treatment of cancer. In certain embodiments, the compounds and/or compositions provided are also useful for the treatment of cancer. In certain embodiments, the compounds provided herein are provided or used alone, in conjunction with a targeting agent, and/or in a combination therapy with other interventions such as cytokine-based and other immunotherapies.

The invention claimed is:

1. An antibody or antigen binding fragment thereof that binds canine programmed death ligand 1 (PD-L1) in a canine subject with specificity, wherein the antibody or antigen binding fragment comprises a light chain and a heavy chain, wherein the light chain comprises amino acid residues 21-243 of SEQ ID NO: 27, and wherein the heavy chain comprises amino acid residues 20-472 of SEQ ID NO: 3.

2. The antibody or antigen binding fragment of claim 1, wherein the antibody or antigen binding fragment thereof is completely caninized.

3. The antibody or antigen binding fragment of claim 1, wherein the antibody or antigen binding fragment is a chimeric form of a caninized antibody or antigen binding fragment.

4. A method for treating cancer in a canine subject in need thereof, comprising administering to a canine subject a therapeutically effective amount of the antibody or antigen binding fragment of claim 1.

5. The method of claim 4, wherein the antibody or antigen binding fragment thereof is formulated into a pharmaceutical composition that is administered to said canine subject.

6. The method of claim 4, wherein the therapeutically effective amount is from about 2 mg/kg of subject body weight to about 5 mg/kg of subject body weight.

7. The method of claim 4, wherein the cancer is invasive urothelial carcinoma.

8. A pharmaceutical composition comprising an antibody or antigen binding fragment thereof and a pharmaceutically acceptable excipient, wherein the antibody or antigen binding fragment comprises a light chain and a heavy chain, wherein the light chain comprises amino acid residues 21-243 of SEQ ID NO: 27, and wherein the heavy chain comprises amino acid residues 20-472 of SEQ ID NO: 3.

9. The pharmaceutical composition of claim 8, wherein the antibody or antigen binding fragment thereof is completely caninized.

10. A medicament for treating cancer in a canine subject, the medicament comprising a pharmaceutical composition according to claim 8.

11. The medicament of claim 10, wherein said medicament is a unit dosage form further comprising one or more pharmaceutically acceptable carriers, adjuvants, diluents, excipients, and/or vehicles.

12. The medicament of claim 10, wherein the cancer is invasive urothelial carcinoma.

* * * * *